United States Patent
Kim et al.

(10) Patent No.: US 10,851,175 B2
(45) Date of Patent: Dec. 1, 2020

(54) ANTI-MESOTHELIN ANTIBODY AND COMPOSITION COMPRISING THE SAME

(71) Applicants: MOGAM INSTITUTE FOR BIOMEDICAL RESEARCH, Yongin-si (KR); GREEN CROSS CORPORATION, Yongin-si (KR)

(72) Inventors: Dong-Sik Kim, Yongin-si (KR); Eun Jung Song, Yongin-si (KR); Mijung Lee, Yongin-si (KR); Eun-Hee Lee, Yongin-si (KR); Miyoung Oh, Yongin-si (KR); Jae Chan Park, Yongin-si (KR); Kisu Kim, Yongin-si (KR); Sujeong Kim, Yongin-si (KR); Hyung-Kwon Lim, Yongin-si (KR); Kyuhyun Lee, Yongin-si (KR); Jongwha Won, Yongin-si (KR); Soongyu Choi, Yongin-si (KR); Young Seoub Park, Yongin-si (KR)

(73) Assignees: MOGAM INSTITUTE FOR BIOMEDICAL RESEARCH, Gyeonggi-do (KR); GREEN CROSS CORPORATION, Gyeonggi-do (KR)

( * ) Notice: Subject to any disclaimer, the term of this patent is extended or adjusted under 35 U.S.C. 154(b) by 293 days.

(21) Appl. No.: 15/762,885

(22) PCT Filed: Sep. 23, 2016

(86) PCT No.: PCT/KR2016/010604
§ 371 (c)(1),
(2) Date: Mar. 23, 2018

(87) PCT Pub. No.: WO2017/052241
PCT Pub. Date: Mar. 30, 2017

(65) Prior Publication Data
US 2018/0346588 A1 Dec. 6, 2018

(30) Foreign Application Priority Data
Sep. 24, 2015 (KR) .................. 10-2015-0135755

(51) Int. Cl.
*C07K 16/18* (2006.01)
*C07K 16/30* (2006.01)
*C07K 16/28* (2006.01)

(52) U.S. Cl.
CPC .............. *C07K 16/30* (2013.01); *C07K 16/18* (2013.01); *C07K 16/28* (2013.01); *C07K 2317/21* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 2006/0204506 A1 | 9/2006 | Ebel et al. |
| 2014/0004121 A1 | 1/2014 | Fanslow, III et al. |
| 2015/0086553 A1 | 3/2015 | Han et al. |

FOREIGN PATENT DOCUMENTS

| | | |
|---|---|---|
| KR | 1020100097660 A | 9/2010 |
| KR | 1020140014116 A | 2/2014 |
| WO | 2009045957 A1 | 4/2009 |
| WO | 2009054957 A1 | 4/2009 |
| WO | 2012087962 A2 | 6/2012 |

OTHER PUBLICATIONS

White et al. (2001, Ann. Rev. Med., 2001, 52:125-145) (Year: 2001).*
Meibohm (Pharmacokinetics and Pharmacodynamics of Biotech Drugs, Wiley-VHC, 2006, chapter 3, p. 45-91) (Year: 2006).*
Armin Rump, et al., "Binding of Ovarian Cancer Antigen CA125/MUC16 to Mesothelin Mediates Cell Adhesion", The Journal of Biological Chemistry, vol. 279, No. 10, pp. 9190-9198, 2004.
David Filpula, et al., "Releasable PEGylation of Mesothelin Targeted Immunotoxin SS1P Achieves Single Dosage Complete Regression of a Human Carcinoma in Mice", Bioconjugate Chem. 2007, 18, 773-784.
Dominic Fan, et al., "Targeted Therapy against Human Lung Cancer in Nude Mice by High-Affinity Recombinant Antimesothelin Single-Chain Fv Immunotoxin", Molecular Cancer Therapeutics, vol. 1., 595-600, 2002.
Ingegerd Hellstrom, et al., "Mesothelin Variant 1 is Released from Tumor Cells as a Diagnostic Marker", Cancer Epidemiology Biomarkers Prey 2006, 15(5):1014-1020.
Jennifer AA Gubbels, et al., "Mesothelin-MUC16 binding is a high affinity, N-glycan dependent interaction that facilitates peritoneal metastasis of ovarian tumors", Molecular Cancer 2006, 5:50 (15 pp.).
Kai Chang, et al., "Isolation and Chacacerization of a Monoclonal Antibody, K1, Reactive with Ovarian Cancers and Normal Mesothelium", Int. J. Cancer: 50, 373-381 (1992).
Kai Chang, et al., "Molecular cloning of mesothelin, a differentiation antigen present on mesothelium, mesotheliomas, and ovarian cancers", Proc. Natl. Acad. Sci. USA, vol. 93, pp. 136-140, 1996.
Nozomi Yamaguchi, et al., "A Novel Cytokine Exhibiting Megakaryocyte Potentiating Activity From a Human Pancreatic Tumor Cell Line HPC-Y5", The Journal of Biological Chemistry, vol. 269, No. 2, 1994, 805-808.

(Continued)

*Primary Examiner* — Meera Natarajan
(74) *Attorney, Agent, or Firm* — Cantor Colburn LLP

(57) ABSTRACT

The present invention relates to an antibody specifically bound to mesothelin (MSLN), a nucleic acid encoding the antibody, a vector and a host cell including the nucleic acid, a method for producing the antibody, and a pharmaceutical composition for treating cancer or tumor including the antibody as an active ingredient. The antibody specifically bound to the mesothelin according to the present invention has high affinity and specificity to an antigen, such that it is possible to develop an antibody effectively usable for treatment or diagnosis of cancer or tumor diseases.

15 Claims, 6 Drawing Sheets
(6 of 6 Drawing Sheet(s) Filed in Color)
Specification includes a Sequence Listing.

(56) References Cited

OTHER PUBLICATIONS

Pedram Argani, et al., "Mesothelin Is Overexpressed in the Vase Majority of Ductal Adenocarcinomas of the Pancreas: Identification of a New Pancreatic Cancer Marker by Serial Analysis of Gene Expression (SAGE)", Clinical Cancer Research, vol. 7, 3862-3868, 2001.
Raffit Hassan, et al., "Anti-Tumor Activity of K1-LysPE38QQR, an Immunotoxin Targeting Mesothelin, a Cell-Surface Antigen Overexpressed in Ovarian Cancer and Malignant Mesothelioma" Journal of Immuinotherapy, 23(4):473-479, 2000.
Raffit Hassan, et al., "Antitumor Activity of SS(dsFv)PE38 and SS1(dsFv)PE38, Recombinant Antimesothelin Immunotoxins against Human Gynecologic Cancers Grown in Organotypic Culture in Vitro", Clinical Cancer Research,, vol. 8, 3520-3526, 2002.
Raffit Hassan, et al., "Mesothelin: A New Target for Immunotherapy", Clinical Cancer Research, vol. 10, 3937-3942, Jun. 15, 2004.
Tapan K. Bera, et al., "Mesothelin Is Not Required for Normal Mouse Development or Reproduction", Molecular and Cellular Biology, Apr. 2000, 20(8):2902-2906.
Yi-Fan Zhang, et al., "New High Affinity Monoclonal Antibodies Recognize non-Overlapping Epitopes on Mesothelin for Monitoring and Treating Mesothelioma", Scientific Reports, 5:09928, doi: 10.1038/srep09928 (2015).(14 pp.).
Zhanat E. Muminova, et al., "Characterization of human mesothelin transcripts in ovarian and pancreatic cancer", BMC Cancer 2004, 4:19, 10 pp.
Canadian Office Action, dated Apr. 11, 2019, Application No. 2,999,237, 7 pp.
Extended European Search Report dated Apr. 29, 2019, for Application No. 16848966.4.
Japanese Office Action dated Mar. 22, 2019, application No. 2018-515766, 7 pp, with English Translation.
Kiyoshi Ishikawa, et al., "Establishment of novel mAb to human ERC/mesothelin useful for study and diagnosis of ERC/mesothelin-expressing cancers", Pathology International 2009; 59: 161-166.
Masanori Onda, et al., "New Monoclonal Antibodies to Mesothelin Useful for Immunohistochemistry, Fluorescence-Activated Cell Sorting,Western Blotting, and ELISA", Clin Cancer Res 11(16) Aug. 15, 2005; 5840-5846.
Stuart Rudikoff, et al., "Single amino acid substitution altering antigen-binding specificity", Proc. Nat. Acad. Sci. USA vol. 79, pp. 1979-1983, Mar. 1982.
English Translation of Notice of Allowance dated Jun. 30, 2020 in the Japanese patent application No. 2018-515766.
Kiyoshi Ishikawa, et al., Establishment of novel mAb to human ERC/mesothelin useful or study and diagnosis of ERC/mesothelin-expressing cancers, Pathology International 2009; 59: 161-166.
Masanori Onda, et al., New Monoclonal Antibodies to Mesothelin Useful for Immunohistochemistry, Fluorescence-Activated Cell Sorting,Western Blotting, and ELISA, Clin Cancer Res., Aug. 15, 2005, 11 (16), p. 5840-5846.
Notice of Allowance dated Jun. 30, 2020 in the Japanese patent application No. 2018-515766. (English translation provided separately).
Yi-Fan Zhang, et al., New High Affinity Monoclonal Antibodies Recognize Non-Overlapping Epitopes on Mesothelin for Monitoring and Treating Mesothelioma, Scientific Reports, vol. 5, May 21, 2015 (May 21, 2015), 9928; doi: 10.1038/srep09928, pp. 1-14.

* cited by examiner

ANTI-MESOTHELIN ANTIBODY AND COMPOSITION COMPRISING THE SAME

CROSS REFERENCE TO RELATED APPLICATIONS

This application is a National Stage application of International Application No. PCT/KR2016/010604, filed Sep. 23, 2016, which claims the benefit of Korean Patent Application No. 10-2015-0135755 filed on Sep. 24, 2015, each of which is incorporated by reference in its entirety herein.

TECHNICAL FIELD

The present invention relates to an antibody specifically bound to mesothelin (MSLN), a nucleic acid encoding the antibody, a vector and a host cell including the nucleic acid, a method for producing the antibody, and a pharmaceutical composition for treating cancer or tumor including the antibody as an active ingredient.

BACKGROUND ART

An antibody is highly effective for treating various cancers or tumors including solid tumors. For example, Herceptin has been used successfully in the treatment of breast cancer, and Avastin has been used successfully in the treatment of colon cancer. The core of the development of cancer or tumor treatment with the antibody is to develop an antibody against a membrane surface protein predominantly expressed (over-expression) in tumor cells.

Mesothelin (MSLN) is a glycoprotein as 69 to 71 kDa precursor polypeptide, and is expressed as a precursor form of glycophosphatidylinositol (GPI)-bound protein on a cell surface. The precursor is separated from a furin site (RPRFRR) in the precursor, and forms a 32 kDa megakaryocyte potentiating factor (MPF) that is N-terminal polypeptide released from the cell with a GPI-bound mesothelin membrane protein that is 40 kDa C-terminal polypeptide (Hassan R. et al., Clin. Cancer Res., 10(12 Pt 1):3937-3942, 2004; Chang, K. et al., Proc. Natl. Acad. Sci. USA, 93(1): 136-40, 1996).

The mesothelin was named a megakaryocyte potentiating factor (MPF) since it had been purified from a human pancreatic cell line HPC-Y5, and observed to have a megakaryocyte-potentiating activity (Yamaguchi N. et al., J. Biol. Chem. 269:805-808, 1994).

Function of the mesothelin has not been clearly found yet. Moreover, fatal re-productive, hematological or anatomical abnormality has not been observed when producing a mesothelin gene expression-deficient mouse (Bera, T. K. et al., Mol. Cell. Biol. 20(8):2902-2906, 2000).

The mesothelin is a glycoprotein present on a cell surface of a mesothelial lining of peritoneal, pleural and pericardial coeloms. The mesothelin is predominantly expressed (over-expressed) in mesothelioma which is cancer/tumor cell, ovarian cancer, pancreatic cancer, stomach cancer, lung cancer and endometrial cancer. On the contrary, the expression thereof is limited in a normal cell, for example, a mesothelial cell, which may be an ideal target of tumor treatment (Argani, P. et al., Clin. Cancer Res., 7(12):3862-8, 2001; Hassan, R., et al., Clin. Cancer Res., 10(12 Pt 1):3937, 2004).

Further, the mesothelin specifically reacts (interacts) to CA125 (MUC-16) that is a mucin-like glycoprotein present on a surface of the tumor cell confirmed as an antigen of ovarian cancer. Specifically, it appears that the binding of CA125 to the membrane bound mesothelin is able to mediate heterotype cell adhesion and metastasis, and the CA125 and the mesothelin are co-expressed in an advanced ovarian adenocarcinoma (Rump, A. et al., J. Biol. Chem., 279(10): 9190-8, 2004). The expression of the mesothelin in an endothelium of a peritoneal cavity is correlated with a preferred part for forming metastasis of the ovarian cancer, and the mesothelin-CA125 binding facilitates peritoneal metastasis of ovarian tumor (Gubbels, J. A. et al., Mol. Cancer, 5(1):50, 2006).

In recent years, an antibody-based targeted treatment targeting the lung cancer, the ovarian cancer, and the pancreatic cancer that express the mesothelin has been developed. As an example, mAb K1 produced by immunization of the mouse has been developed as a primary antibody against a membrane-bound mesothelin polypeptide (Chang, K., et al., Int. J. Cancer, 50(3):373, 1992). However, due to low affinity of the mAb K1 antibody and poor internalization rate, an immunotoxin consisting of mAb K1 linked to a truncation type of chemically modified Pseudomonas exotoxin A is not suitable for clinical development (Hassan, R., et al., J. Immunother., 23(4):473, 2000; Hassan, R., et al., Clin. Cancer Res., 10(12 Pt 1):3937, 2004). Then, single-chain antibodies having a higher affinity including SS1-(dsFv)-PE38 have been developed, which have an ability to kill tumor cells in vitro (Hassan, R., et al., Clin. Cancer Res., 8(11):3520, 2002), and an efficacy in rodent models of human mesothelin-expression tumors (Fan, D., et al., Mol. Cancer Ther., 1(8):595, 2002). It may be appreciated from the above results that the mesothelin is a target appropriate for immunotherapy of multiple cancers. However, it was observed that the SS1-(dsFv)-PE38 has immuno-genicity in clinical trials, such that a second administration thereof has been discontinued in most patients, and the SS1-(dsFv)-PE38 tends to be rapidly removed from the blood, and thus, there is an attempt to induce pegylation of the SS1-(dsFv)-PE38 into a form of fusion protein, thereby increasing antibody persistence in vivo (Filpula, D., et al., Bioconjugate Chem., 18(3):773, 2007).

The clinical trial of the immunotoxin cancer therapy having xenograft rodent as a cancer model is often limited by deficiency of cross-reactivity between a treatment antibody and a rodent homologue thereof. In addition, a neutralizing anti-mouse Fv antibody formed from a patient treated with a rodent-derived antibody or chimeric antibody may cause dose limiting toxicity or may reduce therapeutic efficacy. Therefore, in order to increase efficacy of the cancer treatment, a targeting antibody combined with increased affinity, a reduced dissociation rate, and rodent cross-reactivity with regard to a mesothelin antigen is required.

In addition, as an additional property of the novel anti-mesothelin (MSLN) antibody, it needs to maintain affinity with regard to the mesothelin expressed on the cell surface of different cancer or tumor cells. The mesothelin is a highly variable protein, and is subjected to glycosylation as well as proteolysis after translation in multiple parts (Hassan, R., et al., Clin Cancer Res., 10(12 Pt 1):3937, 2004). It appears that a transcript variant 1 (Genbank NM_005823) represents the major species shown in tumor cell lines tested to date, but since three different splicing variants were detected, variability is extended to a transcription level (Muminova, Z. E., et al., BMC Cancer, 4:19, 2004; Hellstrom, I., et al., Cancer Epidemiol. Biomarkers Prev. 15(5):1014, 2006). Accordingly, an effective anti-endothelin antibody includes variability in the glycosylation pattern that expresses different forms of mesothelins, but it is required to be unchangeably bound to a mesothelin epitope expressed on cancer or tumor cell surfaces derived from different patients, which is independent from individual variability.

Therefore, the present inventors made an effort to produce a novel antibody specifically bound to MSLN, and as a result, invented the novel antibody having high affinity with regard to the MSLN over-expressed in cancer cells, and found a potential of the antibody according to the present invention as an effective anti-cancer therapeutic agent, and completed the present invention.

DISCLOSURE OF INVENTION

Technical Problem

An object of the present invention is to provide a novel antibody specifically bound to mesothelin (MSLN), a nucleic acid encoding the antibody, a vector and a host cell including the nucleic acid, a method for producing the same, and a pharmaceutical composition for treating cancer or tumor including the antibody as an active ingredient.

Another object of the present invention is to provide a novel antibody specifically bound to the mesothelin (MSLN).

Solution to Problem

In order to achieve the foregoing objects, the present invention provides a mesothelin-specific antibody including: a heavy chain variable region including a heavy chain CDR1 having an amino acid sequence of SEQ ID NO: 9, 15, 21, 27, or 59; a heavy chain CDR2 having an amino acid sequence of SEQ ID NO: 10, 16, 22, 28, 60, 65, 71, 75, 80, 84, 121, 122, 123 or 125; a heavy chain CDR3 having an amino acid sequence of SEQ ID NO: 11, 17, 23, 29, 61, 66, 72, 76, 81, 85, 124 or 126.

In addition, the present invention provides a mesothelin-specific antibody including: a light chain variable region including a light chain CDR1 having an amino acid sequence of SEQ ID NO: 12, 18, 24, 30, 62, 67, 70, 77, 86 or 117; a light chain CDR2 having an amino acid sequence of SEQ ID NO: 13, 19, 25, 63, 68, 73, 78 or 82; a light chain CDR3 having an amino acid sequence of SEQ ID NO: 14, 20, 26, 64, 69, 74, 79, 83, 87, 118, 119 or 120.

Further, the present invention provides a mesothelin-specific antibody including: a heavy chain variable region including an amino acid sequence of SEQ ID NO: 1, 3, 5, 7, 46, 48, 51, 53, 55, 57, 112, 113, 114, 115 or 116 and a light chain variable region including an amino acid sequence of SEQ ID NO: 2, 4, 6, 8, 47, 52, 54, 56, 58, 109, 110 or 111.

In addition, the present invention provides a nucleic acid encoding the MSLN-specific antibody; and a vector containing the nucleic acid; and a cell into which the vector is introduced.

Further, the present invention provides a pharmaceutical composition for treating cancer or tumor including the anti-MSLN antibody as an active ingredient.

BRIEF DESCRIPTION OF DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

As used herein, term "mesothelin" or "MSLN" refers to any variants, isoforms and species homologs of human MSLN that is naturally expressed by cells.

Term "human mesothelin" refers to a human sequence mesothelin such as a complete amino acid sequence of human mesothelin having Genbank Accession No. NP_005814.

In an embodiment of the present invention, monoclonal antibodies that are structurally characterized to be specifically bound to the mesothelin represented by SEQ ID NO: 127 and separated, such as "clone MI323", "clone MI329", "clone MI403" and "clone MI407", and "clone MS501", "clone MS502", "clone MS503", "clone MS504", "clone MS505" and "clone MS506", and "clone C2G1", "clone C2G4", "clone C3C8", "clone 54", "clone 56", "clone 2-30", "clone 2-73" and "clone 2-78", and "clone 56-C2G4", "clone 2-30-C2G4", "clone 2-73-C2G4" and "clone 2-78-C2G4" were produced.

Amino acid sequences with regard to a heavy chain CDR and a light chain CDR of each antibody are shown in Tables 2, 5, 12, and 16 below. As shown in Tables 1, 4, 11, and 15, an anti-MSLN antibody may include an amino acid sequence of a heavy chain variable region and a light chain variable region or a sequence having homology thereto.

In another embodiment of the present invention, individual antibody clones of purified antibodies, i.e., "clone MI323", "clone MI329", "clone MI403", "clone MS502", and "clone C2G1", "clone C2G4", "clone C3C8", and "clone 56-C2G4", "clone 2-30-C2G4", "clone 2-73-C2G4" or "clone 2-78-C2G4" with regard to a recombinant human MSLN, were selected by using an enzyme linked immunosorbent assay (ELISA) (data not shown), and quantitative binding force was measured by using a Biacore T-200 (GE Healthcare, U.S.A.) biosensor (Example 2-5, Example 3-11, Examples 3-14). As a result, as shown in Tables 8, 14, and 18 below, all of the produced clone antibodies have affinity to the mesothelin even though there is a slight difference.

Figure 5:
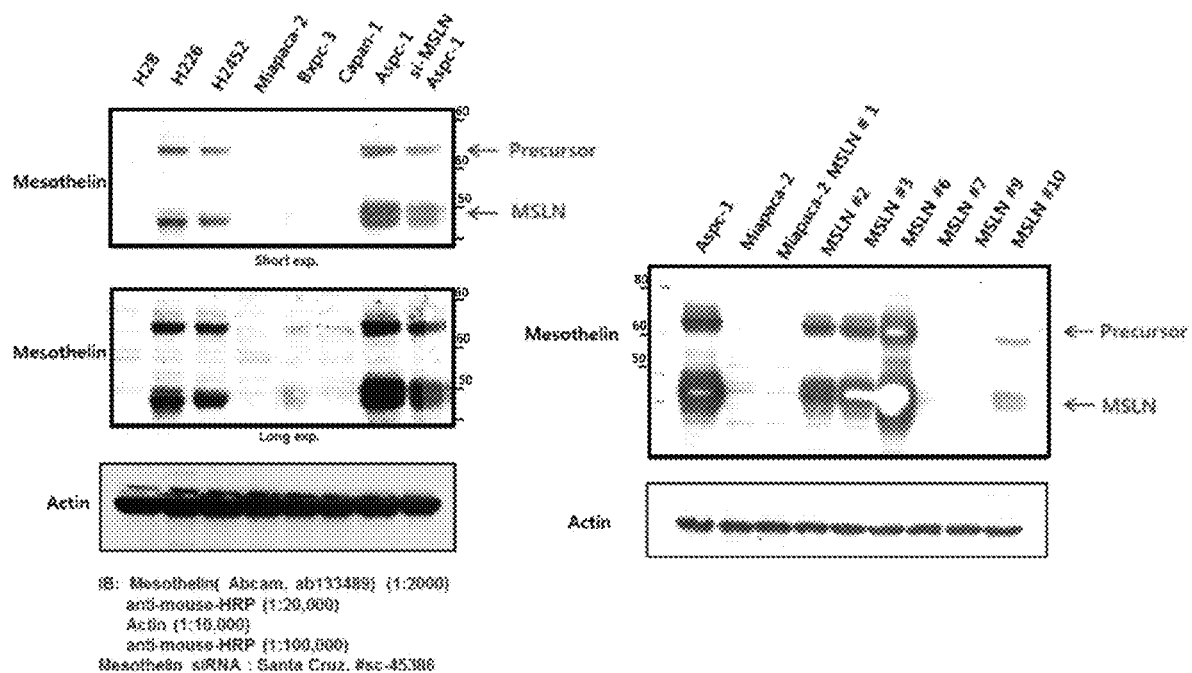
FIG. 5 illustrates a precursor form and a mature form of the MSLN on SDS-PAGE.

In another embodiment of the present invention, in order to evaluate whether the anti-MSLN antibody derived from the immune and synthetic library is selectively bound to a MSLN-expressing cell, an expression amount of the MSLN is measured in a cancer cell line, and an antibody binding to each cell is confirmed by FACS test. As a result, as illustrated in FIG. 5, it was confirmed that H28, MiaPaCa-2, BxPC-3, Capan-1 cell lines are MSLN-negative, and H226, H2452(H2052), AsPC-1 are MSLN-positive by measuring whether there are the MSLN having 70 kDa precursor form and 40 to 50 kDa mature form from each cancer cell line.

Figure 8:
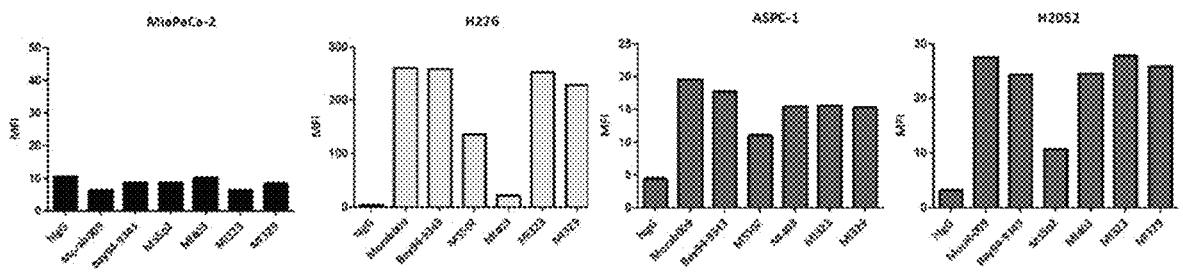
FIG. 8 illustrates MFI values obtained by confirming whether the anti-MSLN antibody is bound to a cell membrane of mesothelioma (H226, H2052) and pancreatic cancers (AsPC-1) through FACS.

In addition, as a result obtained by performing selective binding analysis of anti-MSLN candidate antibodies with regard to the MSLN-expressing cell lines (H226, H2452 (H2052), AsPC-1), as illustrated in FIG. 8 and Table 19, all of the MI323, MI329, MI403, MS502 candidate antibodies with regard to the MSLN of mesothelioma and pancreatic cancer cell lines have significant binding force even though there is a slight difference in binding degree. In particular, the MI323 candidate antibody has an excellent binding aspect.

Figure 9:
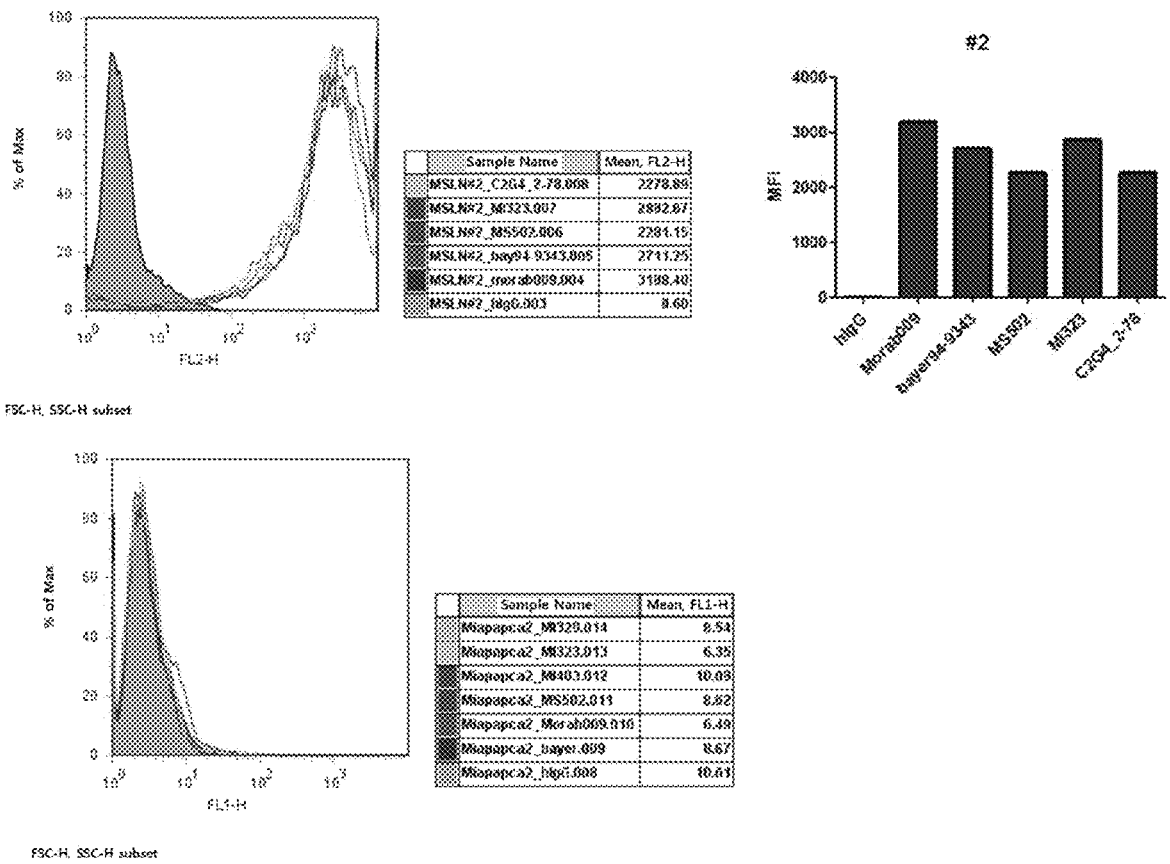
FIG. 9 illustrates results obtained by confirming whether the anti-MSLN antibody of the present invention is selectively bound to tumor cells expressing the MSLN.

Further, as a result obtained by evaluating whether the MI323 candidate antibody having the excellent binding aspect with regard to the MSLN, MS502 candidate antibody having a different pattern of Biacore KD(Koff/Kon) value, and a heavy chain variable region mutation 2-78-C2G4 candidate antibody produced from the MS502 candidate antibody are selectively bound to MSLN-expressing tumor cells, in MiaPaCa-MSLN #2 cell that over-expresses the MSLN and MiaPaCa-2 that does not over-express the MSLN, as illustrated in FIG. 9, the MI323, MS502, and 2-78-C2G4 candidate antibodies have excellent binding aspect in the MiaPaCa-MSLN #2 cell that over-expresses the MSLN as compared to the MiaPaCa-2.

Therefore, the present invention relates to an antibody specifically bound to mesothelin (MSLN), preferably, an antibody specifically bound to mesothelin represented by SEQ ID NO: 127.

The antibody specifically bound to the mesothelin according to the present invention is characterized by containing a heavy chain variable region including a heavy chain CDR1 having an amino acid sequence of SEQ ID NO: 9, 15, 21, 27, or 59; a heavy chain CDR2 having an amino acid sequence of SEQ ID NO: 10, 16, 22, 28, 60, 65, 71, 75, 80, 84, 121, 122, 123 or 125; a heavy chain CDR3 having an amino acid sequence of SEQ ID NO: 11, 17, 23, 29, 61, 66, 72, 76, 81, 85, 124 or 126.

The antibody specifically bound to the mesothelin according to the present invention is characterized by containing a light chain variable region including a light chain CDR1 having an amino acid sequence of SEQ ID NO: 12, 18, 24, 30, 62, 67, 70, 77, 86 or 117; a light chain CDR2 having an amino acid sequence of SEQ ID NO: 13, 19, 25, 63, 68, 73, 78 or 82; a light chain CDR3 having an amino acid sequence of SEQ ID NO: 14, 20, 26, 64, 69, 74, 79, 83, 87, 118, 119 or 120.

In the present invention, the antibody specifically bound to the mesothelin may contain a heavy chain variable region including a sequence having at least 80% homology, preferably, at least 90% homology, and more preferably, 100% homology to the amino acid sequence of SEQ ID NO: 1, 3, 5, 7, 46, 48, 51, 53, 55, 57, 112, 113, 114, 115 or 116, and the antibody may contain a light chain variable region including a sequence having at least 80% homology, preferably, at least 90% homology, and more preferably, 100% homology to the amino acid sequence of SEQ ID NO: 2, 4, 6, 8, 47, 52, 54, 56, 58, 109, 110 or 111.

In the present invention, the antibody specifically bound to the mesothelin is characterized by containing the heavy chain variable region including the amino acid sequence of SEQ ID NO: 1, 3, 5, 7, 46, 48, 51, 53, 55, 57, 112, 113, 114, 115 or 116, and the light chain variable region including the amino acid sequence of SEQ ID NO: 2, 4, 6, 8, 47, 52, 54, 56, 58, 109, 110 or 111, and the antibody may be a human monoclonal antibody, but is not limited thereto.

The amino acid sequence of the antibody may be substituted by conservative substitution. The "conservative substitution" refers to modification of polypeptide including substitution of at least one amino acid with an amino acid having similar biochemical properties to corresponding polypeptide without causing loss of biological or biochemical function. "Conservative amino acid substitution" refers to a substitution in which an amino acid residue is replaced with an amino acid residue having similar side chains. Classes of the amino acid residues having similar side chains are defined in the art. These classes include amino acids having basic side chains (e.g., lysine, arginine, histidine), amino acids having acidic side chains (e.g., aspartic acid, glutamic acid), amino acids having uncharged polar side chains (e.g., glycine, asparagine, glutamine, serine, threonine, tyrosine, cysteine), amino acids having non-polar side chains (e.g., alanine, valine, leucine, isoleucine, proline, phenylalanine, methionine, tryptophan), amino acids having beta-branched side chains (e.g., threonine, valine, isoleucine), and amino acids having aromatic side chains (e.g., tyrosine, phenylalanine, tryptophan, histidine). It is anticipated that the antibody of the present invention is able to still retain an activity while having the conservative amino acid substitution.

Term "substantial homology" refers that when two kinds of nucleic acids or two kinds of polypeptides or designated sequences thereof are optimally aligned and compared, the nucleic acids and polypeptides having appropriate nucleotide or amino acid insertion or deletion have at least about 80% identity to the nucleotide or the amino acid, generally, have at least about 85%, preferably about 90%, 91%, 92%, 93%, 94% or 95%, and more preferably at least about 96%, 97%, 98%, 99%, 99.1%, 99.2%, 99.3%, 99.4% or 99.5% to the nucleotide or the amino acid. Alternatively, when a fragment is hybridized with a complementary strand thereof under selective hybridization conditions, there is substantial homology to the nucleic acid. The present invention includes a nucleic acid sequence and a polypeptide sequence having substantial homology with regard to the above-described specific nucleic acid sequence and amino acid sequence.

In the antibody according to the present invention, for example, the heavy chain ($V_H$) CDR1, 2 and 3 sequences and the light chain ($V_L$) CDR1, 2 and 3 sequences shown in Table 2, Table 5, Table 12, and Table 16 may be formed by mixing structurally similar heavy chain ($V_H$) and light chain ($V_L$) sequences to be arranged in the CDR1, 2 and 3 of the heavy chain ($V_H$)/light chain ($V_L$) pairs.

As used herein, term "antibody" or "antibody composition" refers to a preparation of antibody molecules having single molecule composition. Here, a monoclonal antibody composition represents single binding specificity and affinity for a specific epitope. Accordingly, term "human monoclonal antibody" refers to an antibody having a variable region and a constant region derived from a human wiring immunoglobulin sequence, and representing single binding specificity. A human antibody of the present invention may include amino acid residue that is not encoded by the human wiring immunoglobulin sequence (for example, mutants introduced by in vitro random or site-specific mutagenesis, or by in vivo somatic mutation).

The "antibody" used herein is an immunoglobulin molecule which is immuno-logically reactive to a specific antigen, and means a protein molecule acting as a receptor that specifically recognizes an antigen, and may include all of a polyclonal antibody, a monoclonal antibody (single clone antibody), a whole antibody, and an antibody fragment. Further, the antibody may include a chimeric antibody (e.g., humanized murine antibody) and a bivalent or bispecific molecule (e.g., bispecific antibody), a diabody, a triabody, and a tetrabody.

The whole antibody has a structure having two full length light chains and two full length heavy chains, and each light chain may be linked to a heavy chain via a disulfide bond. The whole antibody includes IgA, IgD, IgE, IgM, and IgG, and the IgG is a subtype, and includes IgG1, IgG2, IgG3, and IgG4. The antibody fragment means a fragment retaining an antigen-binding function, and includes Fab, Fab', F(ab')2, scFv, and Fv, etc.

The Fab has a structure of variable regions of a light chain and a heavy chain and a constant region of the light chain and a first constant region (CH1 domain) of the heavy chain, and has one antigen-binding site. The Fab' is different from the Fab in that the Fab' has a hinge region including one or more cysteine residues at C terminal of a heavy chain CH1 domain. The F(ab')2 antibody is produced by achieving the disulfide bonding of the cysteine residue in the hinge region of the Fab'.

The Fv (variable fragment) refers to the minimum antibody fragment only having the heavy chain variable region and the light chain variable region. In double-stranded Fv(dsFv), the heavy chain variable region and the light chain variable region are linked by the disulfide bond. In the single chain Fv(scFv), the heavy chain variable region and the light chain variable region generally are linked by a covalent bond using a peptide linker. These antibody fragment may be obtained by using a proteolytic enzyme (for example, the Fab may be obtained by restriction-cutting the whole antibody with papain, and F(ab')2 fragment may be obtained by cutting with pepsin), and may be constructed by a recombinant DNA technology (for example, amplification by PCR (Polymerase Chain Reaction) method using DNA encoding the heavy chain of the antibody or the variable region thereof and DNA encoding the light chain or the variable region thereof as a template and using a primer pair, and amplification with combination of the DNA encoding the peptide linker of the primer pair allowing both ends thereof to link to the heavy chain or the variable region thereof and the light chain or the variable region thereof, respectively).

The immunoglobulin has heavy chains and light chains, wherein the respective heavy chains and light chains include a constant region and a variable region (these regions are also known as domain). The light chain variable region and the heavy chain variable region include 3 multi-available regions called complementarity-determining region (hereinafter, referred to as "CDR"), and four framework regions. The CDR mainly acts to bind to an epitope of the antigen. The CDRs of the respective chains are sequentially called CDR1, CDR2, and CDR3 generally starting from N-terminal, and also identified by the chains in which specific CDRs are located.

The monoclonal antibody (single clone antibody) used herein means an antibody molecule of single molecular composition substantially obtained in the same antibody population, and may have single binding specificity and affinity for a specific epitope.

The monoclonal antibody (single clone antibody) used herein is a molecule derived from a human immunoglobulin, and all of the amino acid sequences configuring the antibody including a complementarity-determining region, a structure region are configured of human immunoglobulin amino acid sequences. The human antibody is typically used in the treatment of human diseases, which is advantageous in that i) it more favorably interacts with the human immune system, which more effectively destroys target cells by complement-dependent cytotoxicity (CDC) or antibody-dependent cell mediated cytotoxicity (ADCC), ii) the human immune system does not recognize the antibody as a foreign material, and iii) even when a smaller amount of drug is administered less frequently, a half-life in a human circulatory system is similar to that of a naturally occurring antibody.

Terms "clone M1323", "clone M1329", "clone M1403" and "clone M1407" and "clone MS501", "clone MS502", "clone MS503", "clone MS504", "clone MS505" and "clone MS506" and "clone C2G1", "clone C2G4", "clone C3C8", "clone 54", "clone 56", "clone 2-30", "clone 2-73" and "clone 2-78" and "clone 56-C2G4", "clone 2-30-C2G4", "clone 2-73-C2G4" and "clone 2-78-C2G4" that are antibodies specifically bound to MSLN used herein mean antibodies bound to the MSLN and causing inhibition of biological activity of the MSLN, and may be used by mixing an anti-MSLN antibody.

Here, the "clone M1323", "clone M1329", "clone M1403" and "clone M1407" are antibodies obtained by immunizing a mouse with recombinant human MSLN, and the clone MS501", "clone MS502", "clone MS503", "clone MS504", "clone MS505" and "clone MS506" are antibodies obtained from a phage display from a scFV library, and "clone C2G1", "clone C2G4", "clone C3C8", "clone 54", "clone 56", "clone 2-30", "clone 2-73" and "clone 2-78" are antibodies obtained by introducing mutation into the "clone MS502" as shown in Table 9, and the "clone 56-C2G4", "clone 2-30-C2G4", "clone 2-73-C2G4" and "clone 2-78-C2G4" are antibodies produced by combination between introduced mutation antibodies.

$K_D$ (equilibrium dissociation constant) of the antibody to the MSLN may be exemplified as follows.

(1) the clone M1323 may have an equilibrium dissociation constant ($K_D$) of $1.8 \times 10^{-8}$M or less, preferably, $1.8 \times 10^{-9}$M or less, and more preferably, $1.8 \times 10^{-10}$M or less, (2) the clone M1329 may have an equilibrium dissociation constant ($K_D$) of $3.5 \times 10^{-9}$M or less, preferably, $3.5 \times 10^{-10}$M or less, and more preferably, $3.5 \times 10^{-11}$M or less, (3) the clone M1403 may have an equilibrium dissociation constant ($K_D$) of $4.5 \times 10^{-8}$M or less, preferably, $4.5 \times 10^{-9}$M or less, and more preferably, $4.5 \times 10^{-10}$M or less, (4) the clone MS502 may have an equilibrium dissociation constant ($K_D$) of $2.3 \times 10^{-8}$M or less, preferably, $2.3 \times 10^{-9}$M or less, and more preferably, $2.3 \times 10^{-10}$M or less (see Table 8), (5) the clone C2G1 may have an equilibrium dissociation constant ($K_D$) of $9.39 \times 10^{-9}$M or less, preferably, $9.39 \times 10^{-10}$M or less, and more preferably, $9.39 \times 10^{-11}$M or less, (6) the clone C2G4 may have an equilibrium dissociation constant ($K_D$) of $4.32 \times 10^{-9}$M or less, preferably, $4.32 \times 10^{-10}$M or less, and more preferably, $4.32 \times 10^{-11}$M or less, (7) the clone C3C8 may have an equilibrium dissociation constant (KD) of $1.22 \times 10^{-8}$M or less, preferably, $1.22 \times 10^{-9}$M or less, and more preferably, $1.22 \times 10^{-10}$M or less (see Table 14), (8) the clone 56 may have an equilibrium dissociation constant ($K_D$) of $1.25 \times 10^{-8}$M or less, preferably, $1.25 \times 10^{-9}$M or less, and more preferably, $1.25 \times 10^{-10}$M or less, (9) the clone 2-30 may have an equilibrium dissociation constant ($K_D$) of $1.66 \times 10^{-8}$M or less, preferably, $1.66 \times 10^{-9}$M or less, and more preferably, $1.66 \times 10^{-10}$M or less,

(10) the clone 2-78 may have an equilibrium dissociation constant ($K_D$) of $1.63 \times 10^{-9}$M or less, preferably, $1.63 \times 10^{-10}$M or less, and more preferably, $1.63 \times 10^{-11}$M or less,

(11) the clone 56-C2G4 may have an equilibrium dissociation constant ($K_D$) of $1.63 \times 10^{-8}$M or less, preferably, $1.63 \times 10^{-9}$M or less, and more preferably, $1.63 \times 10^{-10}$M or less,

(12) the clone 2-30-C2G4 may have an equilibrium dissociation constant ($K_D$) of $2.34 \times 10^{-8}$M or less, preferably, $2.34 \times 10$-9M or less, and more preferably, $2.34 \times 10^{-10}$M or less,

(13) the clone 2-73-C2G4 may have an equilibrium dissociation constant ($K_D$) of $1.65 \times 10^{-8}$M or less, preferably, $1.65 \times 10^{-9}$M or less, and more preferably, $1.65 \times 10^{-10}$M or less, and

(14) the clone 2-78-C2G4 may have an equilibrium dissociation constant ($K_D$) of $3.72 \times 10^{-9}$M or less, preferably, $3.72 \times 10^{-10}$M or less, and more preferably, $3.72 \times 10^{-11}$M or less (see Table 18).

In another embodiment of the present invention, genes of the heavy chain variable region and the light chain variable region of a mouse derived from an immune library bound to human MSLN are identified, the heavy chain variable region gene is linked to a human immunoglobulin type 1 of heavy chain constant region (IgG1 heavy chain constant region) gene, and the light chain variable region gene is linked to a human kappa light chain constant region, and these genes are inserted into protein expression vectors for animal cell, respectively, to produce vectors, followed by transfection in the Expi293F™ cell lines and culturing to produce the antibody, and the produced antibody is purified by protein A to produce the antibody (Example 1-3).

In still another embodiment of the present invention, genes of the heavy chain variable region and the light chain variable region derived from a synthetic scFV library bound to human MSLN are identified, the heavy chain variable region gene is linked to a human immunoglobulin type 1 of heavy chain constant region (IgG1 heavy chain constant region) gene, and the light chain variable region gene is linked to a human kappa light chain constant region, and these genes are inserted into protein expression vectors for animal cell, respectively, to produce vectors, followed by transfection in the Expi293F™ cell lines and culturing to produce the antibody, and the antibody is purified by protein A to produce the antibody (Examples 2-4, 3-10, 3-12, and 3-13).

Therefore, in another aspect of the present invention, the present invention provides a nucleic acid encoding the antibody. The nucleic acid used herein may be present in a cell, a cell lysate, or may also be present in a partially purified form or a substantially pure form. The nucleic acid is "isolated" or "is substantially pure" when it is purified from other cell components or other contaminants, for example, other cell nucleic acid or protein by standard techniques including alkaline/SDS treatment, CsCl banding, column chromatography, agarose gel electrophoresis, and other techniques well-known in the art. The nucleic acid of the present invention may be, for example, DNA or RNA, and may include an intron sequence, or may not include the intron sequence.

In still another aspect of the present invention, the present invention provides a vector including the nucleic acid. For expression of the antibody or antibody fragments thereof, DNA encoding the light chain and the heavy chain having a partial length or a full length may be obtained by standard molecular biology techniques (for example, PCR amplification or cDNA cloning using a hybridoma that expresses a target antibody), and the DNA may be "operably bound" to transcription and translation control sequences to be inserted into the expression vector.

Term "operably bound" used herein may indicate that an antibody gene is ligated into the vector so that the transcription and translation control sequences in the vector have an intended function to control transcription and translation of the antibody gene. The expression vector and an expression control sequence are selected so as to have compatibility with a host cell for expression to be used. The light chain gene of the antibody and the heavy chain gene of the antibody are inserted into a separate vector, or both genes are inserted into the same expression vector. The antibody is inserted into the expression vector by a standard method (for example, ligation of an antibody gene fragment and a complementary restriction enzyme site on a vector or when the restriction enzyme site is not present at all, blunt end ligation). In some cases, the recombinant expression vector may encode a signal peptide that facilitates secretion of the antibody chain from the host cell. The antibody chain gene may be cloned into the vector so that the signal peptide is bound to an amino terminal of the antibody chain genes according to a frame. The signal peptide may be an immunoglobulin signal peptide or a heterologous signal peptide (i.e. signal peptide derived from proteins except for immunoglobulin). In addition, the recombinant expression vector has a regulatory sequence that controls the expression of the antibody chain genes in the host cell. The "regulatory sequence" may include a promoter, an enhancer and other expression control element (for example, polyadenylation signal) controlling the transcription or translation of the antibody chain gene. Those skilled in the art is able to recognize that design of the expression vector may vary by changing the regulatory sequences according to factors such as selection of the host cell to be transformed, an expression level of the protein, etc.

In still another aspect of the present invention, the present invention provides a host cell including the nucleic acid or the vector. The nucleic acid or the vector is transfected into the host cell. For the "transfection", various kinds of generally used techniques such as electrophoresis, calcium phosphate precipitation, DEAE-dextran transfection, lipofection, etc., may be used to introduce an exogenous nucleic acid (DNA or RNA) into a prokaryotic host cell or an eukaryotic host cell. The antibody according to the present invention may be expressed in an eukaryotic cell, preferably, in a mammalian host cell, in consideration of applicability into a mammalian cell. The mammalian host cells suitable for expression of the antibody may include a Chinese hamster ovary (CHO) cell (for example, including a dhfr– CHO cell used together with a DHFR selection marker), an NS0 myeloma cell, a COS cell, or a SP2 cell, etc., as examples.

In still another aspect of the present invention, the present invention provides a method for producing an antibody, including culturing a host cell to express the antibody. When the recombinant expression vector encoding the antibody gene is introduced into the mammalian host cell, the antibody may be produced by culturing the host cell for a sufficient period of time so that the antibody is expressed in the host cell, or more preferably, for a sufficient period of time so that the antibody is secreted into a culture medium in which the host cell is cultured.

In some cases, the expressed antibody may be separated from the host cell and purified for uniformity. The separation or the purification of the antibody may be performed by a separation method, a purification method generally used for protein, for example, chromatography. The chromatography may include, for example, affinity chromatography, ion exchange chromatography or hydrophobic chromatography including protein A column and protein G column. In addition to the chromatography, the antibody may be separated and purified by additionally combining with filtration, ultrafiltration, salting out, dialysis, etc.

In still another aspect of the present invention, the present invention provides a pharmaceutical composition for treating cancer or tumor including the antibody as an active ingredient.

Term "cancer" or "tumor" typically refers to or describes a physiological condition of mammals characterized by cell growth/proliferation that is not controlled. Examples of the cancer include carcinoma, lymphoma (e.g., Hodgkin's and non-Hodgkin's lymphoma), blastoma, sarcoma and leukemia, but are not limited thereto. More specific examples of the cancer include squamous cell cancer, small-cell lung cancer, non-small cell lung cancer, lung adenocarcinoma, lung squamous cell carcinoma, peritoneal cancer, hepatocellular cancer, gastrointestinal cancer, pancreatic cancer, glioma, cervical cancer, ovarian cancer, liver cancer, bladder cancer, hepatocellular cancer, breast cancer, colon cancer, colorectal cancer, endometrial or uterine carcinoma, salivary gland carcinoma, kidney cancer, liver cancer, prostate cancer, vulvar cancer, thyroid cancer, liver carcinoma, leukemia and other lymphoproliferative disorders, and various types of head and neck cancer. The cancer in the present invention is preferably mesothelin-positive cancer, and is selected from the group consisting of pancreatic cancer, ovarian cancer, lung cancer, stomach cancer, endometrial cancer, and mesothelioma.

The present invention provides a pharmaceutical composition including a therapeutically effective amount of anti-MSLN antibody and a pharmaceutically acceptable carrier. The "pharmaceutically acceptable carrier" is a material that is able to be added in the active ingredient to help formulation or stabilization of the preparation, and it does not cause significant adverse toxicological effects to patients.

The carrier refers to a carrier or diluent that does not inhibit biological activity and properties of an administered compound without stimulating the patients. The pharmaceutically acceptable carrier in the composition to be formulated as a liquid solution is sterilized and is suitable for a living body. Saline, sterile water, Ringer's solution, buffered saline, albumin injection solution, dextrose solution, maltodextrin solution, glycerol, ethanol may be used as the carrier, or at least one component thereof may be mixed to be used, and other conventional additives such as an antioxidant, buffer, a bacteriostatic agent, etc., may be added as needed. In addition, the composition may be prepared into formulations for injection, such as an aqueous solution, suspension, emulsion, etc., pill, a capsule, a granule or a tablet by further adding diluent, dispersant, surfactant, binder and lubricant thereto. Other carriers are described in, for example, [Remington's Pharmaceutical Sciences (E. W. Martin)]. The composition may contain the therapeutically effective amount of at least one anti-MSLN antibody.

The pharmaceutically acceptable carrier includes sterile aqueous solution or dispersion and sterile powder for preparing extemporaneous sterile injectable solution or dispersion. The use of such media and agents for pharmaceutical active materials is known in the art. The composition is preferably formulated for parenteral injection. The composition may be formulated as a solution, a micro-emulsion, a liposome, or other ordered structures suitable for high drug concentration. The carrier may be, for example, a solvent or dispersion medium containing water, ethanol, polyol (for example, glycerol, propylene glycol and liquid polyethylene glycol, etc.,) and suitable mixtures thereof. In some cases, the composition may include, isotonic agent, for example, sugar, polyalcohols such as mannitol, sorbitol, or sodium chloride. The sterile injectable solution may be prepared by incorporating a required amount of active compound into an appropriate solvent with one kind of the above-described components or a combination thereof, followed by sterile micro filtration as needed. In general, the dispersion is prepared by incorporating the active compound into a sterile vehicle containing basic dispersion medium and other required components from the above-described components. The sterile powder for preparing the sterile injectable solution is obtained by vacuum drying and freeze-drying (lyophilization) active ingredient powder and any additional desirable component powder from previously sterile-filtered solution.

The pharmaceutical composition may be administered orally or parenterally in the dosage and frequency that may vary depending on severity of suffering patients. The composition may be administered to a patient as a bolus or by continuous infusion as needed. For example, the bolus administration of the antibody of the present invention which is presented as a Fab fragment may have an amount of 0.0025 to 100 mg/kg body weight, 0.025 to 0.25 mg/kg, 0.010 to 0.10 mg/kg or 0.10 to 0.50 mg/kg. For the continuous infusion, the antibody of the present invention which is presented as the Fab fragment may be administered at 0.001 to 100 mg/kg kg/min, 0.0125 to 1.25 mg/kg/min, 0.010 to 0.75 mg/kg/min, 0.010 to 1.0 mg/kg/min or 0.10 to 0.50 mg/kg/min for 1 to 24 hours, 1 to 12 hours, 2 to 12 hours, 6 to 12 hours, 2 to 8 hours, or 1 to 2 hours. When the antibody of the present invention which is presented as a full-length antibody (having a complete constant region is administered, an administration amount may be about 1 to 10 mg/kg body weight, 2 to 8 mg/kg, or 5 to 6 mg/kg. The full-length antibody is typically administered via injection that lasts for 30 minutes to 35 minutes. An administration frequency depends on the severity of the condition. The frequency may be 3 times every week to once in a week or in two weeks.

In addition, the composition may be administered to a patient via a subcutaneous injection. For example, the anti-MSLN antibody having an administration amount of 10 to 100 mg may be weekly, biweekly, or monthly administered to a patient through subcutaneous injection.

As used herein, the "therapeutically effective amount" means an amount sufficient to treat diseases at a reasonable benefit/risk ratio applicable for medical treatment, and an amount of a combination of the anti-MSLN antibody. The exact amount may vary depending on a number of factors that include components and physical characteristics of a therapeutic composition, intended patient population, individual patient considerations, etc., but are not limited thereto, and may be easily determined by those skilled in the art. When completely considering these factors, it is important to administer the minimum amount sufficient to obtain the maximum effect without the side effect, and this dosage may be easily determined by an expert in the field.

The dosage of the pharmaceutical composition of the present invention is not specifically limited, but is changed according to various factors including a health state and weight, severity of the disease of a patient, and a drug type, an administration route, and administration time. The composition may be administered in routes that are typically allowed in mammals including rat, mouse, cattle, human, etc., for example, orally, rectally, intravenously, subcutaneously, intrauterinely or intracerebrovascularly in a single dose amount or multidose per day.

Example

Hereinafter, the present invention will be described in more detail with reference to the following Examples. However, the following examples are only for exemplifying the present invention, and it will be obvious to those skilled in the art that the scope of the present invention is not construed to be limited to these examples.

Example 1: Method for Producing Anti-MSLN Antibody from Immune Library

It is intended to produce an anti-cancer antibody therapeutic agent using an antibody against mesothelin (MSLN) over-expressed on a cancer cell surface.

1-1: Selection of Anti-MSLN Antibody

A mouse was immunized with a recombinant human MSLN and a spleen was removed to extract B lymphocyte. Total RNA was separated from the B lymphocyte and cDNA was synthesized. Various antibody genes of the mouse were cloned from the synthesized cDNA using polymerase chain reaction (PCR), and inserted into pComb3X phagemid to produce an antibody library displaying antibody fragments of various sequences. In order to find the antibody specifically bound to human MSLN from the antibody library, magnetic beads having the MSLN fixed thereto were mixed with the antibody library, and clones bound to a target antigen were separated and cultured. Then the clones (MI323, MI329, MI403, and MI407) specifically bound to the target antigen (human MSLN) were individually identified through an enzyme-linked immunosorbent assay (ELISA), and antibody gene sequences and amino acid sequence thereof were identified through base sequence analysis.

As a result, as shown in Table 1, the clones specifically bound to human MSLN could be selected, and amino acid sequences thereof were identified.

Table 2 shows CDR amino acid sequences of the clone antibodies of Table 1 on the basis of Kabat numbering.

TABLE 1

| Clone | Variable Region | Amino Acid Sequence | SEQ ID NO: |
|---|---|---|---|
| MI323 | heavy chain | EVQLQQSGPELVKPGTSVKISCKASGYSFTS YFIQWVKQRPGQGLEWIGWIFPGSGNTKYN EMFKGKATLAADTSSSTAYMQLSSLTSEDS AVYFCARSGGYQYYFDYWGQGTSVTVSS | 1 |
|  | light chain | DIVMTQSHKFMSTSVGDRVSITCKASQDVS TAVAWYQQKPGQSPKLLIYSASYRYPGVPD RFTGSGSGTDFTFTISSVQAEDLALYYCQQH YSTPWTFGGGTKLEIKR | 2 |
| MI329 | heavy chain | EVMLVESGGDLVKPGGSLKLSCAASGFTFS SYAMSWVRRTPEKRLEWVATINSDGSYTF YPDSVKGRFTISRDNAKNTLYLQMNSLRSE DTAMYYCARWGENWYFDVWGAGTTVTV SS | 3 |
|  | light chain | DVVMTQTPLSLPVSLGDQASISCRSSQSLVH SNGNTYLHWYLQKPGQSPKLLIYKVSNRFS GVPDRFSGSGSGTDFTLKISRVEAEDLGIYF CSQSTHFPRTFGGATKLELKR | 4 |
| MI403 | heavy chain | EVQVVESGGGLVKPGGSLKLSCAASGFAFS SYDMSWVRQTPEKRLEWVAYISSGGGSTY YPDTVKGRFTISRDNAKNTLYLQMNSLKSE DTAMYYCARQGTAVKNYWYFDVWGAGT SVTVSS | 5 |
|  | light chain | DIVMTQSPASLAVSLGQRATISCRASQSVST SSSSYVHWYQQRPGQPPKLLIKYASNLESG VPARFSGSGSGTDFTLNIHPVEEEDTGTYYC QHSWEIPFTFGSGTKLEIKR | 6 |
| MI407 | heavy chain | EVKLVESGGGLVKPGGSLKLSCAASGFPFS NYDMSWVRQTPEKRLEWVAYISSGGGNTY YPDTVKGRFTISRDNAKNTLYLQMSSLKSE DTALYFCVRQGTSVESYWYFDVWGAGTTV TVSS | 7 |
|  | light chain | DIVLTQSPASLAVSLGQRATISCRASQSVSTS SSSYIHWYQQKPGQPPKLLIKYASNLESGVP ARFSGSGSGTDFTLNIHPVEEDDTATYYCQ HSWEIPFTFGSGTELEIKR | 8 |

TABLE 2

| Clone | Variable Region | CDR1 | CDR2 | CDR3 |
|---|---|---|---|---|
| MI323 | heavy chain | SYFIQ (SEQ ID NO: 9) | WIFPGSGNTKY NEMFKG (SEQ ID NO: 10) | SGGYQYYFDY (SEQ ID NO: 11) |

TABLE 2-continued

| Clone | Variable Region | CDR1 | CDR2 | CDR3 |
|---|---|---|---|---|
| | light chain | KASQDVSTAVA (SEQ ID NO: 12) | SASYRYP (SEQ ID NO: 13) | QQHYSTPWT (SEQ ID NO: 14) |
| MI329 | heavy chain | SYAMS (SEQ ID NO: 15) | TINSDGSYTFYPDSVKG (SEQ ID NO: 16) | WGENWYFDV (SEQ ID NO: 17) |
| | light chain | RSSQSLVHSNGNTYLH (SEQ ID NO: 18) | KVSNRFS (SEQ ID NO: 19) | SQSTHFPRT (SEQ ID NO: 20) |
| MI403 | heavy chain | SYDMS (SEQ ID NO: 21) | YISSGGGSTYYPDTVKG (SEQ ID NO: 22) | QGTAVKNYWYFDV (SEQ ID NO: 23) |
| | light chain | RASQSVSTSSSSYVH (SEQ ID NO: 24) | YASNLES (SEQ ID NO: 25) | QHSWEIPFT (SEQ ID NO: 26) |
| MI407 | heavy chain | NYDMS (SEQ ID NO: 27) | YISSGGGNTYYPDTVKG (SEQ ID NO: 28) | QGTSVESYWYFDV (SEQ ID NO: 29) |
| | light chain | SVSTSSSSYIH (SEQ ID NO: 30) | YASNLES (SEQ ID NO: 25) | QHSWEIPFT (SEQ ID NO: 26) |

1-2: IgG Gene Cloning of MI323, MI329, MI403, and MI407 Monoclonal Antibodies

The pComb3X phagemid containing the genes encoding the heavy chain variable regions of the MI323, MI329, MI403, and MI407 clone antibodies was extracted, and used as a template for PCR with a forward primer containing NotI (Table 3: SEQ ID NOs: 31 to 34) and a reverse primer containing ApaI (Table 3: SEQ ID NO: 35) by using Accupower Pfu PCR premix (Bioneer). The PCR was performed by repeating exposure at 94° C. for 10 minutes, and then exposure at 94° C. for 15 seconds, at 56° C. for 30 seconds, and at 72° C. for 90 seconds 30 times, and reacting at 72° C. for 10 minutes. In the amplified genes, DNA bands having an expected size were confirmed on 1% agarose gel, and were separated using a gel extraction kit, respectively. Then, the separated genes reacted with NotI, ApaI restriction enzymes at 37° C. for 12 hours or more, and the genes reacted with the restriction enzymes were separated on 1% agarose gel again. A pcIW plasmid vector containing human immunoglobulin type 1 of heavy chain constant region (IgG1 heavy chain constant region) gene was also cut by the same method as above and separated on agarose gel. The separated MI323, MI329, MI403, and MI407 heavy chain variable region genes were inserted into NotI, ApaI sites of a linear pcIW vector containing the human heavy chain constant region by using a T4 DNA ligase (Cat.No.M0203S, New England BioLabs (NEB)). The ligation reaction materials were transformed into XL1-Blue bacteria (Electroporation-Competent Cells; Cat.No. 200228, Stratagene), plated on an LB plate (Cat.No.LN004CA, NaraeBiotech) containing carbenicillin, and cultured at 37° C. for 12 hours or more. Then single colonies were chosen and cultured, and plasmids were separated by using a plasmid mini kit (Cat.No. 27405, QIAGEN), and confirmed by DNA sequencing.

The pComb3X phagemid containing the genes encoding the light chain variable regions of the MI323, MI329, MI403, and MI407 clone antibodies was extracted, and used as a template for PCR of the light chain variable regions of the MI323, MI329, MI403, and MI407 clone antibodies, wherein the PCR was performed with a forward primer containing NotI (Table 3: SEQ ID NO: 36, 38, 40, 42) and a reverse primer (Table 3: SEQ ID NO: 37, 39, 41, 43) by using Accupower Pfu PCR premix. Further, the human antibody kappa light chain constant region was subjected to PCR with a forward primer (Table 3: SEQ ID NO: 44) and a reverse primer containing HindIII (Table 3: SEQ ID NO: 45). The PCR was performed by repeating exposure at 94° C. for 10 minutes, and then exposure at 94° C. for 15 seconds, at 56° C. for 30 seconds, and at 72° C. for 90 seconds 30 times, and reacting at 72° C. for 10 minutes. In the amplified genes, DNA bands having a predicted size were confirmed on 1% agarose gel, and were separated using a gel extraction kit, respectively. Then, the respective light chain variable regions and light chain constant regions were mixed, followed by overlapping PCR, such that the genes expressing the light chain region were cloned. The PCR was performed by repeating exposure at 94° C. for 10 minutes, and then exposure at 94° C. for 15 seconds, at 56° C. for 30 seconds, and at 72° C. for 90 seconds 30 times, and reacting at 72° C. for 10 minutes. In the amplified genes, DNA bands having an expected size were confirmed on 1% agarose gel, and were separated using a gel extraction kit, respectively. Then, the separated genes reacted with NotI, HindIII restriction enzymes at 37° C. for 12 hours or more, and the genes reacted with the restriction enzymes were separated on 1% agarose gel again. The pcIW plasmid vector was also cut by the same method as above and separated on agarose gel. The separated MI323, MI329, MI403, and MI407 light chain region genes were inserted into NotI, HindIII sites of a linear pcIW vector by using a T4 DNA ligase (Cat.No.M0203S, New England BioLabs (NEB)). The ligation reaction materials were transformed into XL1-Blue bacteria (Electroporation-Competent Cells; Cat.No. 200228, Stratagene), plated on an LB plate (Cat.No.LN004CA, NaraeBiotech) containing carbenicillin, and cultured at 37° C. for 12 hours or more. Then single colonies were chosen and cultured, and plasmids were separated by using a plasmid mini kit (Cat.No. 27405, QIAGEN), and confirmed by DNA sequencing.

TABLE 3

| Name | DNA nucleotide sequence | SEQ ID NO: |
|---|---|---|
| MI323VH-F | GCGGCCGCCATGTACTTGGGACTGAACTATGTATTC ATAGTTTTTCTCTTAAATGGTGTCCAGAGTGAGGTC CAGCTGCAGCAGTCT | 31 |
| MI329VH-F | GCGGCCGCCATGTACTTGGGACTGAACTATGTATTC ATAGTTTTTCTCTTAAATGGTGTCCAGAGTGAGGTG ATGCTGGTGGAGTCT | 32 |
| MI403VH-F | GCGGCCGCCATGTACTTGGGACTGAACTATGTATTC ATAGTTTTTCTCTTAAATGGTGTCCAGAGTGAGGTG CAGGTGGTGGAGTCT | 33 |
| MI407VH-F | GCGGCCGCCATGTACTTGGGACTGAACTATGTATTC ATAGTTTTTCTCTTAAATGGTGTCCAGAGTGAGGTG AAGTTGGTGGAGTCT | 34 |
| VHApaI-R | ACCGATGGGCCCTTGGTGGA | 35 |
| MI323VL-F | GCGGCCGCCATGGATAGCCAGGCTCAGGTGCTGATG CTGCTGCTGCTGTGGGTGTCAGGGACTTGCGGGAC ATTGTGATGACCCAGTCTCACAAA | 36 |
| MI323VLCL-R | ACACTAGGAGCGGCCACGGTTCGTTTGATTTCCAGT TTGGTCCCT | 37 |
| MI329VL-F | GCGGCCGCCATGGATAGCCAGGCTCAGGTGCTGATG CTGCTGCTGCTGTGGGTGTCAGGGACTTGCGGGAC GTTGTGATGACCCAGACTCCACTC | 38 |
| MI329VLCL-R | ACACTAGGAGCGGCCACGGTTCGTTTCAGCTCCAGC TTGGTC | 39 |
| MI403VL-F | GCGGCCGCCATGGATAGCCAGGCTCAGGTGCTGATG CTGCTGCTGCTGTGGGTGTCAGGGACTTGCGGGGAT ATTGTGATGACCCAGTCTCCTGCT | 40 |
| MI403VLCL-R | ACACTAGGAGCGGCCACGGTTCGTTTTATTTCCAAC TTTGTCCCCGA | 41 |
| MI407VL-F | GCGGCCGCCATGGATAGCCAGGCTCAGGTGCTGATG CTGCTGCTGTGTGGGTGTCAGGGACTTGCGGGGAT ATTGTGTTGACACAGTCTCCTGCT | 42 |
| MI407VLCL-R | ACACTAGGAGCGGCCACGGTTCGTTTTATTTCCAAC TCTGTCCCCG | 43 |
| Ck-F | ACCGTGGCCGCTCCTAGTGT | 44 |
| CkSHB-R | NNNNGGATCCAAGCTTACTAGCACTCCCC | 45 |

1-3: Production and Purification of IgG of MI323, MI329, MI403, and MI407 Clone Antibodies In order to produce and purify the anti-MSLN antibody MI323, MI329, MI403, and MI407 clones obtained by a mouse immune response, Expi293F™ cells were inoculated at a concentration of 2.0×10⁶ cell/mL the day before transfection. After incubation (37° C., 8% $CO_2$, 125 rpm) for 24 hours, Expi293™ expression medium (Cat.No.A1435101, Gibco) was added to prepare a product of 30 mL having a concentration of 2.5×10⁶ cell/mL (viability=95%). 30 μg of DNA (pcIW-anti-MSLN heavy chain: 15 μg, pcIW-anti-MSLN light chain: 15 μg) was diluted in an OptiPro™ SEM medium (Cat.No. 12309019, Gibco) so as to have a total volume of 1.5 mL, and reacted at room temperature for 5 minutes. 1.5 mL of the OptiPro™ SEM medium (Cat.No. 12309019, Gibco) was mixed with 80 μL of an ExpiFectamine™ 293 reagent (Cat.No.A14524, Gibco) so that a total volume is 1.5 mL, and reacted at room temperature for 5 minutes. After the reaction for 5 minutes, 1.5 mL of diluted DNA and 1.5 mL of diluted ExpiFectamine™ 293 reagent were well-mixed with each other, and reacted at room temperature for 20 to 30 minutes. 3 mL of the mixture of DNA and ExpiFectamine™ 293 reagent was treated in the Expi293F™ cells. After suspension-culture (37° C., 8% $CO_2$, 125 rpm) for 16 to 18 hours, 150 μL of ExpiFectamine™ 293 Enhancer 1 (Cat.No.A14524, Gibco) and 1.5 mL of ExpiFectamine™ 293 Enhancer 2 (Cat.No.A14524, Gibco) were added thereto, followed by suspension-culturing for 5 days. After the culturing, cell debris was removed by centrifugation at 4000 rpm for 20 minutes, and the supernatant passed through 0.22 μm filter to be prepared. MabSelect Xtra (Cat.No. 17-5269-02, GE Healthcare) which is protein A resin having 100 μL was prepared for each 30 mL of the culture fluid, followed by centrifugation at 1000 rpm for 2 minutes to remove a storage solution, and the obtained product was washed with 400 μL of protein A binding buffer (Cat.No. 21007, Pierce) 3 times. The protein A resin was added to the prepared culture fluid and rotation-reacted at room temperature for 30 minutes. The mixture of the culture fluid and the resin was put into a pierce spin column snap-cap (Cat.No. 69725, Thermo), and then, only the resin was left in the column using QIAvac 24 Plus (Cat.No. 19413, QIAGEN) vacuum manifold. 5 mL of protein A binding buffer was added to wash the resin, 200 μL of a protein A elution buffer (Cat.No. 21009, Pierce) was added thereto. The resultant material was reacted by resuspension at room temperature for 2 minutes, and centrifuged at 1000 rpm for 1 minute, and eluted. Each eluate was neutralized by adding 2.5 μL of 1.5M Tris-HCl (pH 9.0). The elution was performed 4 to 6 times, and each fraction was quantified by using Nanodrop 200C (Thermo Scientific). The fractions in which protein is detected were collected, and exchanged with a PBS (Phosphate-Buffered Saline) buffer using Zeba Spin Desalting Columns, 7K MWCO, 5 mL (Cat.No. 0089892, Pierce). Then, protein electrophoresis (SDS-PAGE) was performed under reduction and non-reduction condition to finally verify the concentration quantification and the antibody state, and the antibody was kept at 4° C.

Example 2: Method for Producing Anti-MSLN Antibody from Phage Display Synthetic scFv Library 2-1: Selection of Anti-Human MSLN scFv Antibody Using Phage Display For a primary panning, 1 mL of 10¹³ or more library stock was reacted in a solid phase polystyrene tube (Cat.No. 444202, Nunc) coated with MSLN at 37° C. for 2 hours. At the same time, 10 μL of XL1-Blue bacteria (electroporation-competent cells; Cat.No. 200228, Stratagene) were inoculated with 10 μL of SB 10 ml/tetracycline and grown to an $OD_{600}$ of 0.8 to 1.0. The library stock obtained after reaction at 37° C. for 2 hours was washed with 5 ml of 0.05% Tween 20/PBS four times, and from a secondary panning, the number of times of washing with 0.05% Tween 20/PBS increased according to an increase in the number of times of panning. Then, the resultant material was cultured with 1% BSA/0.1M Glycine pH 2.0 at room temperature for 10 minutes to purify the phagemid. The purified phagemid was transferred to a 50 mL tube and neutralized with 70 μL of 2M Tris. 9 mL of XL1-Blue bacteria (electroporation-competent cells; Cat.No. 200228, Stratagene) were treated, and 1 mL of the bacteria were treated in a washed tube. The bacteria were infected at room temperature for 30 minutes, and 10 mL of SB, 20 μL of tetracycline, 10 μL of carbenicillin were added thereto, followed by suspension-culturing at 37° C. and 220 rpm for 1 hour. Then, the bacteria were treated with 1 mL of VCS M13 helper phage ($10^{11}$ pfu), and suspension-cultured at 37° C. and at 220 rpm for 1 hour, and treated with 80 mL of SB, 100 μL of kanamycin, and 100 μL of carbenicillin, and cultured at 37° C. and at 220 rpm for 12 hours or more. The bacteria cultured over 12 hours were centrifuged at 3500 rpm and at 4° C. for 10 minutes, and the supernatant was transferred to a new tube. 20 mL of 20% PEG/15% NaCl was added thereto, well-mixed, and reacted in ice for 30 minutes. Then, the supernatant was discarded, and pellets were collected and re-suspended with 2 mL of 1% BSA/PBS at 8000 rpm, and at 4° C. for 30 minutes, and centrifuged at 15000 rpm and 4° C. for 10 minutes. Here, the collected pellets were discarded and 1 mL of the supernatant (2 mL) was stored at −20° C. and the remainder (1 mL) was used in the following order panning.

2-2: Securing Individual Clones According to ELISA

Single colonies of a phage display synthetic scFv library final amplified population were collected, and cultured with 1.5 mL of SB/carbenicillin to an $OD_{600}$ of 0.8 to 1.0 at 37° C. and at 220 rpm, and then cultured with 1 mM IPTG at 30° C. and at 200 rpm for 12 hours or more. The reaction materials were centrifuged at 5500 rpm for 5 minutes, and only each supernatant was added to ELISA plates containing underlying MSLN antigen, and reacted at room temperature for 2 hours. Then, the resultant materials were washed with PBST (1×PBS, 0.05% tween 20) four times, and HRP/Anti-hFab-HRP conjugate diluted by 1/5000 with 1% BSA/1× PBS was added thereto, and reacted at room temperature for 1 hour, and washed with PBST (1×PBS, 0.05% tween 20) 4 times. Then, a TMB solution was added thereto and reacted for 5 to 10 minutes, and a TMB stop solution was added thereto. Next, O.D values were measured at a measurement wavelength of 450 nm using a TECAN sunrise, and clones having high O.D. value were secured as individual clones.

As a result, as shown in Table 4, the clones specifically bound to the human MSLN were able to be selected, and amino acid sequences thereof were identified.

Table 5 shows CDR amino acid sequences of the clone antibodies of Table 4 on the basis of Kabat numbering.

TABLE 4

| Clone | variable region | amino acid sequence | SEQ ID NO: |
|---|---|---|---|
| MS501 | heavy chain | EVQLLESGGGLVQPGGSLRLSCAASGFT FSNYAMSWVRQAPGKGLEWVSGIYPDS GSTYYADSVKGRFTISRDNSKNTLYLQM NSLRAEDTAVYYCARNIYTFDYWGQGT LVTVSS | 46 |
|  | light chain | QSVLTQPPSASGTPGQRVTISCSGSSSNIG SNAVSWYQQLPGTAPKLLIYYNNQRPSG VPDRFSGSKSGTSASLAISGLRSEDEADY YCGSWDSSLSGYVFGGGTKLTVLG | 47 |
| MS502 | heavy chain | EVQLLESGGGLVQPGGSLRLSCAASGFT FSNYAMSWVRQAPGKGLEWVSGIPPDS GSKYYADSVRGRFTVSRDNSKNTLYLQ MNSLRAEDTAVYYCAKNMLSFDYWGQ GTLVTVSS | 48 |
|  | light chain | QSVLTQPPSASGTPGQRVTISCTGSSSNIG SNAVSWYQQLPGTAPKLLIYYNSKRPSG VPDRFSGSKSGTSASLAISGLRSEDEADY YCGSWDSSLNGYVFGGGTKVTVLG | 49 |
| MS502-1 | heavy chain | EVQLLESGGGLVQPGGSLRLSCAASGFT FSNYAMSWVRQAPGKGLEWVSGIPPDS GSKYYADSVRGRFTVSRDNSKNTLYLQ MNSLRAEDTAVYYCAKNMLSFDYWGQ GTLVTVSS | 48 |
|  | light chain | QSVLTQPPSASGTPGQRVTISCICSSSNIG SNAVSWYQQLPGTAPKLLIYYNSKRPSG VPDRFSGSKSGTSASLAISGLRSEDEADY YCGSWDSSLNGYVFGGGTKLTVLG | 50 |
| MS503 | heavy chain | EVQLLESGGGLVQPGGSLRLSCAASGFT FSNYAMSWVRQAPGKGLEWVSSIYPGD GSTYYADSVKGRFTISRDNSKNTLYLQM NSLRAEDTAVYYCAKNAFTFDYWGQGT LVTVSS | 51 |
|  | light chain | QSVLTQPPSASGTPGQRVTISCSGSSSNIG SNAVSWYQQLPGTAPKLLIYYNSHRPSG VPDRFSGSKSGTSASLAISGLRSEDEADY YCGTWDSSLSGYVFGGGTKLTVLG | 52 |
| MS504 | heavy chain | EVQLLESGGGLVQPGGSLRLSCAASGFT FSNYAMSWVRQAPGKGLEWVSSIYPNG SSKYYADSVKGRFTISRDNSKNTLYLQM NSLRAEDMAVYYCAKNLLTFDYWGQG TLVTVSS | 53 |
|  | light chain | QSVLTQPPSASGPPGQRVTISCTGSSSNIG NNSVSWYQQLPGTAPKLLIYYDSHRPSG VPDRFSGSKSGTSASLAIGGLRSEDEADY YCGAWDDSLNAYVFGGGTKLTVLG | 54 |

TABLE 4-continued

| Clone | variable region | amino acid sequence | SEQ ID NO: |
|---|---|---|---|
| MS505 | heavy chain | EVQLLESGGGLVQPGGSLRLSCAASGFT FSNYAMSWVRQAPGKGLEWVSAIYPDG SNKYYADSVKGRFTVSRDNSKNTLYLQ MNSLRAEDTAVYYCARNAYTFDYWGQ GTLVTVSS | 55 |
| | light chain | QSVLTQPPSASGTPGRRVTISCSGSSSNIG SNAVSWYQQLPGTAPKLLIYYNSQRPSG VPDRFSGSKSGTSASLAISGLRSEDEADY YCGSWDSSLNGYVFGGGTKLTVLG | 56 |
| MS506 | heavy chain | EVQLLESGGGLVQPGGSLRLSCAASGFT FSNYAMSWVRQAPGKGLEWVSSIYPGS GSTYYADSVKGRFTISRDNSKNTLYLQM NSLRAEDTAVYYCARNLYTFDYWGQGT LVTVSS | 57 |
| | light chain | QSVLTQPPSASGTPGQRVTISCTGSSSNIG SNAVTWYQQLPGTAPKLLIYYDSHRPSG VPDRFSGSKSGTSASLAISGPRSEDEADY YCGAWDSSLSAYVFGGGTKLTVLG | 58 |

TABLE 5

| Clone | variable region | CDR1 | CDR2 | CDR3 |
|---|---|---|---|---|
| MS501 | heavy chain | NYAMS (SEQ ID NO: 59) | GIYPDSGSTYYA DSVKG (SEQ ID NO: 60) | NIYTFDY (SEQ ID NO: 61) |
| | light chain | SGSSSNIGSNA VS (SEQ ID NO: 62) | YNNQRPS (SEQ ID NO: 63) | GSWDSSLSGYV (SEQ ID NO: 64) |
| MS502 | heavy chain | NYAMS (SEQ ID NO: 59) | GIPPDSGSKYYA DSVRG (SEQ ID NO: 65) | NMLSFDY (SEQ ID NO: 66) |
| | light chain | TGSSSNIGSNA VS (SEQ ID NO: 67) | YNSKRPS (SEQ ID NO: 68) | GSWDSSLNGYV (SEQ ID NO: 69) |
| MS502-1 | heavy chain | NYAMS (SEQ ID NO: 59) | GIPPDSGSKYYA DSVRG (SEQ ID NO: 65) | NMLSFDY (SEQ ID NO: 66) |
| | light chain | ICSSSNIGSNA VS (SEQ ID NO: 70) | YNSKRPS (SEQ ID NO: 68) | GSWDSSLNGYV (SEQ ID NO: 69) |
| MS503 | heavy chain | NYAMS (SEQ ID NO: 59) | SIYPGDGSTYYA DSVKG (SEQ ID NO: 71) | NAFTFDY (SEQ ID NO: 72) |
| | light chain | SGSSSNIGSNA VS (SEQ ID NO: 62) | YNSHRPS (SEQ ID NO: 73) | GTWDSSLSGYV (SEQ ID NO: 74) |
| MS504 | heavy chain | NYAMS (SEQ ID NO: 59) | SIYPNGSSKYYA DSVKG (SEQ ID NO: 75) | NLLTFDY (SEQ ID NO: 76) |
| | light chain | TGSSSNIGNNS VS (SEQ ID NO: 77) | YDSHRPS (SEQ ID NO: 78) | GAWDDSLNAYV (SEQ ID NO: 79) |
| MS505 | heavy chain | NYAMS (SEQ ID NO: 59) | AIYPDGSNKYYA DSVKG (SEQ ID NO: 80) | NAYTFDY (SEQ ID NO: 81) |
| | light chain | SGSSSNIGSNA VS (SEQ ID NO: 62) | YNSQRPS (SEQ ID NO: 82) | GSWDSSLNGYV (SEQ ID NO: 83) |

TABLE 5-continued

| Clone | variable region | CDR1 | CDR2 | CDR3 |
|---|---|---|---|---|
| MS506 | heavy chain | NYAMS (SEQ ID NO: 59) | SIYPGSGSTYYA DSVKG (SEQ ID NO: 84) | NLYTFDY (SEQ ID NO: 85) |
|  | light chain | TGSSSNIGSNA VT (SEQ ID NO: 86) | YDSHRPS (SEQ ID NO: 78) | GAWDSSLSAYV (SEQ ID NO: 87) |

2-3: IgG Gene Cloning of Anti-Mesothelin Antibody

The pComb3X phagemid containing the genes encoding the light chain variable regions of the secured MS501, MS502, MS503, MS504, MS505, and MS506 clone antibodies was extracted, and used as a template for PCR of the light chain variable regions of the MS501, MS502, MS503, MS504, MS505, and MS506 clone antibodies, wherein the PCR was performed with a forward primer containing NotI (SEQ ID NO: 86) and a reverse primer (SEQ ID NO: 87) by using Accupower Pfu PCR premix. Further, human antibody kappa light chain constant region was subjected to PCR with a forward primer (Table 6: SEQ ID NO: 88) and a reverse primer (Table 6: SEQ ID NO: 89). The PCR was performed by repeating exposure at 94° C. for 10 minutes, and then exposure at 94° C. for 15 seconds, at 56° C. for 30 seconds, and at 72° C. for 90 seconds 30 times, and reacting at 72° C. for 10 minutes. In the amplified genes, DNA bands having an expected size were confirmed on 1% agarose gel, and were separated using a gel extraction kit, respectively. Then, the respective light chain variable regions and light chain constant regions were mixed, followed by overlapping PCR, such that the genes expressing the light chain region were cloned. The PCR was performed by repeating exposure at 94° C. for 10 minutes, and then exposure at 94° C. for 15 seconds, at 56° C. for 30 seconds, and at 72° C. for 90 seconds 30 times, and reacting at 72° C. for 10 minutes. In the amplified genes, DNA bands having an expected size were confirmed on 1% agarose gel, and were separated using a gel extraction kit, respectively. Then, the separated genes reacted with NotI, HindIII restriction enzymes at 37° C. for 12 hours or more, and the genes reacted with the restriction enzymes were separated on 1% agarose gel again. The pcIW plasmid vector was also cut by the same method as above and separated on agarose gel. The separated MS501, MS502, MS503, MS504, MS505, MS506 light chain region genes were inserted into NotI, HindIII sites of the linear pcIW vector by using a T4 DNA ligase (Cat.No.M0203S, New England BioLabs (NEB)). The ligation reaction materials were transformed into XL1-Blue bacteria (Electroporation-Competent Cells; Cat.No. 200228, Stratagene), plated on an LB plate (Cat.No.LN004CA, NaraeBiotech) containing carbenicillin, and cultured at 37° C. for 12 hours or more. Then single colonies were chosen and cultured, and plasmids were separated by using a plasmid mini kit (Cat.No. 27405, QIAGEN), and confirmed by DNA sequencing.

The pComb3X phagemid containing the genes encoding the heavy chain variable regions of the MS501, MS502, MS503, MS504, MS505, and MS506 clone antibodies was extracted, and used as a template for PCR with a forward primer containing NotI (Table 6: SEQ ID NO: 90) and a reverse primer containing ApaI (Table 6: SEQ ID NO: 91) by using Accupower Pfu PCR premix (Bioneer). The PCR was performed by repeating exposure at 94° C. for 10 minutes, and then exposure at 94° C. for 15 seconds, at 56° C. for 30 seconds, and at 72° C. for 90 seconds 30 times, and reacting at 72° C. for 10 minutes. In the amplified genes, DNA bands having an expected size were confirmed on 1% agarose gel, and were separated using a gel extraction kit, respectively. Then, the separated genes reacted with NotI, ApaI restriction enzymes at 37° C. for 12 hours or more, and the genes reacted with the restriction enzymes were separated on 1% agarose gel again. A pcIW plasmid vector containing human immunoglobulin type 1 of heavy chain constant region (IgG1 heavy chain constant region) gene was also cut by the same method as above and separated on agarose gel. The separated MS501, MS502, MS503, MS504, MS505, and MS506 heavy chain variable region genes were inserted into NotI, ApaI sites of the linear pcIW vector containing the human heavy chain constant region by using a T4 DNA ligase (Cat.No.M0203S, New England BioLabs (NEB)). The ligation reaction materials were transformed into XL1-Blue bacteria (Electroporation-Competent Cells; Cat.No. 200228, Stratagene), plated on an LB plate (Cat.No.LN004CA, NaraeBiotech) containing carbenicillin, and cultured at 37° C. for 12 hours or more. Then single colonies were chosen and cultured, and plasmids were separated by using a plasmid mini kit (Cat.No. 27405, QIAGEN), and confirmed by DNA sequencing.

TABLE 6

| Name | Nucleotide sequence | SEQ ID NO: |
|---|---|---|
| NotI-Leader-VL-F | NNNNGCGGCCGCCATGGATAGCCAGGCTCAG GTGCTGATGCTGCTGCTGCTGTGGGTGTCAGG GACTTG CGGGCAGTCTGTGCTGACTCAGCCA | 88 |
| VL-R | GGGGTTGGCCTTGGGCTGGCCTAGGACCGTC AGCTTGGT | 89 |
| VL-CL-F | CAGCCCAAGGCCAACCCC | 90 |
| HindIII-VL-R | NNNNGGATCCAAGCTTACTAACATTCTGTAG GGGCCACTGTC | 91 |
| HD-Heavy-F | GGTGTCCAGGCGGCCGCCATGTACTTGGGAC TGAACTATGTATTCATAGTTTTTCTCTTAAAT GGTGTCCAGAGTGAGGTGCAGCTGTTGGAGT CTG | 92 |
| HD-Heavy-R | GGGGGAAGACCGATGGGCCCTTGGTGGAGGC TGAGCTCACGGTGACCAGTGT | 93 |

2-4: Production and Purification of IgG of MS501, MS502, MS503, MS504, MS505, MS506 Clone Antibodies In order to produce and purify the MS501, MS502, MS503, MS504, MS505, MS506 clone antibodies obtained from the phage display scFv library, Expi293F™ cells were inoculated at a concentration of $2.5 \times 10^6$ cell/mL the day before transfection. After incubation (37° C., 8% $CO_2$, 125 rpm) for 24 hours, Expi293™ expression medium (Cat-.No.A1435101, Gibco) was added to prepare a product of 30 mL having a concentration of 2.5×10⁶ cell/mL (viability=95%). 30 μg of DNA (pcIw-MS502 heavy chain variable region: 15 μg, pcIw-anti-Mesothelin light chain variable region: 15 μg) was diluted in an OptiPro™ SEM medium (Cat.No. 12309019, Gibco) so as to have a total volume of 1.5 mL, and reacted at room temperature for 5 minutes. 1.5 mL of the OptiPro™ SEM medium (Cat.No. 12309019, Gibco) was mixed with 80 μL of an ExpiFectamine™ 293 reagent (Cat.No.A14524, Gibco) so that a total volume is 1.5 mL, and reacted at room temperature for 5 minutes. After the reaction for 5 minutes, 1.5 mL of diluted DNA and 1.5 mL of diluted ExpiFectamine™ 293 reagent were well-mixed with each other, and reacted at room temperature for 20 to 30 minutes. 3 mL of the mixture of DNA and ExpiFectamine™ 293 reagent was treated in the Expi293F™ cells. After suspension-culture (37° C., 8% $CO_2$, 125 rpm) for 16 to 18 hours, 150 μL of ExpiFectamine™ 293 Enhancer 1(Cat.No.A14524, Gibco) and 1.5 mL of ExpiFectamine™ 293 Enhancer2 (Cat.No.A14524, Gibco) were added thereto, followed by suspension-culturing for 5 days. After the culturing, cell debris was removed by centrifugation at 4000 rpm for 20 minutes, and the supernatant passed through 0.22 μm filter to be prepared. MabSelect Xtra (Cat.No. 17-5269-02, GE Healthcare) which is protein A resin having 100 μL was prepared for each 30 mL of the culture fluid, followed by centrifugation at 1000 rpm for 2 minutes to remove a storage solution, and the product was washed with 400 μL of protein A binding buffer (Cat.No. 21007, Pierce) 3 times. The protein A resin was added to the prepared culture fluid and rotation-reacted at room temperature for 30 minutes. The mixture of the culture fluid and the resin was put into a pierce spin column snap-cap (Cat.No. 69725, Thermo), and then, only the resin was left in the column using QIAvac 24 Plus (Cat.No. 19413, QIAGEN) vacuum manifold. 5 mL of protein A binding buffer was added to wash the resin, 200 μL of a protein A elution buffer (Cat.No. 21009, Pierce) was added thereto. The resultant material was reacted by resuspension at room temperature for 2 minutes, and centrifuged at 1000 rpm for 1 minute, and eluted. Each eluate was neutralized by adding 2.5 μL of 1.5M Tris-HCl (pH 9.0). The elution was performed 4 to 6 times, and each fraction was quantified by using Nanodrop 200C (Thermo scientific). The fractions in which protein is detected were collected, and exchanged with a PBS (Phosphate-Buffered Saline) buffer using Zeba Spin Desalting Columns, 7K MWCO, 5 mL (Cat.No. 0089892, Pierce). Then, protein electrophoresis (SDS-PAGE) was performed under reduction and non-reduction condition to finally verify the concentration quantification and the antibody state, and the antibody was kept at 4° C.

2-5: Measurement of Quantitative Binding Force of Anti-MSLN Antibody with Regard to Antigen Quantitative binding force (affinity) of the purified anti-MSLN antibodies, i.e., MI323, MI329, MI403, MS502 clone antibodies with regard to recombinant human mesothelin (MSLN) was measured by using a Biacore T-200 (GE Healthcare, U.S.A.) biosensor. The MSLN (Cat.No. 3265-MS, R&D systems) purified from the HEK293 cells was fixed to a CMS chip (GE Healthcare, U.S.A.) so as to satisfy 200 Rmax by using an amine-carboxylic reaction. Then, the clone C2G1 antibody, the clone C2G4 antibody or the clone C3C8 antibody serially diluted with HBS-EP buffer (10 mM HEPES, pH7.4, 150 mM NaCl, 3 mM EDTA, 0.005% surfactant P20) was allowed to flow at a concentration range of 0.078 nM to 5 nM and at a flow rate of 30 μL/min for association of 120 seconds and dissociation of 1800 seconds. The dissociation of the antibody bound to the MSLN was induced by flowing 10 mM Glycine-HCl pH 1.5 at a flow rate of 30 μL/min for 30 seconds (Table 7). The affinity was obtained as movement speed constants ($K_{on}$ and $K_{off}$) and an equilibrium dissociation constant ($K_D$) by using a Biacore T-200 evaluation software (Table 8).

TABLE 7

| | |
|---|---|
| SPR | Biacore T200 |
| Chip | CM5 |
| Running Buffer | HBS-EP pH 7.4 |
| Flow rate | 30 μL/min |
| Association/dissociation time | 120 sec/600 sec |
| IgG Conc. | 0.078~5 nM, ½ serial dilution |
| Regeneration | 10 mM Glycine-HCl pH 1.5, 30 sec |

TABLE 8

| | $K_{on}$ | $K_{off}$ | $K_D$ |
|---|---|---|---|
| MI323 | $2.7 \times 10^5$ | $4.8 \times 10^{-5}$ | $1.8 \times 10^{-10}$ |
| MI329 | $1.4 \times 10^6$ | $5.1 \times 10^{-5}$ | $3.5 \times 10^{-11}$ |
| MI403 | $8.9 \times 10^4$ | $4.0 \times 10^{-5}$ | $4.5 \times 10^{-10}$ |
| MS502 | $1.9 \times 10^7$ | $4.3 \times 10^{-3}$ | $2.3 \times 10^{-10}$ |

Figure 1:
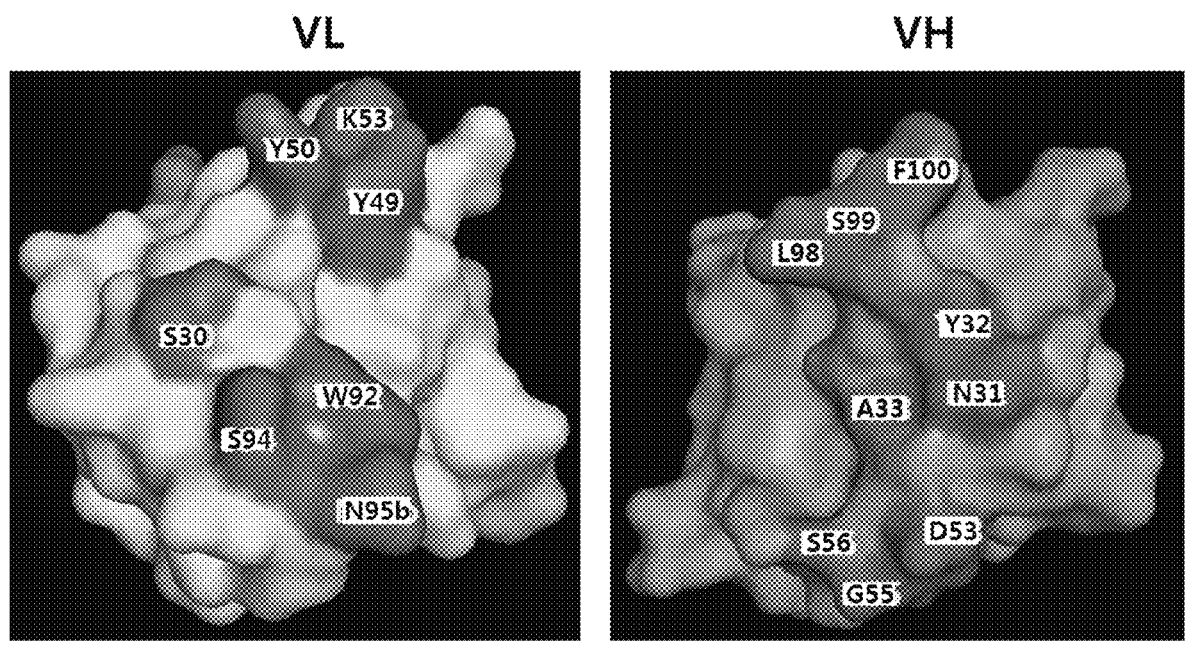
FIG. 1 illustrates prediction structures of a light chain variable region (VL) and a heavy chain variable region (VH) of clone MS502 among anti-mesothelin (MSLN) antibodies.

Example 3: Method for Producing MS502 Clone Affinity Maturation Antibody 3-1: Design of MS502 Clone Affinity Maturation Library The amino acid sequence of the anti-mesothelin MS502 clone was entered to the Swiss model homepage (http://swissmodel.expasy.org/) to find a template sequence. 50 sequences were found on the basis of homologous sequences, and modeling was performed by designating each sequence as the template. 50 sequences were listed by priority on the basis of QMEAN4 values (Cβ, all atom, solvation, torsion), and the template was selected in consideration of sequence identity and resolution in addition to the QMEAN4 values. 3g6a.1.B was selected for the heavy chain variable region, and 3qhz.1.B (LCDR1,2) and 4o51.1.A (LCDR3) were selected for the light chain variable region. The MS502 structure obtained on the basis of the selected template was analyzed by pymol program, and paratope was selected on the basis of the protruding amino acid of the CDR (see FIG. 1). Among them, VL CDR2 Y49, Y50, K53 were excluded from the mutation candidate amino acids even though it was anticipated that they are paratopes since Tyr and Lys are amino acids generally having a positive effect on bonding. The introduction of mutation was designed by 50% preserving the existing sequence, increasing Tyr, Ser, Gly rates, and controlling the nucleotide sequence using a handmix primer (IDT, U.S.A.) so that hydrophilic, hydrophobic, positive charge, and negative charge rates were uniformly included (Table 9). The heavy chain variable region was divided into each of three fragments since the mutation was introduced into all of CDR1, 2, and 3, and they were subjected to fragment PCR and overlapping PCR to construct a library, and the light chain variable region was divided into each of two fragments since the mutation was introduced into CDR1 and 3 only, and they were subjected to fragment PCR and overlapping PCR to construct a library. A theoretical size of the library according to the introduction of the mutation in the case of the heavy chain variable region was $5.83 \times 10^{10}$, and the theoretical size of the library according to the introduction of the mutation in the case of the light chain variable region was $2.16 \times 10^4$.

TABLE 9

HCDR1

| N31 | | | | Y32 | | | | A33 | | | |
|---|---|---|---|---|---|---|---|---|---|---|---|
| Tyr | 7 | THR | 7 | Tyr | 49 | THR | 1 | Tyr | 0.5 | THR | 7 |
| Ser | 8 | Gln | 0 | Ser | 8 | Gln | 0 | Ser | 7.5 | Gln | 0.5 |
| Gly | 1 | Asn | 49 | Gly | 1 | Asn | 7 | Gly | 7 | Asn | 0.5 |
| Arg | 1 | Ala | 1 | Arg | 1 | Ala | 1 | Arg | 1.5 | Ala | 49 |
| Lys | 0 | Val | 1 | Lys | 0 | Val | 1 | Lys | 0.5 | Val | 7 |
| His | 7 | Leu | 1 | His | 7 | Leu | 1 | His | 0.5 | Leu | 1.5 |
| Glu | 0 | Met | 0 | Glu | 0 | Met | 0 | Glu | 3.5 | Met | 0.25 |
| Asp | 7 | Ile | 7 | Asp | 7 | Ile | 1 | Asp | 3.5 | Ile | 0.75 |
| Phe | 1 | Pro | 1 | Phe | 7 | Pro | 1 | Phe | 0.5 | Pro | 7 |
| TRP | 0 | Cys | 1 | TRP | 0 | Cys | 7 | TRP | 0.25 | Cys | 0.5 |
| | | STOP | 0 | | | STOP | 0 | | | STOP | 0.75 |

HCDR2

| D53 | | | | G55 | | | | S56 | | | |
|---|---|---|---|---|---|---|---|---|---|---|---|
| Tyr | 7 | THR | 1 | Tyr | 0.5 | THR | 1 | Tyr | 17.5 | THR | 7 |
| Ser | 2 | Gln | 0 | Ser | 4.5 | Gln | 0.5 | Ser | 49 | Gln | 0 |
| Gly | 7 | Asn | 7 | Gly | 49 | Asn | 0.5 | Gly | 0 | Asn | 2.5 |
| Arg | 1 | Ala | 7 | Arg | 10.5 | Ala | 7 | Arg | 0 | Ala | 7 |
| Lys | 0 | Val | 7 | Lys | 0.5 | Val | 7 | Lys | 0 | Val | 0.5 |
| His | 7 | Leu | 1 | His | 0.5 | Leu | 1.5 | His | 2.5 | Leu | 0.5 |
| Glu | 0 | Met | 0 | Glu | 3.5 | Met | 0.25 | Glu | 0 | Met | 0 |
| Asp | 49 | Ile | 1 | Asp | 3.5 | Ile | 0.75 | Asp | 2.5 | Ile | 0.5 |
| Phe | 1 | Pro | 1 | Phe | 0.5 | Pro | 1 | Phe | 3.5 | Pro | 7 |
| TRP | 0 | Cys | 1 | TRP | 1.75 | Cys | 3.5 | TRP | 0 | Cys | 0 |
| | | STOP | 0 | | | STOP | 2.25 | | | STOP | 0 |

HCDR3

| L98 | | | | S99 | | | | F100 | | | |
|---|---|---|---|---|---|---|---|---|---|---|---|
| Tyr | 0.5 | THR | 1 | Tyr | 14 | THR | 7 | Tyr | 10.5 | THR | 1.5 |
| Ser | 1.5 | Gln | 3.5 | Ser | 49 | Gln | 0 | Ser | 7.75 | Gln | 0 |
| Gly | 1 | Asn | 0.5 | Gly | 0 | Asn | 2 | Gly | 0.25 | Asn | 2.25 |
| Arg | 7.5 | Ala | 1 | Arg | 0 | Ala | 7 | Arg | 0.5 | Ala | 0.5 |
| Lys | 0.5 | Val | 7 | Lys | 0 | Val | 1 | Lys | 0 | Val | 3.5 |
| His | 3.5 | Leu | 52.5 | His | 2 | Leu | 1 | His | 1.5 | Leu | 7 |
| Glu | 0.5 | Met | 1.75 | Glu | 0 | Met | 0 | Glu | 0 | Met | 0 |
| Asp | 0.5 | Ile | 5.25 | Asp | 2 | Ile | 1 | Asp | 0.75 | Ile | 10.5 |
| Phe | 3.5 | Pro | 7 | Phe | 7 | Pro | 7 | Phe | 49 | Pro | 1 |
| TRP | 0.25 | Cys | 0.5 | TRP | 0 | Cys | 0 | TRP | 0 | Cys | 3.5 |
| | | STOP | 0.75 | | | STOP | 0 | | | STOP | 0 |

LCDR1

| S30 | | | |
|---|---|---|---|
| Tyr | 18.8 | THR | 7 |
| Ser | 52.5 | Gln | 0 |
| Gly | 0 | Asn | 2.5 |
| Arg | 0 | Ala | 7 |
| Lys | 0 | Val | 0.5 |
| His | 2.5 | Leu | 0.5 |
| Glu | 0 | Met | 0 |
| Asp | 2.5 | Ile | 0.5 |
| Phe | 3.75 | Pro | 7 |
| TRP | 0 | Cys | 0 |
| | | STOP | 0 |

LCDR3

| W92 | | | | S94 | | | | N95b | | | |
|---|---|---|---|---|---|---|---|---|---|---|---|
| Tyr | 0 | THR | 2 | Tyr | 14 | THR | 7 | Tyr | 7 | THR | 7 |
| Ser | 14 | Gln | 0 | Ser | 49 | Gln | 0 | Ser | 8 | Gln | 0 |
| Gly | 6 | Asn | 0 | Gly | 0 | Asn | 2 | Gly | 1 | Asn | 49 |
| Arg | 12 | Ala | 2 | Arg | 0 | Ala | 7 | Arg | 1 | Ala | 1 |
| Lys | 0 | Val | 2 | Lys | 0 | Val | 1 | Lys | 0 | Val | 1 |
| His | 0 | Leu | 16 | His | 2 | Leu | 1 | His | 7 | Leu | 1 |
| Glu | 0 | Met | 2 | Glu | 0 | Met | 0 | Glu | 0 | Met | 0 |
| Asp | 0 | Ile | 0 | Asp | 2 | Ile | 1 | Asp | 7 | Ile | 7 |
| Phe | 0 | Pro | 2 | Phe | 7 | Pro | 7 | Phe | 1 | Pro | 1 |
| TRP | 42 | Cys | 0 | TRP | 0 | Cys | 0 | TRP | 0 | Cys | 1 |
| | | STOP | 0 | | | STOP | 0 | | | STOP | 0 |

3-2: Construction of Light Chain Variable Region Library

In order to introduce the mutation into the library, first, the light chain variable region was divided into 2 parts, and they were subjected to fragment PCR. The light chain variable region fragment No. 1 had a light chain variable region gene sequence of anti-mesothelin MS502 clone as the template, and a forward primer (SEQ ID NO: 93) and a reverse primer (SEQ ID NO: 94) were added thereto, and the light chain variable region fragment No. 2 had the light chain variable region gene sequence of anti-mesothelin MS502 clone as the template, and a forward primer (Table 10: SEQ ID NO: 95) and a reverse primer (Table 10: SEQ ID NO: 96) were added thereto, and then, each fragment was subjected to PCR using a Primestar polymerase premix (Takara). The PCR was performed by repeating exposure at 98° C. for 2 minutes, and then exposure at 98° C. for 10 seconds, at 60° C. for 15 seconds, and at 72° C. for 20 seconds 30 times, and reacting at 72° C. for 10 minutes. In the amplified genes, DNA bands having an expected size were confirmed on 1% agarose gel, and were separated using a gel extraction kit (QIAquick Gel Extraction Kit, CAT. NO. 28706, QIAGEN), respectively. The light chain constant region had a light chain lambda region as a template, and a forward primer (Table 10: SEQ ID NO: 97), and a reverse primer (Table 10: SEQ ID NO: 98) were added thereto, and each fragment was subjected to PCR using a Primestar polymerase premix. The PCR was performed by repeating exposure at 98° C. for 2 minutes, and then exposure at 98° C. for 10 seconds, at 60° C. for 15 seconds, and at 72° C. for 30 seconds 30 times, and reacting at 72° C. for 10 minutes. In the amplified genes, DNA bands having an expected size were confirmed on 1% agarose gel, and were separated using a gel extraction kit, respectively. The secured light chain variable region fragments 1 and 2, and light chain constant region at a molar ratio of 1:1:1 were used as a template, and a forward primer (SEQ ID NO: 92) and a reverse primer (SEQ ID NO: 98) were added thereto, and each fragment was subjected to PCR using a Primestar polymerase premix. The PCR was performed by repeating exposure at 98° C. for 2 minutes, and then exposure at 98° C. for 20 seconds, at 60° C. for 30 seconds, and at 72° C. for 60 seconds 30 times, and reacting at 72° C. for 10 minutes. In the amplified genes, DNA bands having an expected size were confirmed on 1% agarose gel, and were separated using a gel extraction kit to secure light chain variable-constant region affinity maturation gene. The secured gene was reacted with NruI and XbaI (NEB) restriction enzyme at 37° C. for 4 hours. The genes reacted with the restriction enzyme were separated on 1% Agarose gel again. The separated gene was inserted into the NruI, XbaI site of the linear pComb3x vector containing the MS502 heavy chain variable-constant region by using a T4 DNA ligase (Cat.No.M0203S, NEB). The ligation reaction material was transformed into XL1-Blue bacteria (Electroporation-competent cells; Cat.No. 200228, Stratagene), and cultured in 300 mL of LB medium at 37° C. and at 220 rpm for 1 hour. Then, the resultant material was treated with 150 µL of carbenicillin and 300 µL of tetracycline, and was cultured with shaking at 37° C. and at 220 rpm for 1 hour. The resultant material was treated with VCS M13 helper phage 4.5 mL ($10^{11}$ pfu) and cultured with shaking at 37° C. and at 220 rpm for 1 hour, and treated with 300 µL of kanamycin and 300 µL of carbenicillin, and cultured overnight at 37° C. and at 220 rpm. The next day, the cultured cells were centrifuged at 4000 rpm for 20 minutes, and the supernatant was transferred to a new vessel. In order to precipitate the phage, 5×PEG/NaCl was used to add 1×PEG/NaCl to the supernatant, and the obtained product allowed to stand on ice over 30 minutes. The precipitate phage was centrifuged at 8000 rpm for 30 minutes. The supernatant was discarded and the precipitated phage was re-suspended with 10 mL of PBS. In order to remove cell debris, the phage dissolved in 10 mL of PBS was centrifuged at 14,000 rpm for 10 minutes to separate the supernatant, and stored at 4° C. The library size was confirmed by taking 100 µL of culture fluid after 1 hour of the transformation, plating the culture fluid on the LB plate (Cat.No.LN004CA, Narae-Biotech) containing carbenicillin in serial dilution manner, culturing at 37° C. for 12 hours or more, and counting the colonies.

3-3: Construction of Heavy Chain Variable Region Library

In order to introduce the mutation into the library, first, the heavy chain variable region was divided into 3 parts, and they were subjected to fragment PCR. The heavy chain variable region fragment No. 1 had a heavy chain variable region gene sequence of anti-mesothelin MS502 clone as the template, and a forward primer (Table 10: SEQ ID NO: 99) and a reverse primer (Table 10: SEQ ID NO: 100) were added thereto, and the heavy chain variable region fragment No. 2 had the heavy chain variable region gene sequence of anti-mesothelin MS502 clone as the template, and a forward primer (Table 10: SEQ ID NO: 101) and a reverse primer (Table 10: SEQ ID NO: 102) were added thereto, and the heavy chain variable region fragment No. 3 had the heavy chain variable region gene sequence of anti-mesothelin MS502 clone as the template, and a forward primer (Table 10: SEQ ID NO: 103) and a reverse primer (Table 10: SEQ ID NO: 104) were added thereto, and then, each fragment was subjected to PCR using a Primestar polymerase premix (Takara). The PCR was performed by repeating exposure at 98° C. for 2 minutes, and then exposure at 98° C. for 10 seconds, at 60° C. for 15 seconds, and at 72° C. for 20 seconds 30 times, and reacting at 72° C. for 10 minutes. In the amplified genes, DNA bands having an expected size were confirmed on 1% agarose gel, and were separated using a gel extraction kit, respectively. The secured heavy chain variable region fragments 1, 2, and 3 at a molar ratio of 1:1:1 were used as a template, and a forward primer (Table 10: SEQ ID NO: 99) and a reverse primer (Table 10: SEQ ID NO: 106) were added thereto, and each fragment was subjected to PCR using a Primestar polymerase premix. The PCR was performed by repeating exposure at 98° C. for 2 minutes, and then exposure at 98° C. for 20 seconds, at 60° C. for 30 seconds, and at 72° C. for 60 seconds 30 times, and reacting at 72° C. for 10 minutes. In the amplified genes, DNA bands having an expected size were confirmed on 1% agarose gel, and were separated using a gel extraction kit to secure heavy chain variable region affinity maturation gene. The secured gene was reacted with XhoI and ApaI (NEB) restriction enzyme at 37° C. for 4 hours. The genes reacted with the restriction enzyme were separated on 1% Agarose gel again. The separated gene was inserted into the XhoI, ApaI site of the linear pComb3x vector containing the MS502 light chain variable-constant region by using a T4 DNA ligase (Cat.No.M0203S, NEB). The ligation reaction material was transformed into XL1-Blue bacteria (Electroporation-competent cells; Cat.No. 200228, Stratagene), and cultured in 300 mL of LB medium at 37° C. and at 220 rpm for 1 hour. Then, the resultant material was treated with 150 µL of carbenicillin and 300 µL of tetracycline, and was suspension-cultured at 37° C. and at 220 rpm for 1 hour. The resultant material was treated with VCS M13 helper phage 4.5 mL (1011 pfu) and cultured with shaking at 37° C. and at 220 rpm for 1 hour, and treated with 300 µL of kanamycin and 300 µL of carbenicillin, and cultured overnight at 37° C.

and at 220 rpm. Next day, the cultured cells were centrifuged at 4000 rpm for 20 minutes, and the supernatant was transferred to a new vessel. In order to precipitate the phage, 5×PEG/NaCl was used to add 1×PEG/NaCl to the supernatant, and the obtained product allowed to stand on ice over 30 minutes. The precipitated phage was centrifuged at 8000 rpm for 30 minutes. The supernatant was discarded and the precipitated phage was re-suspended with 10 mL of PBS. In order to remove cell debris, the phage dissolved in 10 mL of PBS was centrifuged at 14,000 rpm for 10 minutes to separate the supernatant, and stored at 4° C. The library size was confirmed by taking 100 µL of culture fluid after 1 hour of the transformation, plating the culture fluid on the LB plate (Cat.No.LN004CA, NaraeBiotech) containing carbenicillin in serial dilution manner, culturing at 37° C. for 12 hours or more, and counting the colonies.

In Table 10, X codon is a degenerative codon in which each ACGT is controlled at a specific rate, and is able to control a rate of the amino acids to be translated. As an example, for the NX1X2 codon of SEQ ID NO: 102, N is encoded by A, C, G, T with a random ratio, X1 is encoded at 10% of A, 10% of C, 70% of G, and 10% of T, and X2 is encoded at 10% of A, 70% of C, 10% of G, and 10% of T. This is designed for the reverse primer, and thus, if it is converted to the forward direction, it is the X2X1N codon, wherein X2 is encoded at 10% of A, 70% of C, 10% of G, and 10% of T, and X1 is encoded at 10% of A, 10% of C, 70% of G, and 10% of T. As a result, Kabat No. 31 of the heavy chain variable region CDR1 is translated into amino acids, Tyr 7%, Ser 8%, Gly 1%, His 7%, Asp 7%, Phe 1%, Thr 7%, Asn 49%, Ala 1%, Val 1%, Leu 1%, Ile 7%, Pro 1%, Cys 1%.

TABLE 10

| Name | Nucleotide sequence | SEQ ID NO: |
|---|---|---|
| MS502 VL FR1 Fo NruI | Tcgcgattgcagtggcactggctggtttcgctaccgtggc- ccaggcggcc CAG TCT GTG CTG ACT CAG CCA CCC TCA | 94 |
| MS502 VL FR1 Fo | CAG TCT GTG CTG ACT CAG CCA CCC TCA | 95 |
| MS502 VL FR1 Re | GAG CTG CTG GTA CCA GGA GAC AGC ATT RX5X4 GCC AAT ATT AGA TGA AGA GCC AGT ACA AGA | 96 |
| MS502 VL FR2 Fo | GCC AAT ATT AGA TGA AGA GCC AGT ACA AGA | 97 |
| MS502 VL FR2 Re | ACC TAG GAC GGT CAC CTT GGT GCC TCC GCC GAA GAC ATA ACC RX3X3 CAG GCT RX7X4 ATC CX8X4 AGA ACC ACA GTA ATA ATC AGC CTC ATC CTC GGA | 98 |
| MS502 CL Fo | GGC ACC AAG GTG ACC GTC CTA GGT CAG CCC AAG GCC AAC CCC ACT GTC | 99 |
| MS502 CL Re | GCT CTA GAA CAT TCT GTA GGG GCC ACT GTC TTC TC | 100 |
| MS502 VH FR1 Fo NcoI | gcccatggcc GAG GTG CAG CTG TTG GAG TCT GGG | 101 |
| MS502 VH FR1 Re | AGC CTG GCG GAC CCA GCT CAT NX1X2 RX3X4 RX3X3 GCT AAA GGT GAA TCC AGA GGC CGC ACA | 102 |
| MS502 VH FR2 Fo | atgagctgggtccgccaggct | 103 |
| MS502 VH FR2 Re | GGT GAA CCG ACC TCT TAC AGA ATC AGC GTA ATA TTT RX5X4 NX2X2 ACT RX3X2 AGG AGG GAT CCC TGA GAC CCA CTC | 104 |
| MS502 VH FR3 Fo | AAA TAT TAC GCT GAT TCT GTA AGA GGT CGG TTC ACC | 105 |
| MS502 VH FR3 Re | TGA GCT CAC CGT GAC CAG TGT ACC CTG GCC CCA GTA GTC RX6X6 RX7X4 NX4X1 CAT ATT TTT CGC ACA GTA ATA CAC GGC CGT | 106 |
| MS502 VH Re | TGA GCT CAC CGT GAC CAG TGT ACC CTG | 107 |
| MS502 VH Re ApaI | GCG GGC CCT TGG TGG AGG CTG AGC TCA CCG TGA CCA GTG TAC CCT G | 108 |

3-4: Selection of Light Chain Variable Region Mutation Antibody 1 mL of recombinant human protein MSLN having a concentration of 1 μg/mL was put in a solid phase polystyrene tube (Cat.No. 444202, Nunc), and the tube coated at 4° C. for 12 hours or more was washed with 5 mL of 0.05% PBST three times. 5 mL of 1% BSA/PBS was put in the MSLN-coated immuno tube, followed by blocking at room temperature for 2 hours. A blocking buffer was removed from the immuno tube, and then, the light chain variable region phage library was treated in the tube and reacted at room temperature for 2 hours. Then, the obtained product was washed with 5 mL of PBST four times. The immuno tube was treated with 1 mL of glycine (pH 2.0) elution buffer, and reacted at room temperature for 10 minutes to obtain the supernatant. After elution, 100 μL of 1.5M Tris-Cl (pH 8.8) was added to the phage and neutralized. 10 mL of XL1-Blue bacteria (electroporation-competent cells; Cat.No. 200228, Stratagene) cultured for about 2 hours ($OD_{600}$=0.8 to 1.0) were treated with the neutralized phage. After infection at room temperature for 30 minutes, 10 mL of SB, 20 μL of tetracycline (50 mg/ml), and 10 μL of carbenicillin (100 mg/mL) were added to 10 mL of the infected XL1-Blue bacteria (electroporation-competent cells; Cat.No. 200228, Stratagene), and cultured with shaking (200 rpm) at 37° C. for 1 hour. The bacteria were treated with 1 mL of VCSM13 helper phage ($>10^{11}$ pfu/ml), and cultured with shaking (200 rpm) at 37° C. for 1 hour. After 1 hour incubation, the bacteria were treated with 80 mL of SB, 100 μL of kanamycin, and 100 μL of carbenicillin (100 mg/mL), and cultured overnight (200 rpm) at 37° C. The overnight cultured library was centrifuged at 4000 rpm for 15 minutes to separate the supernatant only, and 5×PEG/NaCl was used to add 1×PEG/NaCl to the supernatant, and the obtained product allowed to stand on ice over 30 minutes. The supernatant was removed by centrifugation at 8000 rpm for 30 minutes, and pellets were re-suspended with 2 ml of 1% BSA/PBS and centrifuged at 12000 rpm for 10 minutes. Then, only the supernatant was taken and used in the following order panning. This process was repeated four times.

3-5: Selection of Heavy Chain Variable Region Mutation Antibody

The supernatant was removed with 50 μL of streptavidin microbead (Miltenyl biotec 130-048-101), and 1 mL of PBS was added thereto to perform washing three times. 1 mL of PBS containing 1% BSA was added to the bead, and the bead was rotated at room temperature for 2 hours, followed by blocking. 50 nM MSLN was put in 500 μL of PBS, and mixed with 500 μL of MS502 VH rational library phage and rotation-reacted at room temperature for 1 hour. The blocking buffer was removed from the bead, and the bead was treated with a solution containing the MSLN and the phage, and reacted at room temperature for 15 minutes. Then, the obtained product was washed with 1 mL of PBST six times. The bead was treated with 1 mL of glycine (pH 2.0) elution buffer, and reacted at room temperature for 10 minutes to obtain the supernatant. After elution, 100 μL of 1.5M Tris-Cl (pH 8.8) was added to the phage and neutralized. 10 mL of XL1-Blue bacteria (electroporation-competent cells; Cat.No. 200228, Stratagene) cultured for about 2 to 2.5 hours ($OD_{600}$=0.8 to 1.0) were treated with the neutralized phage. After infection at room temperature for 30 minutes, 10 mL of SB, 20 μL of tetracycline (50 mg/ml), and 10 μL of carbenicillin (100 mg/mL) were added to 10 mL of the infected XL1-Blue bacteria (electroporation-competent cells; Cat.No. 200228, Stratagene), and cultured with shaking (200 rpm) at 37° C. for 1 hour. The bacteria were treated with 1 mL of VCSM13 helper phage($>10^{11}$ pfu/ml), and suspension-cultured (200 rpm) at 37° C. for 1 hour. After 1 hour incubation, the bacteria were treated with 80 mL of SB, 100 μL of kanamycin, and 100 μL of carbenicillin (100 mg/mL), and cultured overnight (200 rpm) at 37° C. The overnight cultured library was centrifuged at 4000 rpm for 15 minutes to separate the supernatant only, and 5×PEG/NaCl buffer was used to add 1×PEG/NaCl to the supernatant, and the obtained product allowed to stand on ice over 30 minutes. The supernatant was removed by centrifugation at 8000 rpm for 30 minutes, and pellets were re-suspended with 2 m of 1% BSA/PBS and centrifuged at 12000 rpm for 10 minutes. Then, only the supernatant was taken and used in the following order panning. A total of primary, secondary, and tertiary bead panning with regard to the MSLN were performed by using MS502 $V_H$ rational library phage. As a result of the secondary and tertiary pannings, it was confirmed that output titers were increased, which showed that the antibodies against the MSLN were amplified.

3-6: Secure of Individual Clones According to ELISA

Single colonies of a final amplified population of each library of light chain/heavy chain variable regions were collected, and cultured with 1.5 mL of SB/carbenicillin up to an $OD_{600}$ of 0.8 to 1.0 at 37° C. and at 220 rpm, and then cultured with 1 mM IPTG at 30° C. and at 200 rpm for 12 hours or more. The reaction materials were centrifuged at 5500 rpm for 5 minutes, and only each supernatant was added to ELISA plates containing underlying MSLN antigen, and reacted at room temperature for 2 hours. Then, the resultant materials were washed with PBST (1×PBS, 0.05% tween 20) four times, and HRP/Anti-hFab-HRP conjugate diluted by 1/5000 with 1% BSA/1×PBS was added thereto, and reacted at room temperature for 1 hour, and washed with PBST (1×PBS, 0.05% tween 20) 4 times. Then, a TMB solution was added and allowed to stand for 5 to 10 minutes, and a TMB stop solution was added thereto. Next, O.D values were measured at a measurement wavelength of 450 nm using a TECAN sunrise, and clones having high O.D value were secured as individual clones.

As a result, as shown in Table 11, the clones specifically bound to the human MSLN were able to be selected, and amino acid sequences thereof were identified.

Table 12 shows CDR amino acid sequences of the clone antibodies of Table 11 on the basis of Kabat numbering.

TABLE 11

| clone | variable region | amino acid sequence | SEQ ID NO: |
|---|---|---|---|
| C2G1 | heavy chain | EVQLLESGGGLVQPGGSLRLSCAAS GFTFSNYAMSWVRQAPGKGLEWVS GIPPDSGSKYYADSVRGRFTVSRDNS KNTLYLQMNSLRAEDTAVYYCAKN MLSFDYWGQGTLVTVSS | 49 |

TABLE 11-continued

| clone | variable region | amino acid sequence | SEQ ID NO: |
|---|---|---|---|
| | light chain | QSVLTQPPSASGTPGQRVTISCTGSSS NIGPNAVSWYQQLPGTAPKLLIYYNS KRPSGVPDRFSGSKSGTSASLAISGLR SEDEADYYCGSWDSSLSGYVFGGGT KVTVLG | 109 |
| C2G4 | heavy chain | EVQLLESGGGLVQPGGSLRLSCAAS GFTFSNYAMSWVRQAPGKGLEWVS GIPPDSGSKYYADSVRGRFTVSRDNS KNTLYLQMNSLRAEDTAVYYCAKN MLSFDYWGQGTLVTVSS | 48 |
| | light chain | QSVLTQPPSASGTPGQRVTISCTGSSS NIGSNAVSWYQQLPGTAPKLLIYYNS KRPSGVPDRFSGSKSGTSASLAISGLR SEDEADYYCGSWDPSLNGYVFGGGT KVTVLG | 110 |
| C3C8 | heavy chain | EVQLLESGGGLVQPGGSLRLSCAAS GFTFSNYAMSWVRQAPGKGLEWVS GIPPDSGSKYYADSVRGRFTVSRDNS KNTLYLQMNSLRAEDTAVYYCAKN MLSFDYWGQGTLVTVSS | 48 |
| | light chain | QSVLTQPPSASGTPGQRVTISCTGSSS NIGPNAVSWYQQLPGTAPKLLIYYNS KRPSGVPDRFSGSKSGTSASLAISGLR SEDEADYYCGSWDSDLRGYVFGGG TKVTVLG | 111 |
| 54 | heavy chain | EVQLLESGGGLVQPGGSLRLSCAAS GFTFSNYAMSWVRQAPGKGLEWVS GIYPDSSTYYADSVKGRFTISRDNS KNTLYLQMNSLRAEDTAVYYCARNI YTFDYWGQGTLVTVSS | 112 |
| | light chain | QSVLTQPPSASGTPGQRVTISCTGSSS NIGSNAVSWYQQLPGTAPKLLIYYNS KRPSGVPDRFSGSKSGTSASLAISGLR SEDEADYYCGSWDSSLNGYVFGGGT KVTVLG | 49 |
| 56 | heavy chain | EVQLLESGGGLVQPGGSLRLSCAAS GFTFSNYAMSWVRQAPGKGLEWVS GIPPDSASKYYADSVRGRFTVSRDNS KNTLYLQMNSLRAEDTAVYYCAKN MLSFDYWGQGTLVTVSS | 113 |
| | light chain | QSVLTQPPSASGTPGQRVTISCTGSSS NIGSNAVSWYQQLPGTAPKLLIYYNS KRPSGVPDRFSGSKSGTSASLAISGLR SEDEADYYCGSWDSSLNGYVFGGGT KVTVLG | 49 |
| 2-30 | heavy chain | EVQLLESGGGLVQPGGSLRLSCAAS GFTFSNYAMSWVRQAPGKGLEWVS GIPPDSNSKYYADSVRGRFTVSRDNS KNTLYLQMNSLRAEDTAVYYCAKN MRTFDYWGQGTLVTVSS | 114 |
| | light chain | QSVLTQPPSASGTPGQRVTISCTGSSS NIGSNAVSWYQQLPGTAPKLLIYYNS KRPSGVPDRFSGSKSGTSASLAISGLR SEDEADYYCGSWDSSLNGYVFGGGT KVTVLG | 49 |
| 2-73 | heavy chain | EVQLLESGGGLVQPGGSLRLSCAAS GFTFSNYAMSWVRQAPGKGLEWVS GIPPNSDSKYYADSVRGRFTVSRDNS KNTLYLQMNSLRAEDTAVYYCAKN MLSFDYWGQGTLVTVSS | 115 |
| | light chain | QSVLTQPPSASGPPGQRVTISCTGSSS NIGNNSVSWYQQLPGTAPKLLIYYDS HRPSGVPDRFSGSKSGTSASLAIGGL RSEDEADYYCGAWDDSLNAYVFGGG GTKLTVLG | 49 |
| 2-78 | heavy chain | EVQLLESGGGLVQPGGSLRLSCAAS GFTFSNYAMSWVRQAPGKGLEWVS GIPPDSGSKYYADSVRGRFTVSRDNS KNTLYLQMNSLRAEDTAVYYCAKN MFSFDYWGQGTLVTVSS | 116 |

TABLE 11-continued

| clone | variable region | amino acid sequence | SEQ ID NO: |
|---|---|---|---|
| | light chain | QSVLTQPPSASGTPGQRVTISCTGSSS NIGSNAVSWYQQLPGTAPKLLIYYNS KRPSGVPDRFSGSKSGTSASLAISGLR SEDEADYYCGSWDSSLNGYVFGGGT KVTVLG | 49 |

TABLE 12

| clone | variable region | CDR1 | CDR2 | CDR3 |
|---|---|---|---|---|
| C2G1 | heavy chain | NYAMS (SEQ ID NO: 59) | GIPPDSGSKYYAD SVRG (SEQ ID NO: 65) | NMLSFDY (SEQ ID NO: 66) |
| | light chain | TGSSSNIGPNAV S (SEQ ID NO: 117) | YNSKRPS (SEQ ID NO: 68) | GSWDSSLSGYV (SEQ ID NO: 118) |
| C2G4 | heavy chain | NYAMS (SEQ ID NO: 59) | GIPPDSGSKYYAD SVRG (SEQ ID NO: 65) | NMLSFDY (SEQ ID NO: 66) |
| | light chain | TGSSSNIGSNAV S (SEQ ID NO: 67) | YNSKRPS (SEQ ID NO: 68) | GSWDPSLNGYV (SEQ ID NO: 119) |
| C3C8 | heavy chain | NYAMS (SEQ ID NO: 59) | GIPPDSGSKYYAD SVRG (SEQ ID NO: 65) | NMLSFDY (SEQ ID NO: 66) |
| | light chain | TGSSSNIGPNAV S (SEQ ID NO: 117) | YNSKRPS (SEQ ID NO: 68) | GSWDSDLRGYV (SEQ ID NO: 120) |
| 54 | heavy chain | NYAMS (SEQ ID NO: 59) | GIPPDSSSKYYAD SVRG (SEQ ID NO: 121) | NMLSFDY (SEQ ID NO: 66) |
| | light chain | TGSSSNIGSNAV S (SEQ ID NO: 67) | YNSKRPS (SEQ ID NO: 68) | GSWDSSLNGYV (SEQ ID NO: 69) |
| 56 | heavy chain | NYAMS (SEQ ID NO: 59) | GIPPDSASKYYAD SVRG (SEQ ID NO: 122) | NMLSFDY (SEQ ID NO: 66) |
| | light chain | TGSSSNIGSNAV S (SEQ ID NO: 67) | YNSKRPS (SEQ ID NO: 68) | GSWDSSLNGYV (SEQ ID NO: 69) |
| 2-30 | heavy chain | NYAMS (SEQ ID NO: 59) | GIPPDSNSKYYAD SVRG (SEQ ID NO: 123) | NMRTFDY (SEQ ID NO: 124) |
| | light chain | TGSSSNIGSNAV S (SEQ ID NO: 67) | YNSKRPS (SEQ ID NO: 68) | GSWDSSLNGYV (SEQ ID NO: 69) |
| 2-73 | heavy chain | NYAMS (SEQ ID NO: 59) | GIPPNSDSKYYAD SVRG (SEQ ID NO: 125) | NMLSFDY (SEQ ID NO: 66) |
| | light chain | TGSSSNIGSNAV S (SEQ ID NO: 67) | YNSKRPS (SEQ ID NO: 68) | GSWDSSLNGYV (SEQ ID NO: 69) |
| 2-78 | heavy chain | NYAMS (SEQ ID NO: 59) | GIPPDSGSKYYAD SVRG (SEQ ID NO: 65) | NMFSFDY (SEQ ID NO: 126) |
| | light chain | TGSSSNIGSNAV S (SEQ ID NO: 67) | YNSKRPS (SEQ ID NO: 68) | GSWDSSLNGYV (SEQ ID NO: 69) |

3-7: Relative Comparison and Selection in Binding Force of Individual Clones Using SPR In order to compare and measure the binding force with culture fluid of individual clones secured from confirmation of the individual clones according to ELISA method conducted in Example 3-3, first, the human MSLN on the biacore series S CM5 chip (GE healthcare) was dissolved in pH 4.0 acetate buffer to be 1 µg/ml, and allowed to flow at a flow rate of 10 µL/min and fixed to 1000 Ru. The Fab supernatant expressed in Example 3-6 was diluted by 1/10 with pH 7.4 HBS-EP buffer, and was allowed to flow at a flow rate of 30 µL/min for association of 120 seconds, and dissociation of 180 seconds to conduct binding analysis. The regeneration was performed with 10 mM glycine-HCl pH 1.5 buffer for 30 seconds. The ELISA and the SPR binding data were compared and analyzed to select the final clones of the light chain variable region and the heavy chain variable region.

Figure 2:
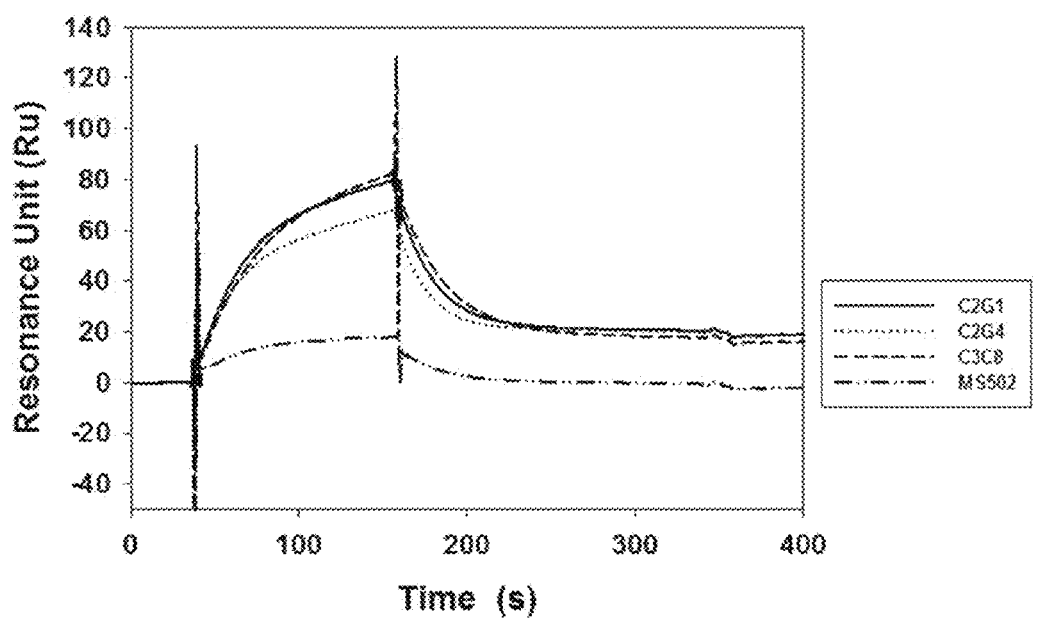
FIG. 2 illustrates relative comparison of light chain variable region mutants in view of binding force.
Figure 3:
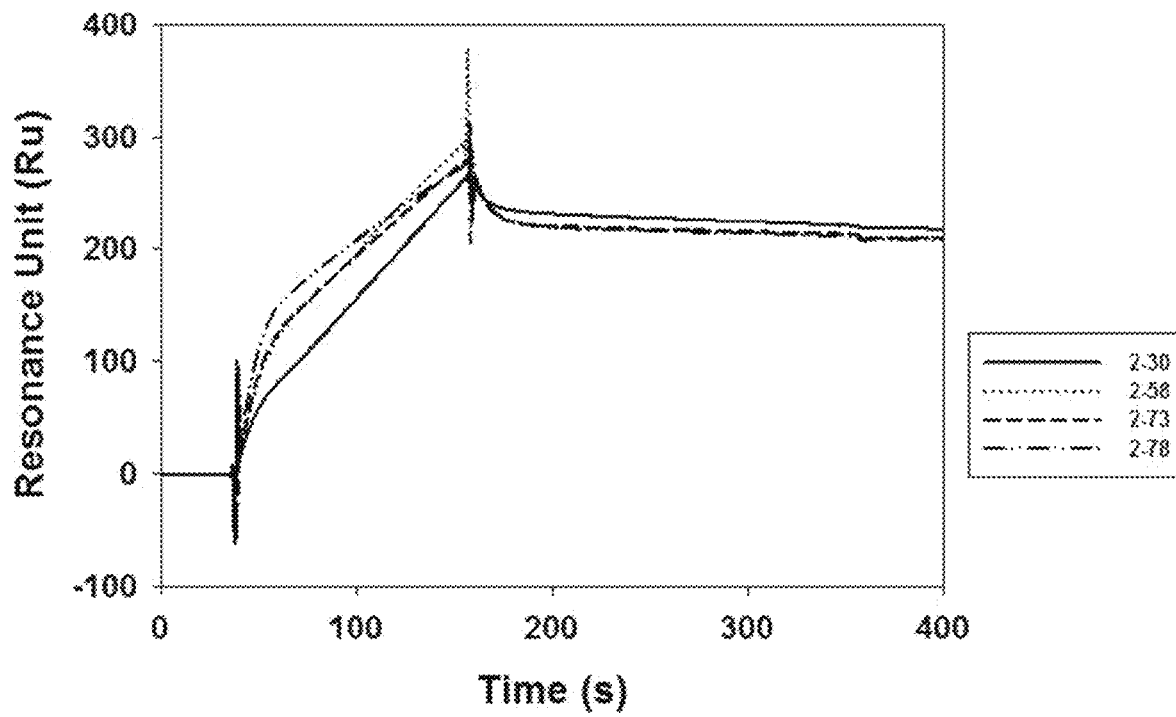
FIG. 3 illustrates relative comparison of heavy chain variable region mutants in view of binding force.

As a result, as illustrated in FIGS. 2 and 3, the binding force of the light chain variable region mutations and the heavy chain variable region mutations were relatively compared, and C2G1, C2G4, and C3C8 were selected for the final clones of the light chain variable region and 56, 2-30, 2-58, 2-73, and 2-78 were selected for the final clones of the heavy chain variable region.

3-8: IgG Gene Cloning of Clone MS502 Light Chain Variable Region Mutation Antibody Each of the secured light chain variable region C2G1, C2G4, and C3C8 genes as the template was subjected to PCR by using PrimeSTAR HS DNA polymerase (Cat.No.R010B; Takara) and the forward primer containing NotI (Table 6: SEQ ID NO: 86) and the reverse primer (Table 6: SEQ ID NO: 87). Further, human antibody kappa light chain constant region was subjected to PCR with the forward primer (Table 6: SEQ ID NO: 88) and the reverse primer (Table 6: SEQ ID NO: 89). The PCR was performed by repeating exposure at 94° C. for 10 minutes, and then exposure at 94° C. for 15 seconds, at 56° C. for 30 seconds, and at 72° C. for 90 seconds 30 times, and reacting at 72° C. for 10 minutes. In the amplified genes, DNA bands having an expected size were confirmed on 1% agarose gel, and were separated using a gel extraction kit, respectively. Then, the respective light chain variable regions and light chain constant regions were mixed, followed by overlapping PCR, such that the genes expressing the light chain region were cloned. The PCR was performed by repeating exposure at 94° C. for 10 minutes, and then exposure at 94° C. for 15 seconds, at 56° C. for 30 seconds, and at 72° C. for 90 seconds 30 times, and reacting at 72° C. for 10 minutes. In the amplified genes, DNA bands having an expected size were confirmed on 1% agarose gel, and were separated using a gel extraction kit, respectively. Then, the separated genes reacted with NotI, HindIII restriction enzymes at 37° C. for 12 hours or more, and the genes reacted with the restriction enzymes were separated on 1% agarose gel again. The pcIW plasmid vector was also cut by the same method as above and separated on agarose gel. The separated C2G1, C2G4, and C3C8 light chain region genes were inserted into NotI, HindIII sites of the linear pcIW vector by using a T4 DNA ligase (Cat.No.M0203S, New England BioLabs (NEB)). The ligation reaction materials were transformed into XL1-Blue bacteria (Electroporation-Competent Cells; Cat.No. 200228, Stratagene), plated on an LB plate (Cat.No.LN004CA, NaraeBiotech) containing carbenicillin, and cultured at 37° C. for 12 hours or more. Then single colonies were chosen and cultured, and plasmids were separated by using a plasmid mini kit (Cat.No. 27405, QIAGEN), and confirmed by DNA sequencing.

3-9: IgG Gene Cloning of Clone MS502 Heavy Chain Variable Region Mutation Antibody Each of the heavy chain variable region 56, 2-30, 2-58, 2-73, and 2-78 genes as the template was subjected to PCR by using PrimeSTAR HS DNA polymerase (Cat.No.R010B; Takara) and the forward primer containing NotI (Table 6: SEQ ID NO: 90) and the reverse primer containing ApaI (Table 6: SEQ ID NO: 91). The PCR was performed by repeating exposure at 98° C. for 2 minutes, and then exposure at 98° C. for 10 seconds, at 58° C. for 10 seconds, and at 72° C. for 30 seconds 30 times, and reacting at 72° C. for 5 minutes. In the amplified genes, DNA bands having an expected size were confirmed on 1% agarose gel, and were separated using a gel extraction kit, respectively. Then, the three kinds of separated genes were reacted with KpnI and ApaI restriction enzyme at 37° C. for 4 hours. The genes reacted with the restriction enzyme were separated on 1% Agarose gel again. The pcIW plasmid vector was also cut by the same method as above and separated on agarose gel. The separated genes were inserted into the NotI, ApaI sites of the linear pcIw vector containing the human heavy chain constant region by using a T4 DNA ligase. The ligation reaction materials were transformed into XL1-Blue bacteria (Electroporation-Competent Cells; Cat.No. 200228, Stratagene), plated on an LB plate (Cat.No.LN004CA, NaraeBiotech) containing carbenicillin, and cultured at 37° C. for 12 hours or more. Then single colonies were chosen and cultured, and plasmids were separated by using a plasmid mini kit (Cat.No. 27405, QIAGEN), and confirmed by DNA sequencing.

3-10: Production and Purification of IgG of Clone MS502 Light Chain Variable Region Mutation Antibody In order to produce and purify the light chain variable region mutation antibodies C2G1, C2G4, and C3C8, Expi293F™ cells were inoculated at a concentration of $2.5 \times 10^6$ cell/mL the day before transfection. After incubation (37° C., 8% $CO_2$, 125 rpm) for 24 hours, Expi293™ expression medium (Cat.No.A1435101, Gibco) was added to prepare a product of 30 mL having a concentration of $2.5 \times 10^6$ cell/mL (viability=95%). 30 μg of DNA (pcIw-MS502 heavy chain variable region: 15 μg, pcIw-anti-Mesothelin light chain variable region mutant: 15 μg) was diluted in an OptiPro™ SEM medium (Cat.No. 12309019, Gibco) so as to have a total volume of 1.5 mL, and reacted at room temperature for 5 minutes. 1.5 mL of the OptiPro™ SEM medium (Cat.No. 12309019, Gibco) was mixed with 80 μL of an ExpiFectamine™ 293 reagent (Cat.No.A14524, Gibco) so that a total volume is 1.5 mL, and reacted at room temperature for 5 minutes. After the reaction for 5 minutes, 1.5 mL of diluted DNA and 1.5 mL of diluted ExpiFectamine™ 293 reagent were well-mixed with each other, and reacted at room temperature for 20 to 30 minutes. 3 mL of the mixture of DNA and ExpiFectamine™ 293 reagent was treated in the Expi293F™ cells. After suspension-culture (37° C., 8% $CO_2$, 125 rpm) for 16 to 18 hours, 150 μL of ExpiFectamine™ 293 Enhancer 1(Cat.No.A14524, Gibco) and 1.5 mL of ExpiFectamine™ 293 Enhancer2 (Cat.No.A14524, Gibco) were added thereto, followed by suspension-culturing for 5 days. After the culturing, cell debris was removed by centrifugation at 4000 rpm for 20 minutes, and the supernatant passed through 0.22 μm filter to be prepared. MabSelect Xtra (Cat.No. 17-5269-02, GE Healthcare) which is protein A resin having 100 μL was prepared for each 30 mL of the culture fluid, followed by centrifugation at 1000 rpm for 2 minutes to remove a storage solution, and the obtained product was washed with 400 μL of protein A binding buffer (Cat.No. 21007, Pierce) 3 times. The protein A resin was added to the prepared culture fluid and rotation-reacted at room temperature for 30 minutes. The mixture of the culture fluid and the resin was put into a pierce spin column snap-cap (Cat.No. 69725, Thermo), and then, only the resin was left in the column using QIAvac 24 Plus(Cat.No. 19413, QIAGEN) vacuum manifold. 5 mL of protein A binding buffer was added to wash the resin, and 200 μL of a protein A elution buffer (Cat.No. 21009, Pierce) was added thereto. The resultant material was reacted by resuspension at room temperature for 2 minutes, and centrifuged at 1000 rpm for 1 minute, and eluted. Each eluate was neutralized by adding 2.5 μL of 1.5M Tris-HCl (pH 9.0). The elution was performed 4 to 6 times, and each fraction was quantified by using Nanodrop 200C (Thermo scientific). The fractions in which protein is detected were collected, and exchanged with a PBS (Phosphate-Buffered Saline) buffer using Zeba Spin Desalting Columns, 7K MWCO, 5 mL (Cat.No. 0089892, Pierce). Then, protein electrophoresis (SDS-PAGE) was performed under reduction and non-reduction condition to finally verify the concentration quantification and the antibody state, and the antibody was kept at 4° C.

3-11: Measurement of Quantitative Binding Force of MS502 Light Chain Variable Region Mutation Antibody with Regard to MSLN Antigen Quantitative binding force (affinity) of the purified anti-MSLN antibodies, i.e., the MS502 clone light chain variable region mutation antibodies C2G1, C2G4, and C3C8 with regard to the recombinant human mesothelin (MSLN) was measured by using a Biacore T-200 (GE Healthcare, U.S.A.) biosensor. The MSLN (Cat.No. 3265-MS, R&D systems, U.S.A.) purified from the HEK293 cells was fixed to a CMS chip (GE Healthcare, CAT. No. BR-1005-30) so as to satisfy 200 Rmax by using an amine-carboxylic reaction. Then, the clone C2G1 antibody, the clone C2G4 antibody or the clone C3C8 antibody serially diluted with HBS-EP buffer (10 mM HEPES, pH7.4, 150 mM NaCl, 3 mM EDTA, 0.005% surfactant P20) was allowed to flow at a concentration range of 0.078 nM to 5 nM and at a flow rate of 30 μL/min for association of 120 seconds and dissociation of 1800 seconds. The dissociation of the antibody bound to the MSLN was induced by flowing 10 mM Glycine-HCl pH 1.5 at a flow rate of 30 μL/min for 30 seconds (Table 13). The affinity was obtained as movement speed constants ($K_{on}$ and $K_{off}$) and an equilibrium dissociation constant ($K_D$) by using a Biacore T-200 evaluation software (Table 14).

TABLE 13

| SPR | Biacore T200 |
| --- | --- |
| Chip | CM5 |
| Running Buffer | HBS-EP pH 7.4 |
| Flow rate | 30 μL/min |
| Association/dissociation time | 120 sec/600 sec |
| IgG Conc. | 0.078~5 nM, ½ serial dilution |
| Regeneration | 10 mM Glycine-HCl pH 1.5, 30 sec |

TABLE 14

|  | $K_{on}$ | $K_{off}$ | $K_D$ |
| --- | --- | --- | --- |
| C2G1 | $7.20 \times 10^7$ | $6.76 \times 10^{-3}$ | $9.39 \times 10^{-11}$ |
| C2G4 | $1.40 \times 10^8$ | $6.05 \times 10^{-3}$ | $4.32 \times 10^{-11}$ |
| C3C8 | $5.84 \times 10^7$ | $7.11 \times 10^{-3}$ | $1.22 \times 10^{-10}$ |

3-12: Production and Purification of IgG of Clone MS502 Heavy Chain Variable Region Mutation Antibody In order to produce and purify the heavy chain variable region mutation antibodies 56, 2-30, 2-58, 2-73, 2-78, Expi293F™ cells were inoculated at a concentration of $2.5 \times 10^6$ cell/mL the day before transfection. After incubation (37° C., 8% $CO_2$, 125 rpm) for 24 hours, Expi293™ expression medium (Cat.No.A1435101, Gibco) was added to prepare a product of 30 mL having a concentration of $2.5 \times 10^6$ cell/mL (viability=95%). 30 μg of DNA (pcIw-MS502 heavy chain variable region mutation antibody: 15 μg, pcIw-MS502 light chain variable region: 15 μg) was diluted in an OptiPro™ SEM medium (Cat.No. 12309019, Gibco) so as to have a total volume of 1.5 mL, and reacted at room temperature for 5 minutes. 1.5 mL of the OptiPro™ SEM medium (Cat.No. 12309019, Gibco) was mixed with 80 μL of an ExpiFectamine™ 293 reagent (Cat.No.A14524, Gibco) so that a total volume is 1.5 mL, and reacted at room temperature for 5 minutes. After the reaction for 5 minutes, 1.5 mL of diluted DNA and 1.5 mL of diluted ExpiFectamine™ 293 reagent were well-mixed with each other, and reacted at room temperature for 20 to 30 minutes. 3 mL of the mixture of DNA and ExpiFectamine™ 293 reagent was treated in the Expi293F™ cells. After suspension-culture (37° C., 8% $CO_2$, 125 rpm) for 16 to 18 hours, 150 μL of ExpiFectamine™ 293 Enhancer 1 (Cat.No.A14524, Gibco) and 1.5 mL of ExpiFectamine™ 293 Enhancer2 (Cat.No.A14524, Gibco) were added thereto, followed by suspension-culturing for 5 days. After the culturing, cell debris was removed by centrifugation at 4000 rpm for 20 minutes, and the supernatant passed through 0.22 μm filter to be prepared. MabSelect Xtra (Cat.No. 17-5269-02, GE Healthcare) which is protein A resin having 100 μL was prepared for each 30 mL of the culture fluid, followed by centrifugation at 1000 rpm for 2 minutes to remove a storage solution, and the obtained product was washed with 400 μL of protein A binding buffer (Cat.No. 21007, Pierce) 3 times. The protein A resin was added to the prepared culture fluid and rotation-reacted at room temperature for 30 minutes. The mixture of the culture fluid and the resin was put into a pierce spin column snap-cap (Cat.No. 69725, Thermo), and then, only the resin was left in the column using QIAvac 24 Plus(Cat.No. 19413, QIAGEN) vacuum manifold. 5 mL of protein A binding buffer was added to wash the resin, 200 μL of a protein A elution buffer (Cat.No. 21009, Pierce) was added thereto. The resultant material was reacted by resuspension at room temperature for 2 minutes, and centrifuged at 1000 rpm for 1 minute, and eluted. Each eluate was neutralized by adding 2.5 μL of 1.5M Tris-HCl (pH 9.0). The elution was performed 4 to 6 times, and each fraction was quantified by using Nanodrop 200C (Thermo scientific). The fractions in which protein is detected were collected, and exchanged with a PBS (Phosphate-Buffered Saline) buffer using Zeba Spin Desalting Columns, 7K MWCO, 5 mL (Cat.No. 0089892, Pierce). Then, protein electrophoresis (SDS-PAGE) was performed under reduction and non-reduction condition to finally verify the concentration quantification and the antibody state, and the antibody was kept at 4° C.

3-13: Production and Purification of IgG of Heavy Chain Variable Region Mutation Antibody Combined with Final Light Chain Variable Region Mutation C2G4 Clone of Clone MS502

The C2G4 clone having the most excellent value in the measurement of affinity among the light chain variable region mutations was selected and fixed as the final clone of the light chain variable region. Then, in order to combine, produce and purify the heavy chain variable region mutation antibodies 56, 2-30, 2-58, 2-73, and 2-78, Expi293F™ cells were inoculated at a concentration of $2.5 \times 10^6$ cell/mL the day before transfection. After incubation (37° C., 8% $CO_2$, 125 rpm) for 24 hours, Expi293™ expression medium (Cat.No.A1435101, Gibco) was added to prepare a product of 30 mL having a concentration of $2.5 \times 10^6$ cell/mL (viability=95%). 30 μg of DNA (pcIw-MS502 heavy chain variable region mutation antibody: 15 μg, pcIw-light chain variable region mutation C2G4: 15 μg) was diluted in an OptiPro™ SEM medium (Cat.No. 12309019, Gibco) so as to have a total volume of 1.5 mL, and reacted at room temperature for 5 minutes. 1.5 mL of the OptiPro™ SEM medium (Cat.No. 12309019, Gibco) was mixed with 80 μL of an Expi- Fectamine™ 293 reagent (Cat.No.A14524, Gibco) so that a total volume is 1.5 mL, and reacted at room temperature for 5 minutes. After the reaction for 5 minutes, 1.5 mL of diluted DNA and 1.5 mL of diluted ExpiFectamine™ 293 reagent were well-mixed with each other, and reacted at room temperature for 20 to 30 minutes. 3 mL of the mixture of DNA and ExpiFectamine™ 293 reagent was treated in the Expi293F™ cells. After suspension-culture (37° C., 8% $CO_2$, 125 rpm) for 16 to 18 hours, 150 µL of Expi-Fectamine™ 293 Enhancer 1 (Cat.No.A14524, Gibco) and 1.5 mL of ExpiFectamine™ 293 Enhancer2 (Cat-.No.A14524, Gibco) were added thereto, followed by suspension-culturing for 5 days. After the culturing, cell debris was removed by centrifugation at 4000 rpm for 20 minutes, and the supernatant passed through 0.22 µm filter to be prepared. MabSelect Xtra (Cat.No. 17-5269-02, GE Healthcare) which is protein A resin having 100 µL was prepared for each 30 mL of the culture fluid, followed by centrifugation at 1000 rpm for 2 minutes to remove a storage solution, and the obtained product was washed with 400 µL of protein A binding buffer (Cat.No. 21007, Pierce) 3 times. The protein A resin was added to the prepared culture fluid and rotation-reacted at room temperature for 30 minutes. The mixture of the culture fluid and the resin was put into a pierce spin column snap-cap (Cat.No. 69725, Thermo), and then, only the resin was left in the column using QIAvac 24 Plus (Cat.No. 19413, QIAGEN) vacuum manifold. 5 mL of protein A binding buffer was added to wash the resin, 200 µL of a protein A elution buffer (Cat.No. 21009, Pierce) was added thereto. The resultant material was reacted by resuspension at room temperature for 2 minutes, and centrifuged at 1000 rpm for 1 minute, and eluted. Each eluate was neutralized by adding 2.5 µL of 1.5M Tris-HCl (pH 9.0). The elution was performed 4 to 6 times, and each fraction was quantified by using Nanodrop 200C (Thermo scientific). The fractions in which protein is detected were collected, and exchanged with a PBS (Phosphate-Buffered Saline) buffer using Zeba Spin Desalting Columns, 7K MWCO, 5 mL (Cat.No. 0089892, Pierce). Then, protein electrophoresis (SDS-PAGE) was performed under reduction and non-reduction condition to finally verify the concentration quantification and the antibody state, and the antibody was kept at 4° C.

TABLE 15

| Clone | variable region | amino acid sequence | SEQ ID NO: |
|---|---|---|---|
| 56-C2G4 | heavy chain | EVQLLESGGGLVQPGGSLRLSCAASGFTFSN YAMSWVRQAPGKGLEWVSGIPPDSASKYY ADSVRGRFTVSRDNSKNTLYLQMNSLRAED TAVYYCAKNMLSFDYWGQGTLVTVSS | 113 |
| | light chain | QSVLTQPPSASGTPGQRVTISCTGSSSNIGSN AVSWYQQLPGTAPKLLIYYNSKRPSGVPDRF SGSKSGTSASLAISGLRSEDEADYYCGSWDP SLNGYVFGGGTKVTVLG | 110 |
| 2-30-C2G4 | heavy chain | EVQLLESGGGLVQPGGSLRLSCAASGFTFSN YAMSWVRQAPGKGLEWVSGIPPDSNSKYY ADSVRGRFTVSRDNSKNTLYLQMNSLRAED TAVYYCAKNMRTFDYWGQGTLVTVSS | 114 |
| | light chain | QSVLTQPPSASGTPGQRVTISCTGSSSNIGSN AVSWYQQLPGTAPKLLIYYNSKRPSGVPDRF SGSKSGTSASLAISGLRSEDEADYYCGSWDP SLNGYVFGGGTKVTVLG | 110 |
| 2-73-C2G4 | heavy chain | EVQLLESGGGLVQPGGSLRLSCAASGFTFSN YAMSWVRQAPGKGLEWVSGIPPNSDSKYY ADSVRGRFTVSRDNSKNTLYLQMNSLRAED TAVYYCAKNMLSFDYWGQGTLVTVSS | 115 |
| | light chain | QSVLTQPPSASGTPGQRVTISCTGSSSNIGSN AVSWYQQLPGTAPKLLIYYNSKRPSGVPDRF SGSKSGTSASLAISGLRSEDEADYYCGSWDP SLNGYVFGGGTKVTVLG | 110 |
| 2-78-C2G4 | heavy chain | EVQLLESGGGLVQPGGSLRLSCAASGFTFSN YAMSWVRQAPGKGLEWVSGIPPDSGSKYY ADSVRGRFTVSRDNSKNTLYLQMNSLRAED TAVYYCAKNMFSFDYWGQGTLVTVSS | 116 |
| | light chain | QSVLTQPPSASGTPGQRVTISCTGSSSNIGSN AVSWYQQLPGTAPKLLIYYNSKRPSGVPDRF SGSKSGTSASLAISGLRSEDEADYYCGSWDP SLNGYVFGGGTKVTVLG | 110 |

TABLE 16

| Clone | variable region | CDR1 | CDR2 | CDR3 |
|---|---|---|---|---|
| 56-C2G4 | heavy chain | NYAMS (SEQ ID NO: 59) | GIPPDSASKYYA DSVRG (SEQ ID NO: 122) | NMLSFDY (SEQ ID NO: 66) |

TABLE 16-continued

| Clone | variable region | CDR1 | CDR2 | CDR3 |
|---|---|---|---|---|
| | light chain | TGSSSNIGSNAVS(SEQ ID NO: 67) | YNSKRPS(SEQ ID NO: 68) | GSWDPSLNGYV(SEQ ID NO: 119) |
| 2-30-C2G4 | heavy chain | NYAMS(SEQ ID NO: 59) | GIPPDSNSKYYADSVRG(SEQ ID NO: 123) | NMRTFDY(SEQ ID NO: 124) |
| | light chain | TGSSSNIGSNAVS(SEQ ID NO: 67) | YNSKRPS(SEQ ID NO: 68) | GSWDPSLNGYV(SEQ ID NO: 120) |
| 2-73-C2G4 | heavy chain | NYAMS(SEQ ID NO: 59) | GIPPNSDSKYYADSVRG(SEQ ID NO: 125) | NMLSFDY(SEQ ID NO: 66) |
| | light chain | TGSSSNIGSNAVS(SEQ ID NO: 67) | YNSKRPS(SEQ ID NO: 68) | GSWDPSLNGYV(SEQ ID NO: 119) |
| 2-78-C2G4 | heavy chain | NYAMS(SEQ ID NO: 59) | GIPPDSGSKYYADSVRG(SEQ ID NO: 65) | NMFSFDY(SEQ ID NO: 126) |
| | light chain | TGSSSNIGSNAVS(SEQ ID NO: 67) | YNSKRPS(SEQ ID NO: 68) | GSWDPSLNGYV (SEQ ID NO: 119) |

3-14: Measurement of Quantitative Binding Force of MS502 Heavy Chain Variable Region Mutation Antibody and Combination of C2G4 and Heavy Chain Variable Region Mutation Antibody with Regard to MSLN Antigen The quantitative binding force (affinity) of each of the purified anti-MSLN antibodies, i.e., MS502 clone heavy chain variable region mutation antibodies 56, 2-30, 2-73, 2-78, and the combination antibodies of the C2G4 light chain variable region and the heavy chain variable region mutation antibodies including 56-C2G4, 2-30-C2G4, 2-73-C2G4, 2-78-C2G4 with regard to recombinant human mesothelin (MSLN) was measured by using a Biacore T-200 (GE Healthcare, U.S.A.) biosensor. The MSLN (Cat.No. 3265-MS, R&D systems, U.S.A.) purified from the HEK293 cells was fixed to a CM5 chip (GE Healthcare, CAT. No. BR-1005-30) so as to satisfy 200 Rmax by using an amine-carboxylic reaction. Then, the clone 56 antibody, the clone 2-30 antibody, the clone 2-73 antibody, the clone 2-78 antibody, the clone 56-C2G4 antibody, the clone 2-30-C2G4 antibody, the clone 2-73-C2G4 antibody, and the clone 2-78-C2G4 antibody serially diluted with HBS-EP buffer (10 mM HEPES, pH7.4, 150 mM NaCl, 3 mM EDTA, 0.005% surfactant P20) were allowed to flow at a concentration range of 0.078 nM to 5 nM and at a flow rate of 30 µL/min for association of 120 seconds and dissociation of 1800 seconds. The dissociation of the antibody bound to the MSLN was induced by flowing 10 mM Glycine-HCl pH 1.5 at a flow rate of 30 µL/min for 30 seconds (Table 17). The affinity was obtained as movement speed constants ($K_{on}$ and $K_{off}$) and an equilibrium dissociation constant ($K_D$) by using a Biacore T-200 evaluation software (Table 18).

TABLE 17

| | |
|---|---|
| SPR | Biacore T200 |
| Chip | CM5 |
| Running Buffer | HBS-EP pH 7.4 |
| Flow rate | 30 µL/min |
| Association/dissociation time | 120 sec/600 sec |
| IgG Conc. | 0.078~5 nM, ½ serial dilution |
| Regeneration | 10 mM Glycine-HCl pH 1.5, 30 sec |

TABLE 18

| | $K_{on}$ | $K_{off}$ | $K_D$ |
|---|---|---|---|
| 56 | $1.26 \times 10^7$ | $1.57 \times 10^{-3}$ | $1.25 \times 10^{-10}$ |
| 2-30 | $1.92 \times 10^8$ | $3.19 \times 10^{-2}$ | $1.66 \times 10^{-10}$ |
| 2-78 | $1.50 \times 10^8$ | $2.44 \times 10^{-3}$ | $1.63 \times 10^{-11}$ |
| 56 - C2G4 | $6.61 \times 10^7$ | $1.08 \times 10^{-2}$ | $1.63 \times 10^{-10}$ |
| 2-30 - C2G4 | $1.15 \times 10^8$ | $2.70 \times 10^{-2}$ | $2.34 \times 10^{-10}$ |
| 2-73 - C2G4 | $8.98 \times 10^7$ | $1.48 \times 10^{-2}$ | $1.65 \times 10^{-10}$ |
| 2-78 - C2G4 | $2.10 \times 10^8$ | $7.82 \times 10^{-3}$ | $3.72 \times 10^{-11}$ |

Example 4: FACS Analysis of Anti-MSLN Antibody Binding to MSLN-Expressing Cancer Cell In order to evaluate whether the anti-MSLN antibody derived from the immune and synthetic library is selectively bound to the MSLN-expressing cell, an expression amount of the MSLN was measured in a cancer cell line, and the antibody binding each cell was confirmed by FACS test.

4-1: Construction of MSLN-Expressing Cell Line

Figure 4:
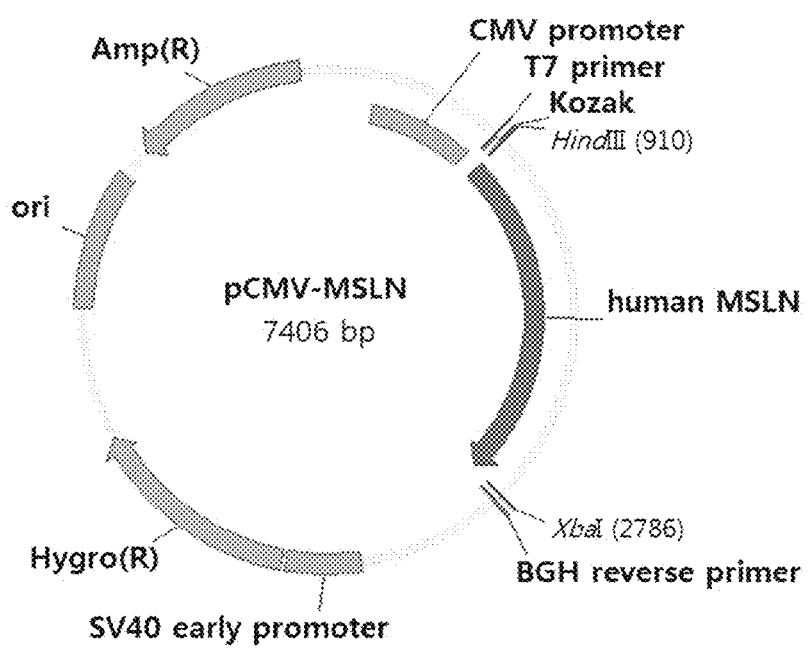
FIG. 4 illustrates a vector for expressing the MSLN in a cell line.

The plasmid (pCMV/MSLN) containing the MSLN expressing unit and hygromycin resistant gene was delivered into MiaPaCa-2 pancreatic cancer cell confirmed as an MSLN negative cell line, by using a jetPEI(polyethyleneimine) transfection system (Polyplus, 101-40) (FIG. 4). After 48 hours, the cell culture fluid was replaced with a culture fluid containing hygromycin B (200 µg/mL). 10 colonies having resistance against the hygromycin were obtained while exchanging the culture fluid every 3 days, to confirm each MSLN expression amount by a Western blotting method. With respect to four kinds of pancreatic cancer cell lines (MiaPaCa-2, BxPC-3, Capan-1, AsPC-1) and two kinds of mesothelioma cell lines (H28, H2452), the MSLN expression amount in the cells was confirmed by using the anti-MSLN antibody (#133489, Abcam) through the Western blotting method. The culturing cells were separated by adding a Tryple Express solution and stored in a 15 mL tube, followed by centrifugation at 2000 rpm at room temperature for 3 minutes to decant the culture fluid, and the obtained product was suspended with 100 μL 1×SDS-PAGE sample buffer (50 mM Tris(pH6.8), 2% SDS, 100 mM DTT (dithiothreitol), 0.1% BPB(bromophenol blue), 10% glycerol) and heated for 5 minutes. The obtained product was centrifuged to collect the supernatant, followed by electrophoresis in 4-12% SDS-PAGE, at 20 mA for about 2 hours, and a transfer unit was used to transfer the separated protein to a PVDF membrane, and then, electrophoresis was performed at 300 mA with tris-glycine buffer (39 mM glycine, 48 mM tris, 0.037% SDS, 20% methanol) for about 90 minutes. The PVDF membrane in which the protein was transferred was subjected to blocking at room temperature for 1 hour by using a TBS blocking solution. The anti-MSLN antibody (#133489, Abcam) as the primary antibody was diluted by 1:2,000 with 5% skim milk/1×TBST buffer, and reacted at room temperature for about 1 hour, and washed with 1×TBST buffer 6 times every 5 minutes. The anti-mouse HRP (KPL, MA, U.S.A.) as the secondary antibody was diluted by 1:20,000 with 5% skim milk/1×TBST buffer, and reacted for 30 minutes, and washed with 1×TBST buffer 6 times every 5 minutes. Then, the MSLN protein band was verified by color development reaction solution (ECL, Amersham, UK).

As a result, as illustrated in FIG. 5, it was confirmed that H28, MiaPaCa-2, BxPC-3, Capan-1 cell lines are MSLN-negative, and H226, H2452(H2052), AsPC-1 are MSLN-positive by measuring whether there are the MSLN having 70 kDa precursor form and 40 to 50 kDa mature form from each cancer cell line.

Figure 6:
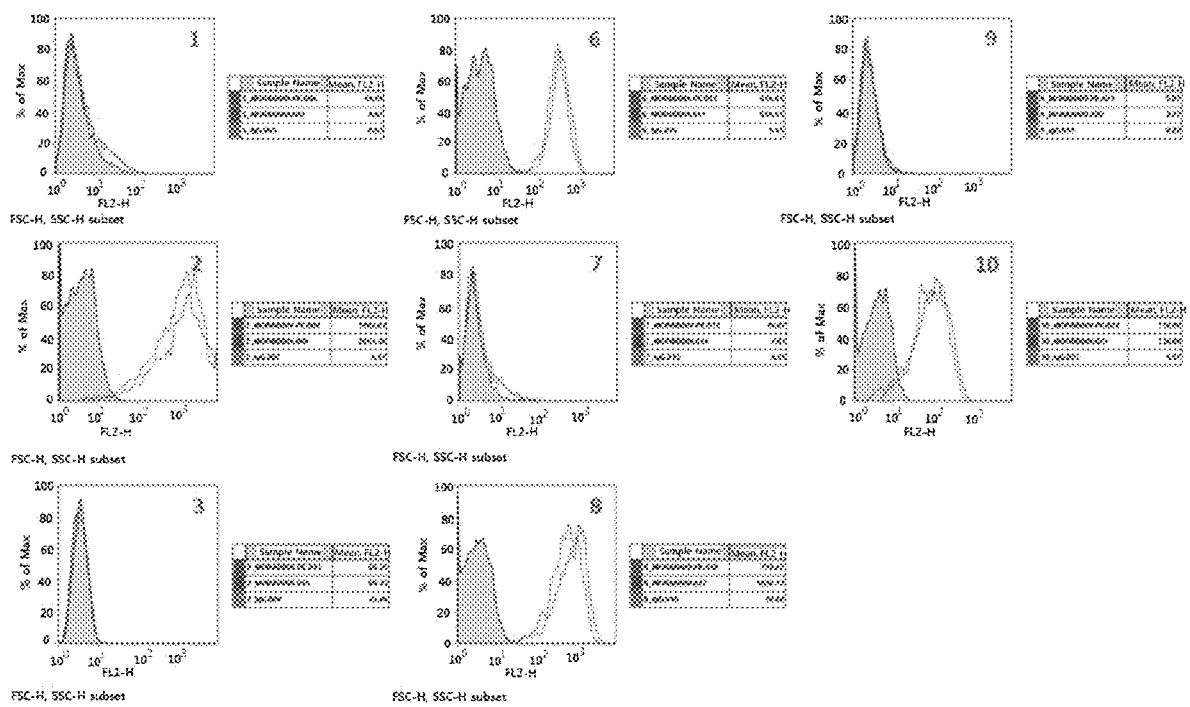
FIG. 6 illustrates analysis of an MSLN expression amount of cell lines and tumor cell lines expressing the MSLN.

4-2: MSLN Expression Amount Analysis in MSLN-Expressing Cell Lines and MSLN-Expressing Tumor Cell Lines FACS test was performed on the MSLN present in the cell surface with regard to MiaPaCa-MSLN which is a cell line in which the MSLN was artificially expressed. Cells to be analyzed that were grown in a culture dish were separated by adding a Tryple Express solution and stored in a 50 mL tube, followed by centrifugation at 2000 rpm at room temperature for 3 minutes to decant the culture fluid, and the obtained product was washed once with PBS. The cells were suspended with FACS buffer, and transferred to a round bottom tube and centrifuged at 2000 rpm at room temperature for 3 minutes. The supernatant was discarded and the cells were well-loosened with the FACS buffer so as to have a cell density of 4×10⁵/mL. Then, 1 μg of candidate antibody was added thereto at 4° C. After 1 hour, the resultant material was washed with the FACS buffer twice, and goat-derived anti-human IgG antibody (FITC junction) was added in an amount of 1 μL for each sample to be combined at 4° C. for 30 minutes. The cells were collected by centrifugation at 2000 rpm for 3 minutes, and 500 μL of fixation buffer was added to resuspend the cells, and the cells were measured by FACS calibur (FIG. 6).

Figure 7:
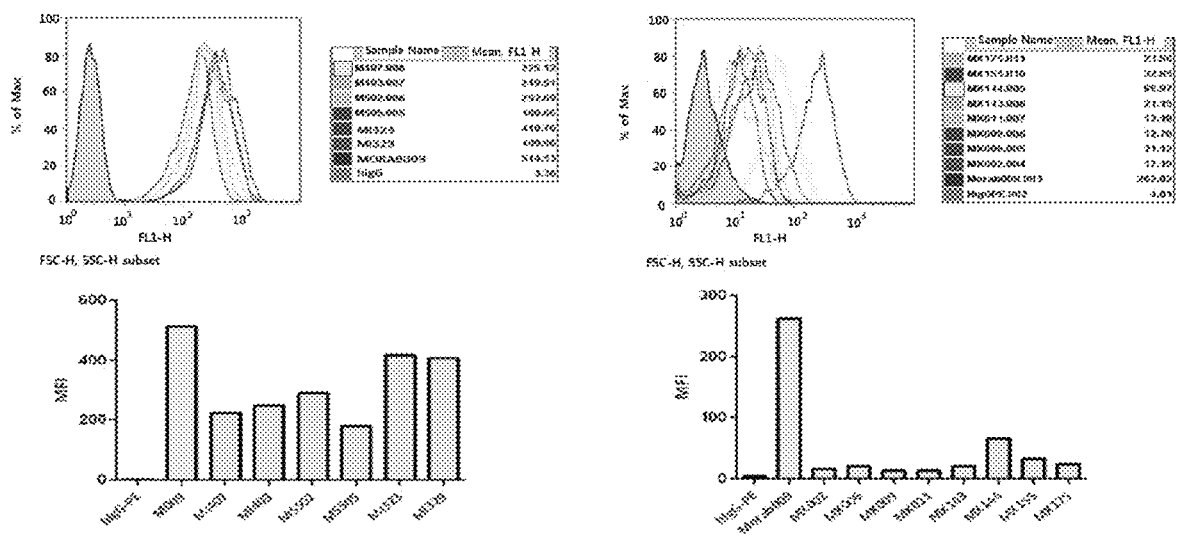
FIG. 7 illustrates selective binding analysis with regard to the cell lines expressing the MSLN by using an anti-mesothelin (MSLN) antibody of the present invention.

4-3: Selective Binding Analysis of Anti-MSLN Antibody with Regard to MSLN-Expressing Cell Line The FACS test was performed to evaluate whether the anti-MSLN antibody was selectively bound to the MSLN-overexpressing cell line (MiaPaCa-MSLN #2). The anti-MSLN candidate antibody was labeled by the method described in Example 4-2 above, and the cells were measured by FACS calibur (FIG. 7).

The FACS test was performed to evaluate whether the MI323, MI329, MI403, and MS502 candidate antibodies having excellent binding force were well-bound even to the cell line MSLN of mesothelioma (H226, H2052) and pancreatic cancer (AsPC-1), and results were compared with MFI values.

TABLE 19

| MSLN Ab | Miapaca2 | H226 | ASPC-1 | H2052 |
| --- | --- | --- | --- | --- |
| MSLN test | − | + | + | + + |
| MS502 | − | + + | + + | + + |
| MI403 | − | + | + + | + + |
| MI323 | − | + + + | + + | + + |
| MI329 | − | + + + | + + | + + |
| Morab | − | + + + | + + | + + |
| BAY94-9343 | − | + + + | + + | + + |

As a result, as shown in FIG. 8 and Table 19, all of the MI323, MI329, MI403, and MS502 candidate antibodies with regard to the MSLN of mesothelioma and pancreatic cancer cell lines had significant binding force even though there is a slight difference in binding degree. In particular, the MI323 candidate antibody had an excellent binding aspect.

Further, whether the MI323 candidate antibody having the excellent binding aspect with regard to the MSLN, MS502 candidate antibody having a different pattern of Biacore $K_D(K_{off}/K_{on})$ value, and the heavy chain variable region mutation 2-78-C2G4 candidate antibody produced from the MS502 candidate antibody were selectively bound to MSLN-expressing tumor cells, was evaluated in MiaPaCa-MSLN #2 cell that over-expresses the MSLN and MiaPaCa-2 that does not over-express the MSLN.

As a result, as illustrated in FIG. 9, the MI323, MS502, and 2-78-C2G4 candidate antibodies had excellent binding aspect in the MSLN-overexpressing MiaPaCa-MSLN #2 cell as compared to the MiaPaCa-2.

INDUSTRIAL APPLICABILITY

The antibody specifically bound to the mesothelin according to the present invention has high affinity and specificity to an antigen to be effectively usable for treatment or diagnosis of cancer or tumor diseases.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention will be defined by the accompanying claims and their equivalents.

SEQUENCE LISTING FREE TEXT

Attached electronic file.

The invention claimed is:

1. An antibody binding to mesothelin comprising
a heavy chain variable region comprising a heavy chain CDR1 comprising the amino acid sequence of SEQ ID NO: 9, a heavy chain CDR2 comprising the amino acid sequence of SEQ ID NO: 10, and a heavy chain CDR3 comprising the amino acid sequence of SEQ ID NO: 11, and a light chain variable region comprising a light chain CDR1 comprising the amino acid sequence of SEQ ID NO: 12, a light chain CDR2 comprising the amino acid sequence of SEQ ID NO: 13 and a light chain CDR3 comprising the amino acid sequence of SEQ ID NO: 14;
a heavy chain variable region comprising a heavy chain CDR1 comprising the amino acid sequence of SEQ ID NO: 15, a heavy chain CDR2 comprising the amino acid sequence of SEQ ID NO: 16, and a heavy chain CDR3 comprising the amino acid sequence of SEQ ID NO: 17, and a light chain variable region comprising a light chain CDR1 comprising the amino acid sequence of SEQ ID NO: 18, a light chain CDR2 comprising the amino acid sequence of SEQ ID NO: 19 and a light chain CDR3 comprising the amino acid sequence of SEQ ID NO: 20;
a heavy chain variable region comprising a heavy chain CDR1 comprising the amino acid sequence of SEQ ID NO: 21, a heavy chain CDR2 comprising the amino acid sequence of SEQ ID NO: 22, and a heavy chain CDR3 comprising the amino acid sequence of SEQ ID NO: 23, and a light chain variable region comprising a light chain CDR1 comprising the amino acid sequence of SEQ ID NO: 24, a light chain CDR2 comprising the amino acid sequence of SEQ ID NO: 25 and a light chain CDR3 comprising the amino acid sequence of SEQ ID NO: 26;
a heavy chain variable region comprising a heavy chain CDR1 comprising the amino acid sequence of SEQ ID NO: 27, a heavy chain CDR2 comprising the amino acid sequence of SEQ ID NO: 28, and a heavy chain CDR3 comprising the amino acid sequence of SEQ ID NO: 29, and a light chain variable region comprising a light chain CDR1 comprising the amino acid sequence of SEQ ID NO: 30, a light chain CDR2 comprising the amino acid sequence of SEQ ID NO: 25 and a light chain CDR3 comprising the amino acid sequence of SEQ ID NO: 26;
a heavy chain variable region comprising a heavy chain CDR1 comprising the amino acid sequence of SEQ ID NO: 59, a heavy chain CDR2 comprising the amino acid sequence of SEQ ID NO: 60, and a heavy chain CDR3 comprising the amino acid sequence of SEQ ID NO: 61, and a light chain variable region comprising a light chain CDR1 comprising the amino acid sequence of SEQ ID NO: 62, a light chain CDR2 comprising the amino acid sequence of SEQ ID NO: 63 and a light chain CDR3 comprising the amino acid sequence of SEQ ID NO: 64;
a heavy chain variable region comprising a heavy chain CDR1 comprising the amino acid sequence of SEQ ID NO: 59, a heavy chain CDR2 comprising the amino acid sequence of SEQ ID NO: 65, and a heavy chain CDR3 comprising the amino acid sequence of SEQ ID NO: 66, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 69;
a heavy chain variable region comprising a heavy chain CDR1 comprising the amino acid sequence of SEQ ID NO: 59, a heavy chain CDR2 comprising the amino acid sequence of SEQ ID NO: 65, and a heavy chain CDR3 comprising the amino acid sequence of SEQ ID NO: 66, and a light chain variable region comprising a light chain CDR1 comprising the amino acid sequence of SEQ ID NO: 70, a light chain CDR2 comprising the amino acid sequence of SEQ ID NO: 68 and a light chain CDR3 comprising the amino acid sequence of SEQ ID NO: 69;
a heavy chain variable region comprising a heavy chain CDR1 comprising the amino acid sequence of SEQ ID NO: 59, a heavy chain CDR2 comprising the amino acid sequence of SEQ ID NO: 71, and a heavy chain CDR3 comprising the amino acid sequence of SEQ ID NO: 72, and a light chain variable region comprising a light chain CDR1 comprising the amino acid sequence of SEQ ID NO: 62, a light chain CDR2 comprising the amino acid sequence of SEQ ID NO: 73 and a light chain CDR3 comprising the amino acid sequence of SEQ ID NO: 74;
a heavy chain variable region comprising a heavy chain CDR1 comprising the amino acid sequence of SEQ ID NO: 59, a heavy chain CDR2 comprising the amino acid sequence of SEQ ID NO: 75, and a heavy chain CDR3 comprising the amino acid sequence of SEQ ID NO: 76, and a light chain variable region comprising a light chain CDR1 comprising the amino acid sequence of SEQ ID NO: 77, a light chain CDR2 comprising the amino acid sequence of SEQ ID NO: 78 and a light chain CDR3 comprising the amino acid sequence of SEQ ID NO: 79;
a heavy chain variable region comprising a heavy chain CDR1 comprising the amino acid sequence of SEQ ID NO: 59, a heavy chain CDR2 comprising the amino acid sequence of SEQ ID NO: 80, and a heavy chain CDR3 comprising the amino acid sequence of SEQ ID NO: 81, and a light chain variable region comprising a light chain CDR1 comprising the amino acid sequence of SEQ ID NO: 62, a light chain CDR2 comprising the amino acid sequence of SEQ ID NO: 82 and a light chain CDR3 comprising the amino acid sequence of SEQ ID NO: 83;
a heavy chain variable region comprising a heavy chain CDR1 comprising the amino acid sequence of SEQ ID NO: 59, a heavy chain CDR2 comprising the amino acid sequence of SEQ ID NO: 84, and a heavy chain CDR3 comprising the amino acid sequence of SEQ ID NO: 85, and a light chain variable region comprising a light chain CDR1 comprising the amino acid sequence of SEQ ID NO: 86, a light chain CDR2 comprising the amino acid sequence of SEQ ID NO: 78 and a light chain CDR3 comprising the amino acid sequence of SEQ ID NO: 87;

a heavy chain variable region comprising a heavy chain CDR1 comprising the amino acid sequence of SEQ ID NO: 59, a heavy chain CDR2 comprising the amino acid sequence of SEQ ID NO: 65, and a heavy chain CDR3 comprising the amino acid sequence of SEQ ID NO: 66, and a light chain variable region comprising a light chain CDR1 comprising the amino acid sequence of SEQ ID NO: 117, a light chain CDR2 comprising the amino acid sequence of SEQ ID NO: 68 and a light chain CDR3 comprising the amino acid sequence of SEQ ID NO: 118;

a heavy chain variable region comprising a heavy chain CDR1 comprising the amino acid sequence of SEQ ID NO: 59, a heavy chain CDR2 comprising the amino acid sequence of SEQ ID NO: 65, and a heavy chain CDR3 comprising the amino acid sequence of SEQ ID NO: 66, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 119;

a heavy chain variable region comprising a heavy chain CDR1 comprising the amino acid sequence of SEQ ID NO: 59, a heavy chain CDR2 comprising the amino acid sequence of SEQ ID NO: 65, and a heavy chain CDR3 comprising the amino acid sequence of SEQ ID NO: 66, and a light chain variable region comprising a light chain CDR1 comprising the amino acid sequence of SEQ ID NO: 117, a light chain CDR2 comprising the amino acid sequence of SEQ ID NO: 68 and a light chain CDR3 comprising the amino acid sequence of SEQ ID NO: 120;

a heavy chain variable region comprising a heavy chain CDR1 comprising the amino acid sequence of SEQ ID NO: 59, a heavy chain CDR2 comprising the amino acid sequence of SEQ ID NO: 121, and a heavy chain CDR3 comprising the amino acid sequence of SEQ ID NO: 66, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 69;

a heavy chain variable region comprising a heavy chain CDR1 comprising the amino acid sequence of SEQ ID NO: 59, a heavy chain CDR2 comprising the amino acid sequence of SEQ ID NO: 122, and a heavy chain CDR3 comprising the amino acid sequence of SEQ ID NO: 66, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 69;

a heavy chain variable region comprising a heavy chain CDR1 comprising the amino acid sequence of SEQ ID NO: 59, a heavy chain CDR2 comprising the amino acid sequence of SEQ ID NO: 123, and a heavy chain CDR3 comprising the amino acid sequence of SEQ ID NO: 124, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 69;

a heavy chain variable region comprising a heavy chain CDR1 comprising the amino acid sequence of SEQ ID NO: 59, a heavy chain CDR2 comprising the amino acid sequence of SEQ ID NO: 125, and a heavy chain CDR3 comprising the amino acid sequence of SEQ ID NO: 66, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 69;

a heavy chain variable region comprising a heavy chain CDR1 comprising the amino acid sequence of SEQ ID NO: 59, a heavy chain CDR2 comprising the amino acid sequence of SEQ ID NO: 65, and a heavy chain CDR3 comprising the amino acid sequence of SEQ ID NO: 126, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 69;

a heavy chain variable region comprising a heavy chain CDR1 comprising the amino acid sequence of SEQ ID NO: 59, a heavy chain CDR2 comprising the amino acid sequence of SEQ ID NO: 122, and a heavy chain CDR3 comprising the amino acid sequence of SEQ ID NO: 66, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 119;

a heavy chain variable region comprising a heavy chain CDR1 comprising the amino acid sequence of SEQ ID NO: 59, a heavy chain CDR2 comprising the amino acid sequence of SEQ ID NO: 123, and a heavy chain CDR3 comprising the amino acid sequence of SEQ ID NO: 124, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 120;

a heavy chain variable region comprising a heavy chain CDR1 comprising the amino acid sequence of SEQ ID NO: 59, a heavy chain CDR2 comprising the amino acid sequence of SEQ ID NO: 125, and a heavy chain CDR3 comprising the amino acid sequence of SEQ ID NO: 66, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 119; or a heavy chain variable region comprising a heavy chain CDR1 comprising the amino acid sequence of SEQ ID NO: 59, a heavy chain CDR2 comprising the amino acid sequence of SEQ ID NO: 65, and a heavy chain CDR3 comprising the amino acid sequence of SEQ ID NO: 126, and a light chain variable region comprising a light chain CDR1 comprising the amino acid sequence of SEQ ID NO: 67, a light chain CDR2 comprising the amino acid sequence of SEQ ID NO: 68 and a light chain CDR3 comprising the amino acid sequence of SEQ ID NO: 119.

2. The antibody of claim 1, wherein the heavy chain variable region comprises the amino acid sequence of SEQ ID NO: 1, 3, 5, 7, 46, 48, 51, 53, 55, 57, 112, 113, 114, 115 or 116.

3. The antibody of claim 1, wherein the light chain variable region comprises the amino acid sequence of SEQ ID NO: 2, 4, 6, 8, 47, 49, 50, 52, 54, 56, 58, 109, 110 or 111.

4. The antibody of claim 1 comprising:
- a heavy chain variable region comprising the amino acid sequence of SEQ ID NO: 1, and a light chain variable region comprising the amino acid sequence of SEQ ID NO: 2;
- a heavy chain variable region comprising the amino acid sequence of SEQ ID NO: 3, and a light chain variable region comprising the amino acid sequence of SEQ ID NO: 4;
- a heavy chain variable region comprising the amino acid sequence of SEQ ID NO: 5, and a light chain variable region comprising the amino acid sequence of SEQ ID NO: 6;
- a heavy chain variable region comprising the amino acid sequence of SEQ ID NO: 7, and a light chain variable region comprising the amino acid sequence of SEQ ID NO: 8;
- a heavy chain variable region comprising the amino acid sequence of SEQ ID NO: 46, and a light chain variable region comprising the amino acid sequence of SEQ ID NO: 47;
- a heavy chain variable region comprising the amino acid sequence of SEQ ID NO: 48, and a light chain variable region comprising the amino acid sequence of SEQ ID NO: 49;
- a heavy chain variable region comprising the amino acid sequence of SEQ ID NO: 48, and a light chain variable region comprising the amino acid sequence of SEQ ID NO: 50;
- a heavy chain variable region comprising the amino acid sequence of SEQ ID NO: 51, and a light chain variable region comprising the amino acid sequence of SEQ ID NO: 52;
- a heavy chain variable region comprising the amino acid sequence of SEQ ID NO: 53, and a light chain variable region comprising the amino acid sequence of SEQ ID NO: 54;
- a heavy chain variable region comprising the amino acid sequence of SEQ ID NO: 55, and a light chain variable region comprising the amino acid sequence of SEQ ID NO: 56;
- a heavy chain variable region comprising the amino acid sequence of SEQ ID NO: 57, and a light chain variable region comprising the amino acid sequence of SEQ ID NO: 58;
- a heavy chain variable region comprising the amino acid sequence of SEQ ID NO: 48, and a light chain variable region comprising the amino acid sequence of SEQ ID NO: 109;
- a heavy chain variable region comprising the amino acid sequence of SEQ ID NO: 48, and a light chain variable region comprising the amino acid sequence of SEQ ID NO: 110;
- a heavy chain variable region comprising the amino acid sequence of SEQ ID NO: 48, and a light chain variable region comprising the amino acid sequence of SEQ ID NO: 111;
- a heavy chain variable region comprising the amino acid sequence of SEQ ID NO: 112, and a light chain variable region comprising the amino acid sequence of SEQ ID NO: 49;
- a heavy chain variable region comprising the amino acid sequence of SEQ ID NO: 113, and a light chain variable region comprising the amino acid sequence of SEQ ID NO: 49;
- a heavy chain variable region comprising the amino acid sequence of SEQ ID NO: 114, and a light chain variable region comprising the amino acid sequence of SEQ ID NO: 49;
- a heavy chain variable region comprising the amino acid sequence of SEQ ID NO: 115, and a light chain variable region comprising the amino acid sequence of SEQ ID NO: 49;
- a heavy chain variable region comprising the amino acid sequence of SEQ ID NO: 116, and a light chain variable region comprising the amino acid sequence of SEQ ID NO: 49;
- a heavy chain variable region comprising the amino acid sequence of SEQ ID NO: 113, and a light chain variable region comprising the amino acid sequence of SEQ ID NO: 110;
- a heavy chain variable region comprising the amino acid sequence of SEQ ID NO: 114, and a light chain variable region comprising the amino acid sequence of SEQ ID NO: 110;
- a heavy chain variable region comprising the amino acid sequence of SEQ ID NO: 115, and a light chain variable region comprising the amino acid sequence of SEQ ID NO: 110; or
- a heavy chain variable region comprising the amino acid sequence of SEQ ID NO: 116, and a light chain variable region comprising the amino acid sequence of SEQ ID NO: 110.

5. A nucleic acid encoding the antibody according to claim 1.

6. A vector comprising the nucleic acid according to claim 5.

7. A host cell comprising the vector according to claim 6.

8. A method of preparing an antibody comprising expressing the antibody by culturing the host cell according to claim 7.

9. A pharmaceutical composition for treating cancer or a tumor comprising the antibody according to claim 1 as an active ingredient.

10. A method of treating a mesothelin overexpressing cancer or tumor comprising administering an effective amount of the antibody according to claim 1 to an animal.

11. A pharmaceutical composition for treating cancer or a tumor comprising the antibody according to claim 4 as an active ingredient.

12. A method of treating a mesothelin overexpressing cancer or tumor comprising administering an effective amount of the antibody according to claim 4 to an animal.

13. A nucleic acid encoding the antibody according to claim 4.

14. A vector comprising the nucleic acid according to claim 13.

15. A host cell comprising the vector according to claim 14.

* * * * *

SEQUENCE LISTING

```
<160> NUMBER OF SEQ ID NOS: 127

<210> SEQ ID NO 1
<211> LENGTH: 119
<212> TYPE: PRT
<213> ORGANISM: Artificial Sequence
<220> FEATURE:
<223> OTHER INFORMATION: clone MI323_Variable heavy chain
```

-continued

<400> SEQUENCE: 1

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Ser Phe Thr Ser Tyr
            20                  25                  30

Phe Ile Gln Trp Val Lys Gln Arg Pro Gly Gln Gly Leu Glu Trp Ile
        35                  40                  45

Gly Trp Ile Phe Pro Gly Ser Gly Asn Thr Lys Tyr Asn Glu Met Phe
    50                  55                  60

Lys Gly Lys Ala Thr Leu Ala Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Gly Gly Tyr Gln Tyr Tyr Phe Asp Tyr Trp Gly Gln Gly
            100                 105                 110

Thr Ser Val Thr Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: clone MI323_Variable light chain

<400> SEQUENCE: 2

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Pro Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg
            100                 105

<210> SEQ ID NO 3
<211> LENGTH: 118
<212> TYPE: PRT
<213> ORGANISM: Artificial Sequence
<220> FEATURE:
<223> OTHER INFORMATION: clone MI329_Variable heavy chain

<400> SEQUENCE: 3

Glu Val Met Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Arg Thr Pro Glu Lys Arg Leu Glu Trp Val
        35                  40                  45

Ala Thr Ile Asn Ser Asp Gly Ser Tyr Thr Phe Tyr Pro Asp Ser Val
    50                  55                  60

```
Lys Gly Arg Phe Thr Ile Ser Arg Asp Asn Ala Lys Asn Thr Leu Tyr
 65                  70                  75                  80

Leu Gln Met Asn Ser Leu Arg Ser Glu Asp Thr Ala Met Tyr Tyr Cys
                 85                  90                  95

Ala Arg Trp Gly Glu Asn Trp Tyr Phe Asp Val Trp Gly Ala Gly Thr
            100                 105                 110

Thr Val Thr Val Ser Ser
            115

<210> SEQ ID NO 4
<211> LENGTH: 113
<212> TYPE: PRT
<213> ORGANISM: Artificial Sequence
<220> FEATURE:
<223> OTHER INFORMATION: clone MI329_Variable light chain

<400> SEQUENCE: 4

Asp Val Val Met Thr Gln Thr Pro Leu Ser Leu Pro Val Ser Leu Gly
 1               5                  10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Phe Cys Ser Gln Ser
                 85                  90                  95

Thr His Phe Pro Arg Thr Phe Gly Gly Ala Thr Lys Leu Glu Leu Lys
            100                 105                 110

Arg

<210> SEQ ID NO 5
<211> LENGTH: 122
<212> TYPE: PRT
<213> ORGANISM: Artificial Sequence
<220> FEATURE:
<223> OTHER INFORMATION: clone MI403_Variable heavy chain

<400> SEQUENCE: 5

Glu Val Gln Val Val Glu Ser Gly Gly Gly Leu Val Lys Pro Gly Gly
 1               5                  10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
            35                  40                  45

Ala Tyr Ile Ser Ser Gly Gly Gly Ser Thr Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Met Tyr Tyr Cys
                 85                  90                  95

Ala Arg Gln Gly Thr Ala Val Lys Asn Tyr Trp Tyr Phe Asp Val Trp
            100                 105                 110

Gly Ala Gly Thr Ser Val Thr Val Ser Ser
            115                 120
```

```
<210> SEQ ID NO 6
<211> LENGTH: 112
<212> TYPE: PRT
<213> ORGANISM: Artificial Sequence
<220> FEATURE:
<223> OTHER INFORMATION: clone MI403_Variable light chain

<400> SEQUENCE: 6

Asp Ile Val Met Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Ser Ser Tyr Val His Trp Tyr Gln Gln Arg Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Gly Thr Tyr Tyr Cys Gln His Ser Trp
                85                  90                  95

Glu Ile Pro Phe Thr Phe Gly Ser Gly Thr Lys Leu Glu Ile Lys Arg
            100                 105                 110

<210> SEQ ID NO 7
<211> LENGTH: 122
<212> TYPE: PRT
<213> ORGANISM: Artificial Sequence
<220> FEATURE:
<223> OTHER INFORMATION: clone MI407_Variable heavy chain

<400> SEQUENCE: 7

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Pro Phe Ser Asn Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Asn Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Phe Cys
                85                  90                  95

Val Arg Gln Gly Thr Ser Val Glu Ser Tyr Trp Tyr Phe Asp Val Trp
            100                 105                 110

Gly Ala Gly Thr Thr Val Thr Val Ser Ser
        115                 120

<210> SEQ ID NO 8
<211> LENGTH: 112
<212> TYPE: PRT
<213> ORGANISM: Artificial Sequence
<220> FEATURE:
<223> OTHER INFORMATION: clone MI407_Variable light chain

<400> SEQUENCE: 8

Asp Ile Val Leu Thr Gln Ser Pro Ala Ser Leu Ala Val Ser Leu Gly
1               5                   10                  15
```

```
Gln Arg Ala Thr Ile Ser Cys Arg Ala Ser Gln Ser Val Ser Thr Ser
                20                  25                  30

Ser Ser Ser Tyr Ile His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Asp Asp Thr Ala Thr Tyr Tyr Cys Gln His Ser Trp
                85                  90                  95

Glu Ile Pro Phe Thr Phe Gly Ser Gly Thr Glu Leu Glu Ile Lys Arg
            100                 105                 110

<210> SEQ ID NO 9
<211> LENGTH: 5
<212> TYPE: PRT
<213> ORGANISM: Artificial Sequence
<220> FEATURE:
<223> OTHER INFORMATION: clone MI323_Variable heavy chain CDR1

<400> SEQUENCE: 9

Ser Tyr Phe Ile Gln
1               5

<210> SEQ ID NO 10
<211> LENGTH: 17
<212> TYPE: PRT
<213> ORGANISM: Artificial Sequence
<220> FEATURE:
<223> OTHER INFORMATION: clone MI323_Variable heavy chain CDR2

<400> SEQUENCE: 10

Trp Ile Phe Pro Gly Ser Gly Asn Thr Lys Tyr Asn Glu Met Phe Lys
1               5                   10                  15

Gly

<210> SEQ ID NO 11
<211> LENGTH: 10
<212> TYPE: PRT
<213> ORGANISM: Artificial Sequence
<220> FEATURE:
<223> OTHER INFORMATION: clone MI323_Variable heavy chain CDR3

<400> SEQUENCE: 11

Ser Gly Gly Tyr Gln Tyr Tyr Phe Asp Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: clone MI323_Variable light chain CDR1

<400> SEQUENCE: 12

Lys Ala Ser Gln Asp Val Ser Thr Ala Val Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: clone MI323_Variable light chain CDR2
```

```
<400> SEQUENCE: 13

Ser Ala Ser Tyr Arg Tyr Pro
1               5

<210> SEQ ID NO 14
<211> LENGTH: 9
<212> TYPE: PRT
<213> ORGANISM: Artificial Sequence
<220> FEATURE:
<223> OTHER INFORMATION: clone MI323_Variable light chain CDR3

<400> SEQUENCE: 14

Gln Gln His Tyr Ser Thr Pro Trp Thr
1               5

<210> SEQ ID NO 15
<211> LENGTH: 5
<212> TYPE: PRT
<213> ORGANISM: Artificial Sequence
<220> FEATURE:
<223> OTHER INFORMATION: clone MI329_Variable heavy chain CDR1

<400> SEQUENCE: 15

Ser Tyr Ala Met Ser
1               5

<210> SEQ ID NO 16
<211> LENGTH: 17
<212> TYPE: PRT
<213> ORGANISM: Artificial Sequence
<220> FEATURE:
<223> OTHER INFORMATION: clone MI329_Variable heavy chain CDR2

<400> SEQUENCE: 16

Thr Ile Asn Ser Asp Gly Ser Tyr Thr Phe Tyr Pro Asp Ser Val Lys
1               5                   10                  15
Gly

<210> SEQ ID NO 17
<211> LENGTH: 9
<212> TYPE: PRT
<213> ORGANISM: Artificial Sequence
<220> FEATURE:
<223> OTHER INFORMATION: clone MI329_Variable heavy chain CDR3

<400> SEQUENCE: 17

Trp Gly Glu Asn Trp Tyr Phe Asp Val
1               5

<210> SEQ ID NO 18
<211> LENGTH: 16
<212> TYPE: PRT
<213> ORGANISM: Artificial Sequence
<220> FEATURE:
<223> OTHER INFORMATION: clone MI329_Variable light chain CDR1

<400> SEQUENCE: 18

Arg Ser Ser Gln Ser Leu Val His Ser Asn Gly Asn Thr Tyr Leu His
1               5                   10                  15

<210> SEQ ID NO 19
<211> LENGTH: 7
<212> TYPE: PRT
<213> ORGANISM: Artificial Sequence
<220> FEATURE:
```

<223> OTHER INFORMATION: clone MI329_Variable light chain CDR2

<400> SEQUENCE: 19

Lys Val Ser Asn Arg Phe Ser
1               5

<210> SEQ ID NO 20
<211> LENGTH: 9
<212> TYPE: PRT
<213> ORGANISM: Artificial Sequence
<220> FEATURE:
<223> OTHER INFORMATION: clone MI329_Variable light chain CDR3

<400> SEQUENCE: 20

Ser Gln Ser Thr His Phe Pro Arg Thr
1               5

<210> SEQ ID NO 21
<211> LENGTH: 5
<212> TYPE: PRT
<213> ORGANISM: Artificial Sequence
<220> FEATURE:
<223> OTHER INFORMATION: clone MI403_Variable heavy chain CDR1

<400> SEQUENCE: 21

Ser Tyr Asp Met Ser
1               5

<210> SEQ ID NO 22
<211> LENGTH: 17
<212> TYPE: PRT
<213> ORGANISM: Artificial Sequence
<220> FEATURE:
<223> OTHER INFORMATION: clone MI403_Variable heavy chain CDR2

<400> SEQUENCE: 22

Tyr Ile Ser Ser Gly Gly Gly Ser Thr Tyr Tyr Pro Asp Thr Val Lys
1               5                   10                  15

Gly

<210> SEQ ID NO 23
<211> LENGTH: 13
<212> TYPE: PRT
<213> ORGANISM: Artificial Sequence
<220> FEATURE:
<223> OTHER INFORMATION: clone MI403_Variable heavy chain CDR3

<400> SEQUENCE: 23

Gln Gly Thr Ala Val Lys Asn Tyr Trp Tyr Phe Asp Val
1               5                   10

<210> SEQ ID NO 24
<211> LENGTH: 15
<212> TYPE: PRT
<213> ORGANISM: Artificial Sequence
<220> FEATURE:
<223> OTHER INFORMATION: clone MI403_Variable light chain CDR1

<400> SEQUENCE: 24

Arg Ala Ser Gln Ser Val Ser Thr Ser Ser Ser Ser Tyr Val His
1               5                   10                  15

<210> SEQ ID NO 25
<211> LENGTH: 7
<212> TYPE: PRT
<213> ORGANISM: Artificial Sequence

```
<220> FEATURE:
<223> OTHER INFORMATION: clone MI403_Variable light chain CDR2

<400> SEQUENCE: 25

Tyr Ala Ser Asn Leu Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: clone MI403_Variable light chain CDR3

<400> SEQUENCE: 26

Gln His Ser Trp Glu Ile Pro Phe Thr
1               5

<210> SEQ ID NO 27
<211> LENGTH: 5
<212> TYPE: PRT
<213> ORGANISM: Artificial Sequence
<220> FEATURE:
<223> OTHER INFORMATION: clone MI407_Variable heavy chain CDR1

<400> SEQUENCE: 27

Asn Tyr Asp Met Ser
1               5

<210> SEQ ID NO 28
<211> LENGTH: 17
<212> TYPE: PRT
<213> ORGANISM: Artificial Sequence
<220> FEATURE:
<223> OTHER INFORMATION: clone MI407_Variable heavy chain CDR2

<400> SEQUENCE: 28

Tyr Ile Ser Ser Gly Gly Gly Asn Thr Tyr Tyr Pro Asp Thr Val Lys
1               5                   10                  15
Gly

<210> SEQ ID NO 29
<211> LENGTH: 13
<212> TYPE: PRT
<213> ORGANISM: Artificial Sequence
<220> FEATURE:
<223> OTHER INFORMATION: clone MI407_Variable heavy chain CDR3

<400> SEQUENCE: 29

Gln Gly Thr Ser Val Glu Ser Tyr Trp Tyr Phe Asp Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: clone MI407_Variable light chain CDR1

<400> SEQUENCE: 30

Ser Val Ser Thr Ser Ser Ser Ser Tyr Ile His
1               5                   10

<210> SEQ ID NO 31
<211> LENGTH: 87
<212> TYPE: DNA
```

```
<213> ORGANISM: Artificial Sequence
<220> FEATURE:
<223> OTHER INFORMATION: MI323VH-F

<400> SEQUENCE: 31
gcggccgcca tgtacttggg actgaactat gtattcatag tttttctctt aaatggtgtc      60
cagagtgagg tccagctgca gcagtct                                          87

<210> SEQ ID NO 32
<211> LENGTH: 87
<212> TYPE: DNA
<213> ORGANISM: Artificial Sequence
<220> FEATURE:
<223> OTHER INFORMATION: MI329VH-F

<400> SEQUENCE: 32
gcggccgcca tgtacttggg actgaactat gtattcatag tttttctctt aaatggtgtc      60
cagagtgagg tgatgctggt ggagtct                                          87

<210> SEQ ID NO 33
<211> LENGTH: 87
<212> TYPE: DNA
<213> ORGANISM: Artificial Sequence
<220> FEATURE:
<223> OTHER INFORMATION: MI403VH-F

<400> SEQUENCE: 33
gcggccgcca tgtacttggg actgaactat gtattcatag tttttctctt aaatggtgtc      60
cagagtgagg tgcaggtggt ggagtct                                          87

<210> SEQ ID NO 34
<211> LENGTH: 87
<212> TYPE: DNA
<213> ORGANISM: Artificial Sequence
<220> FEATURE:
<223> OTHER INFORMATION: MI407VH-F

<400> SEQUENCE: 34
gcggccgcca tgtacttggg actgaactat gtattcatag tttttctctt aaatggtgtc      60
cagagtgagg tgaagttggt ggagtct                                          87

<210> SEQ ID NO 35
<211> LENGTH: 20
<212> TYPE: DNA
<213> ORGANISM: Artificial Sequence
<220> FEATURE:
<223> OTHER INFORMATION: VHApaI-R

<400> SEQUENCE: 35
accgatgggc ccttggtgga                                                  20

<210> SEQ ID NO 36
<211> LENGTH: 96
<212> TYPE: DNA
<213> ORGANISM: Artificial Sequence
<220> FEATURE:
<223> OTHER INFORMATION: MI323VL-F

<400> SEQUENCE: 36
gcggccgcca tggatagcca ggctcaggtg ctgatgctgc tgctgctgtg ggtgtcaggg      60
acttgcgggg acattgtgat gacccagtct cacaaa                                96
```

```
<210> SEQ ID NO 37
<211> LENGTH: 45
<212> TYPE: DNA
<213> ORGANISM: Artificial Sequence
<220> FEATURE:
<223> OTHER INFORMATION: MI323VLCL-R

<400> SEQUENCE: 37
acactaggag cggccacggt tcgtttgatt tccagtttgg tccct            45

<210> SEQ ID NO 38
<211> LENGTH: 96
<212> TYPE: DNA
<213> ORGANISM: Artificial Sequence
<220> FEATURE:
<223> OTHER INFORMATION: MI329VL-F

<400> SEQUENCE: 38
gcggccgcca tggatagcca ggctcaggtg ctgatgctgc tgctgctgtg ggtgtcaggg    60
acttgcgggg acgttgtgat gacccagact ccactc                              96

<210> SEQ ID NO 39
<211> LENGTH: 42
<212> TYPE: DNA
<213> ORGANISM: Artificial Sequence
<220> FEATURE:
<223> OTHER INFORMATION: MI329VLCL-R

<400> SEQUENCE: 39
acactaggag cggccacggt tcgtttcagc tccagcttgg tc                42

<210> SEQ ID NO 40
<211> LENGTH: 96
<212> TYPE: DNA
<213> ORGANISM: Artificial Sequence
<220> FEATURE:
<223> OTHER INFORMATION: MI403VL-F

<400> SEQUENCE: 40
gcggccgcca tggatagcca ggctcaggtg ctgatgctgc tgctgctgtg ggtgtcaggg    60
acttgcgggg atattgtgat gacccagtct cctgct                              96

<210> SEQ ID NO 41
<211> LENGTH: 47
<212> TYPE: DNA
<213> ORGANISM: Artificial Sequence
<220> FEATURE:
<223> OTHER INFORMATION: MI403VLCL-R

<400> SEQUENCE: 41
acactaggag cggccacggt tcgtttttatt tccaactttg tccccga        47

<210> SEQ ID NO 42
<211> LENGTH: 96
<212> TYPE: DNA
<213> ORGANISM: Artificial Sequence
<220> FEATURE:
<223> OTHER INFORMATION: M407VL-F

<400> SEQUENCE: 42
gcggccgcca tggatagcca ggctcaggtg ctgatgctgc tgctgctgtg ggtgtcaggg    60
acttgcgggg atattgtgtt gacacagtct cctgct                              96

<210> SEQ ID NO 43
```

```
<211> LENGTH: 46
<212> TYPE: DNA
<213> ORGANISM: Artificial Sequence
<220> FEATURE:
<223> OTHER INFORMATION: M407VLCL-R

<400> SEQUENCE: 43
acactaggag cggccacggt tcgttttatt tccaactctg tccccg                    46

<210> SEQ ID NO 44
<211> LENGTH: 20
<212> TYPE: DNA
<213> ORGANISM: Artificial Sequence
<220> FEATURE:
<223> OTHER INFORMATION: Ck-F

<400> SEQUENCE: 44
accgtggccg ctcctagtgt                                                 20

<210> SEQ ID NO 45
<211> LENGTH: 29
<212> TYPE: DNA
<213> ORGANISM: Artificial Sequence
<220> FEATURE:
<223> OTHER INFORMATION: CkSHB-R
<220> FEATURE:
<221> NAME/KEY: misc_feature
<222> LOCATION: (1)..(4)
<223> OTHER INFORMATION: n is a, c, g, or t

<400> SEQUENCE: 45
nnnnggatcc aagcttacta gcactcccc                                       29

<210> SEQ ID NO 46
<211> LENGTH: 116
<212> TYPE: PRT
<213> ORGANISM: Artificial Sequence
<220> FEATURE:
<223> OTHER INFORMATION: clone MS501_Variable heavy chain

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Tyr Pro Asp Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Ile Tyr Thr Phe Asp Tyr Trp Gly Gln Gly Thr Leu Val
            100                 105                 110

Thr Val Ser Ser
        115

<210> SEQ ID NO 47
<211> LENGTH: 111
<212> TYPE: PRT
<213> ORGANISM: Artificial Sequence
<220> FEATURE:
<223> OTHER INFORMATION: clone MS501_Variable light chain
```

<400> SEQUENCE: 47

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Tyr Tyr Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ser Ser Leu
                85                  90                  95

Ser Gly Tyr Val Phe Gly Gly Gly Thr Lys Leu Thr Val Leu Gly
            100                 105                 110

<210> SEQ ID NO 48
<211> LENGTH: 116
<212> TYPE: PRT
<213> ORGANISM: Artificial Sequence
<220> FEATURE:
<223> OTHER INFORMATION: clone MS502_Variable heavy chain

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Pro Pro Asp Ser Gly Ser Lys Tyr Tyr Ala Asp Ser Val
50                  55                  60

Arg Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Met Leu Ser Phe Asp Tyr Trp Gly Gln Gly Thr Leu Val
            100                 105                 110

Thr Val Ser Ser
        115

<210> SEQ ID NO 49
<211> LENGTH: 111
<212> TYPE: PRT
<213> ORGANISM: Artificial Sequence
<220> FEATURE:
<223> OTHER INFORMATION: clone MS502_Variable light chain

<400> SEQUENCE: 49

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Tyr Tyr Asn Ser Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ser Ser Leu
                85                  90                  95

Asn Gly Tyr Val Phe Gly Gly Gly Thr Lys Val Thr Val Leu Gly
            100                 105                 110

<210> SEQ ID NO 50
<211> LENGTH: 111
<212> TYPE: PRT
<213> ORGANISM: Artificial Sequence
<220> FEATURE:
<223> OTHER INFORMATION: clone MS502-1_Variable light chain

<400> SEQUENCE: 50

Gln Ser Val Leu Thr Gln Pro Pro Ser Ala Ser Gly Thr Pro Gly Gln
1               5                   10                  15

Arg Val Thr Ile Ser Cys Ile Cys Ser Ser Asn Ile Gly Ser Asn
            20                  25                  30

Ala Val Ser Trp Tyr Gln Gln Leu Pro Gly Thr Ala Pro Lys Leu Leu
            35                  40                  45

Ile Tyr Tyr Asn Ser Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ser Ser Leu
                85                  90                  95

Asn Gly Tyr Val Phe Gly Gly Gly Thr Lys Leu Thr Val Leu Gly
            100                 105                 110

<210> SEQ ID NO 51
<211> LENGTH: 116
<212> TYPE: PRT
<213> ORGANISM: Artificial Sequence
<220> FEATURE:
<223> OTHER INFORMATION: clone MS503_Variable heavy chain

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ser Ser Ile Tyr Pro Gly Asp Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ala Phe Thr Phe Asp Tyr Trp Gly Gln Gly Thr Leu Val
            100                 105                 110

Thr Val Ser Ser
        115

<210> SEQ ID NO 52
<211> LENGTH: 111
<212> TYPE: PRT

<213> ORGANISM: Artificial Sequence
<220> FEATURE:
<223> OTHER INFORMATION: clone MS503_Variable light chain

<400> SEQUENCE: 52

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Tyr Tyr Asn Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ser Ser Leu
                85                  90                  95

Ser Gly Tyr Val Phe Gly Gly Gly Thr Lys Leu Thr Val Leu Gly
            100                 105                 110

<210> SEQ ID NO 53
<211> LENGTH: 116
<212> TYPE: PRT
<213> ORGANISM: Artificial Sequence
<220> FEATURE:
<223> OTHER INFORMATION: clone MS504_Variable heavy chain

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Tyr Pro Asn Gly Ser Ser Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Lys Asn Leu Leu Thr Phe Asp Tyr Trp Gly Gln Gly Thr Leu Val
            100                 105                 110

Thr Val Ser Ser
        115

<210> SEQ ID NO 54
<211> LENGTH: 111
<212> TYPE: PRT
<213> ORGANISM: Artificial Sequence
<220> FEATURE:
<223> OTHER INFORMATION: clone MS504_Variable light chain

<400> SEQUENCE: 54

Gln Ser Val Leu Thr Gln Pro Pro Ser Ala Ser Gly Pro Pro Gly Gln
1               5                   10                  15

Arg Val Thr Ile Ser Cys Thr Gly Ser Ser Ser Asn Ile Gly Asn Asn
            20                  25                  30

Ser Val Ser Trp Tyr Gln Gln Leu Pro Gly Thr Ala Pro Lys Leu Leu
        35                  40                  45

```
Ile Tyr Tyr Asp Ser His Arg Pro Ser Gly Val Pro Asp Arg Phe Ser
         50                  55                  60

Gly Ser Lys Ser Gly Thr Ser Ala Ser Leu Ala Ile Gly Gly Leu Arg
 65                  70                  75                  80

Ser Glu Asp Glu Ala Asp Tyr Tyr Cys Gly Ala Trp Asp Ser Ser Leu
                 85                  90                  95

Asn Ala Tyr Val Phe Gly Gly Gly Thr Lys Leu Thr Val Leu Gly
                100                 105                 110

<210> SEQ ID NO 55
<211> LENGTH: 116
<212> TYPE: PRT
<213> ORGANISM: Artificial Sequence
<220> FEATURE:
<223> OTHER INFORMATION: clone MS505_Variable heavy chain

<400> SEQUENCE: 55

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Ala Met Ser Trp Val Arg Gln Ala Pro Gly Lys Gly Leu Glu Trp Val
         35                  40                  45

Ser Ala Ile Tyr Pro Asp Gly Ser Asn Lys Tyr Tyr Ala Asp Ser Val
     50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Ala Tyr Thr Phe Asp Tyr Trp Gly Gln Gly Thr Leu Val
                100                 105                 110

Thr Val Ser Ser
        115

<210> SEQ ID NO 56
<211> LENGTH: 111
<212> TYPE: PRT
<213> ORGANISM: Artificial Sequence
<220> FEATURE:
<223> OTHER INFORMATION: clone MS505_Variable light chain

<400> SEQUENCE: 56

Gln Ser Val Leu Thr Gln Pro Pro Ser Ala Ser Gly Thr Pro Gly Arg
 1               5                  10                  15

Arg Val Thr Ile Ser Cys Ser Gly Ser Ser Ser Asn Ile Gly Ser Asn
             20                  25                  30

Ala Val Ser Trp Tyr Gln Gln Leu Pro Gly Thr Ala Pro Lys Leu Leu
         35                  40                  45

Ile Tyr Tyr Asn Ser Gln Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ser Ser Leu
                 85                  90                  95

Asn Gly Tyr Val Phe Gly Gly Gly Thr Lys Leu Thr Val Leu Gly
                100                 105                 110
```

<210> SEQ ID NO 57
<211> LENGTH: 116
<212> TYPE: PRT
<213> ORGANISM: Artificial Sequence
<220> FEATURE:
<223> OTHER INFORMATION: clone MS506_Variable heavy chain

<400> SEQUENCE: 57

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Tyr Pro Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Tyr Thr Phe Asp Tyr Trp Gly Gln Gly Thr Leu Val
            100                 105                 110

Thr Val Ser Ser
        115
```

<210> SEQ ID NO 58
<211> LENGTH: 111
<212> TYPE: PRT
<213> ORGANISM: Artificial Sequence
<220> FEATURE:
<223> OTHER INFORMATION: clone MS506_Variable light chain

<400> SEQUENCE: 58

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ala Val Thr Trp Tyr Gln Gln Leu Pro Gly Thr Ala Pro Lys Leu Leu
        35                  40                  45

Ile Tyr Tyr Asp Ser His Arg Pro Ser Gly Val Pro Asp Arg Phe Ser
    50                  55                  60

Gly Ser Lys Ser Gly Thr Ser Ala Ser Leu Ala Ile Ser Gly Pro Arg
65                  70                  75                  80

Ser Glu Asp Glu Ala Asp Tyr Tyr Cys Gly Ala Trp Asp Ser Ser Leu
                85                  90                  95

Ser Ala Tyr Val Phe Gly Gly Gly Thr Lys Leu Thr Val Leu Gly
            100                 105                 110
```

<210> SEQ ID NO 59
<211> LENGTH: 5
<212> TYPE: PRT
<213> ORGANISM: Artificial Sequence
<220> FEATURE:
<223> OTHER INFORMATION: clone MS501_Variable heavy chain CDR1

<400> SEQUENCE: 59

```
Asn Tyr Ala Met Ser
1               5
```

<210> SEQ ID NO 60

```
<211> LENGTH: 17
<212> TYPE: PRT
<213> ORGANISM: Artificial Sequence
<220> FEATURE:
<223> OTHER INFORMATION: clone MS501_Variable heavy chain CDR2

<400> SEQUENCE: 60

Gly Ile Tyr Pro Asp Ser Gly Ser Thr Tyr Tyr Ala Asp Ser Val Lys
1               5                   10                  15

Gly

<210> SEQ ID NO 61
<211> LENGTH: 7
<212> TYPE: PRT
<213> ORGANISM: Artificial Sequence
<220> FEATURE:
<223> OTHER INFORMATION: clone MS501 Variable heavy chain CDR3

<400> SEQUENCE: 61

Asn Ile Tyr Thr Phe Asp Tyr
1               5

<210> SEQ ID NO 62
<211> LENGTH: 13
<212> TYPE: PRT
<213> ORGANISM: Artificial Sequence
<220> FEATURE:
<223> OTHER INFORMATION: clone MS501_Variable light chain CDR1

<400> SEQUENCE: 62

Ser Gly Ser Ser Ser Asn Ile Gly Ser Asn Ala Val Ser
1               5                   10

<210> SEQ ID NO 63
<211> LENGTH: 7
<212> TYPE: PRT
<213> ORGANISM: Artificial Sequence
<220> FEATURE:
<223> OTHER INFORMATION: clone MS501_Variable light chain CDR2

<400> SEQUENCE: 63

Tyr Asn Asn Gln Arg Pro Ser
1               5

<210> SEQ ID NO 64
<211> LENGTH: 11
<212> TYPE: PRT
<213> ORGANISM: Artificial Sequence
<220> FEATURE:
<223> OTHER INFORMATION: clone MS501_Variable light chain CDR3

<400> SEQUENCE: 64

Gly Ser Trp Asp Ser Ser Leu Ser Gly Tyr Val
1               5                   10

<210> SEQ ID NO 65
<211> LENGTH: 17
<212> TYPE: PRT
<213> ORGANISM: Artificial Sequence
<220> FEATURE:
<223> OTHER INFORMATION: clone MS502_Variable heavy chain CDR2

<400> SEQUENCE: 65

Gly Ile Pro Pro Asp Ser Gly Ser Lys Tyr Tyr Ala Asp Ser Val Arg
1               5                   10                  15

Gly
```

<210> SEQ ID NO 66
<211> LENGTH: 7
<212> TYPE: PRT
<213> ORGANISM: Artificial Sequence
<220> FEATURE:
<223> OTHER INFORMATION: clone MS502 Variable heavy chain CDR3

<400> SEQUENCE: 66

Asn Met Leu Ser Phe Asp Tyr
1               5

<210> SEQ ID NO 67
<211> LENGTH: 13
<212> TYPE: PRT
<213> ORGANISM: Artificial Sequence
<220> FEATURE:
<223> OTHER INFORMATION: clone MS502_Variable light chain CDR1

<400> SEQUENCE: 67

Thr Gly Ser Ser Ser Asn Ile Gly Ser Asn Ala Val Ser
1               5                   10

<210> SEQ ID NO 68
<211> LENGTH: 7
<212> TYPE: PRT
<213> ORGANISM: Artificial Sequence
<220> FEATURE:
<223> OTHER INFORMATION: clone MS502_Variable light chain CDR2

<400> SEQUENCE: 68

Tyr Asn Ser Lys Arg Pro Ser
1               5

<210> SEQ ID NO 69
<211> LENGTH: 11
<212> TYPE: PRT
<213> ORGANISM: Artificial Sequence
<220> FEATURE:
<223> OTHER INFORMATION: clone MS502_Variable light chain CDR3

<400> SEQUENCE: 69

Gly Ser Trp Asp Ser Ser Leu Asn Gly Tyr Val
1               5                   10

<210> SEQ ID NO 70
<211> LENGTH: 13
<212> TYPE: PRT
<213> ORGANISM: Artificial Sequence
<220> FEATURE:
<223> OTHER INFORMATION: clone MS502-1_Variable light chain CDR1

<400> SEQUENCE: 70

Ile Cys Ser Ser Ser Asn Ile Gly Ser Asn Ala Val Ser
1               5                   10

<210> SEQ ID NO 71
<211> LENGTH: 17
<212> TYPE: PRT
<213> ORGANISM: Artificial Sequence
<220> FEATURE:
<223> OTHER INFORMATION: clone MS503_Variable heavy chain CDR2

<400> SEQUENCE: 71

Ser Ile Tyr Pro Gly Asp Gly Ser Thr Tyr Tyr Ala Asp Ser Val Lys
1               5                   10                  15

Gly

<210> SEQ ID NO 72
<211> LENGTH: 7
<212> TYPE: PRT
<213> ORGANISM: Artificial Sequence
<220> FEATURE:
<223> OTHER INFORMATION: clone MS503_Variable heavy chain CDR3

<400> SEQUENCE: 72

Asn Ala Phe Thr Phe Asp Tyr
1               5

<210> SEQ ID NO 73
<211> LENGTH: 7
<212> TYPE: PRT
<213> ORGANISM: Artificial Sequence
<220> FEATURE:
<223> OTHER INFORMATION: clone MS503_Variable light chain CDR2

<400> SEQUENCE: 73

Tyr Asn Ser His Arg Pro Ser
1               5

<210> SEQ ID NO 74
<211> LENGTH: 11
<212> TYPE: PRT
<213> ORGANISM: Artificial Sequence
<220> FEATURE:
<223> OTHER INFORMATION: clone MS503_Variable light chain CDR3

<400> SEQUENCE: 74

Gly Thr Trp Asp Ser Ser Leu Ser Gly Tyr Val
1               5                   10

<210> SEQ ID NO 75
<211> LENGTH: 17
<212> TYPE: PRT
<213> ORGANISM: Artificial Sequence
<220> FEATURE:
<223> OTHER INFORMATION: clone MS504_Variable heavy chain CDR2

<400> SEQUENCE: 75

Ser Ile Tyr Pro Asn Gly Ser Ser Lys Tyr Tyr Ala Asp Ser Val Lys
1               5                   10                  15
Gly

<210> SEQ ID NO 76
<211> LENGTH: 7
<212> TYPE: PRT
<213> ORGANISM: Artificial Sequence
<220> FEATURE:
<223> OTHER INFORMATION: clone MS504_Variable heavy chain CDR3

<400> SEQUENCE: 76

Asn Leu Leu Thr Phe Asp Tyr
1               5

<210> SEQ ID NO 77
<211> LENGTH: 13
<212> TYPE: PRT
<213> ORGANISM: Artificial Sequence
<220> FEATURE:
<223> OTHER INFORMATION: clone MS504_Variable light chain CDR1

<400> SEQUENCE: 77

Thr Gly Ser Ser Ser Asn Ile Gly Asn Asn Ser Val Ser
1               5                   10

<210> SEQ ID NO 78
<211> LENGTH: 7
<212> TYPE: PRT
<213> ORGANISM: Artificial Sequence
<220> FEATURE:
<223> OTHER INFORMATION: clone MS504_Variable light chain CDR2

<400> SEQUENCE: 78

Tyr Asp Ser His Arg Pro Ser
1               5

<210> SEQ ID NO 79
<211> LENGTH: 11
<212> TYPE: PRT
<213> ORGANISM: Artificial Sequence
<220> FEATURE:
<223> OTHER INFORMATION: clone MS504_Variable light chain CDR3

<400> SEQUENCE: 79

Gly Ala Trp Asp Asp Ser Leu Asn Ala Tyr Val
1               5                   10

<210> SEQ ID NO 80
<211> LENGTH: 17
<212> TYPE: PRT
<213> ORGANISM: Artificial Sequence
<220> FEATURE:
<223> OTHER INFORMATION: clone MS505_Variable heavy chain CDR2

<400> SEQUENCE: 80

Ala Ile Tyr Pro Asp Gly Ser Asn Lys Tyr Tyr Ala Asp Ser Val Lys
1               5                   10                  15

Gly

<210> SEQ ID NO 81
<211> LENGTH: 7
<212> TYPE: PRT
<213> ORGANISM: Artificial Sequence
<220> FEATURE:
<223> OTHER INFORMATION: clone MS505_Variable heavy chain CDR3

<400> SEQUENCE: 81

Asn Ala Tyr Thr Phe Asp Tyr
1               5

<210> SEQ ID NO 82
<211> LENGTH: 7
<212> TYPE: PRT
<213> ORGANISM: Artificial Sequence
<220> FEATURE:
<223> OTHER INFORMATION: clone MS505_Variable light chain CDR2

<400> SEQUENCE: 82

Tyr Asn Ser Gln Arg Pro Ser
1               5

<210> SEQ ID NO 83
<211> LENGTH: 11
<212> TYPE: PRT
<213> ORGANISM: Artificial Sequence
<220> FEATURE:
<223> OTHER INFORMATION: clone MS505_Variable light chain CDR3

<400> SEQUENCE: 83

```
Gly Ser Trp Asp Ser Ser Leu Asn Gly Tyr Val
1               5                   10
```

<210> SEQ ID NO 84
<211> LENGTH: 17
<212> TYPE: PRT
<213> ORGANISM: Artificial Sequence
<220> FEATURE:
<223> OTHER INFORMATION: clone MS506_Variable heavy chain CDR2

<400> SEQUENCE: 84

```
Ser Ile Tyr Pro Gly Ser Gly Ser Thr Tyr Tyr Ala Asp Ser Val Lys
1               5                   10                  15
Gly
```

<210> SEQ ID NO 85
<211> LENGTH: 7
<212> TYPE: PRT
<213> ORGANISM: Artificial Sequence
<220> FEATURE:
<223> OTHER INFORMATION: clone MS506_Variable heavy chain CDR3

<400> SEQUENCE: 85

```
Asn Leu Tyr Thr Phe Asp Tyr
1               5
```

<210> SEQ ID NO 86
<211> LENGTH: 13
<212> TYPE: PRT
<213> ORGANISM: Artificial Sequence
<220> FEATURE:
<223> OTHER INFORMATION: clone MS506_Variable light chain CDR1

<400> SEQUENCE: 86

```
Thr Gly Ser Ser Ser Asn Ile Gly Ser Asn Ala Val Thr
1               5                   10
```

<210> SEQ ID NO 87
<211> LENGTH: 11
<212> TYPE: PRT
<213> ORGANISM: Artificial Sequence
<220> FEATURE:
<223> OTHER INFORMATION: clone MS506_Variable light chain CDR3

<400> SEQUENCE: 87

```
Gly Ala Trp Asp Ser Ser Leu Ser Ala Tyr Val
1               5                   10
```

<210> SEQ ID NO 88
<211> LENGTH: 94
<212> TYPE: DNA
<213> ORGANISM: Artificial Sequence
<220> FEATURE:
<223> OTHER INFORMATION: NotI-Leader- VL-F
<220> FEATURE:
<221> NAME/KEY: misc_feature
<222> LOCATION: (1)..(4)
<223> OTHER INFORMATION: n is a, c, g, or t

<400> SEQUENCE: 88

```
nnnngcggcc gccatggata gccaggctca ggtgctgatg ctgctgctgc tgtgggtgtc    60
agggacttgc gggcagtctg tgctgactca gcca                                94
```

<210> SEQ ID NO 89
<211> LENGTH: 39

```
<212> TYPE: DNA
<213> ORGANISM: Artificial Sequence
<220> FEATURE:
<223> OTHER INFORMATION: VL-R

<400> SEQUENCE: 89
ggggttggcc ttgggctggc ctaggaccgt cagcttggt                        39

<210> SEQ ID NO 90
<211> LENGTH: 18
<212> TYPE: DNA
<213> ORGANISM: Artificial Sequence
<220> FEATURE:
<223> OTHER INFORMATION: VL-CL-F

<400> SEQUENCE: 90
cagcccaagg ccaacccc                                               18

<210> SEQ ID NO 91
<211> LENGTH: 42
<212> TYPE: DNA
<213> ORGANISM: Artificial Sequence
<220> FEATURE:
<223> OTHER INFORMATION: HindIII-VL-R
<220> FEATURE:
<221> NAME/KEY: misc_feature
<222> LOCATION: (1)..(4)
<223> OTHER INFORMATION: n is a, c, g, or t

<400> SEQUENCE: 91
nnnnggatcc aagcttacta acattctgta ggggccactg tc                    42

<210> SEQ ID NO 92
<211> LENGTH: 97
<212> TYPE: DNA
<213> ORGANISM: Artificial Sequence
<220> FEATURE:
<223> OTHER INFORMATION: HD-Heavy-F

<400> SEQUENCE: 92
ggtgtccagg cggccgccat gtacttggga ctgaactatg tattcatagt ttttctctta 60
aatggtgtcc agagtgaggt gcagctgttg gagtctg                          97

<210> SEQ ID NO 93
<211> LENGTH: 52
<212> TYPE: DNA
<213> ORGANISM: Artificial Sequence
<220> FEATURE:
<223> OTHER INFORMATION: HD-Heavy-R

<400> SEQUENCE: 93
gggggaagac cgatgggccc ttggtggagg ctgagctcac ggtgaccagt gt         52

<210> SEQ ID NO 94
<211> LENGTH: 79
<212> TYPE: DNA
<213> ORGANISM: Artificial Sequence
<220> FEATURE:
<223> OTHER INFORMATION: MS502 VL FR1 Fo NruI

<400> SEQUENCE: 94
gctcgcgatt gcagtggcac tggctggttt cgctaccgtg gcccaggcgg cccagtctgt 60
gctgactcag ccaccctca                                              79

<210> SEQ ID NO 95
```

```
<211> LENGTH: 27
<212> TYPE: DNA
<213> ORGANISM: Artificial Sequence
<220> FEATURE:
<223> OTHER INFORMATION: MS502 VL FR1 Fo

<400> SEQUENCE: 95
cagtctgtgc tgactcagcc accctca                                      27

<210> SEQ ID NO 96
<211> LENGTH: 60
<212> TYPE: DNA
<213> ORGANISM: Artificial Sequence
<220> FEATURE:
<223> OTHER INFORMATION: MS502 VL FR1 Re

<400> SEQUENCE: 96
gagctgctgg taccaggaga cagcattrtg gccaatatta gatgaagagc cagtacaaga   60

<210> SEQ ID NO 97
<211> LENGTH: 30
<212> TYPE: DNA
<213> ORGANISM: Artificial Sequence
<220> FEATURE:
<223> OTHER INFORMATION: MS502 VL FR2 Fo

<400> SEQUENCE: 97
gccaatatta gatgaagagc cagtacaaga                                   30

<210> SEQ ID NO 98
<211> LENGTH: 93
<212> TYPE: DNA
<213> ORGANISM: Artificial Sequence
<220> FEATURE:
<223> OTHER INFORMATION: MS502 VL FR2 Re

<400> SEQUENCE: 98
acctaggacg gtcaccttgg tgcctccgcc gaagacataa ccrtgcaggc trtgatcctg   60
agaaccacag taataatcag cctcatcctc gga                               93

<210> SEQ ID NO 99
<211> LENGTH: 48
<212> TYPE: DNA
<213> ORGANISM: Artificial Sequence
<220> FEATURE:
<223> OTHER INFORMATION: MS502 CL Fo

<400> SEQUENCE: 99
ggcaccaagg tgaccgtcct aggtcagccc aaggccaacc ccactgtc                48

<210> SEQ ID NO 100
<211> LENGTH: 35
<212> TYPE: DNA
<213> ORGANISM: Artificial Sequence
<220> FEATURE:
<223> OTHER INFORMATION: MS502 CL Re

<400> SEQUENCE: 100
gctctagaac attctgtagg ggccactgtc ttctc                             35

<210> SEQ ID NO 101
<211> LENGTH: 34
<212> TYPE: DNA
<213> ORGANISM: Artificial Sequence
<220> FEATURE:
<223> OTHER INFORMATION: MS502 VH FR1 Fo NcoI
```

<400> SEQUENCE: 101
gcccatggcc gaggtgcagc tgttggagtc tggg                                    34

<210> SEQ ID NO 102
<211> LENGTH: 57
<212> TYPE: DNA
<213> ORGANISM: Artificial Sequence
<220> FEATURE:
<223> OTHER INFORMATION: MS502 VH FR1 Re
<220> FEATURE:
<221> NAME/KEY: misc_feature
<222> LOCATION: (22)..(22)
<223> OTHER INFORMATION: n is a, c, g, or t

<400> SEQUENCE: 102
agcctggcgg acccagctca tntgrtgrtg gctaaaggtg aatccagagg ccgcaca          57

<210> SEQ ID NO 103
<211> LENGTH: 21
<212> TYPE: DNA
<213> ORGANISM: Artificial Sequence
<220> FEATURE:
<223> OTHER INFORMATION: MS502 VH FR2 Fo

<400> SEQUENCE: 103
atgagctggg tccgccaggc t                                                  21

<210> SEQ ID NO 104
<211> LENGTH: 72
<212> TYPE: DNA
<213> ORGANISM: Artificial Sequence
<220> FEATURE:
<223> OTHER INFORMATION: MS502 VH FR2 Re
<220> FEATURE:
<221> NAME/KEY: misc_feature
<222> LOCATION: (40)..(40)
<223> OTHER INFORMATION: n is a, c, g, or t

<400> SEQUENCE: 104
ggtgaaccga cctcttacag aatcagcgta atatttrtgn tgactrtgag gagggatccc       60
tgagacccac tc                                                            72

<210> SEQ ID NO 105
<211> LENGTH: 36
<212> TYPE: DNA
<213> ORGANISM: Artificial Sequence
<220> FEATURE:
<223> OTHER INFORMATION: MS502 VH FR3 Fo

<400> SEQUENCE: 105
aaatattacg ctgattctgt aagaggtcgg ttcacc                                  36

<210> SEQ ID NO 106
<211> LENGTH: 78
<212> TYPE: DNA
<213> ORGANISM: Artificial Sequence
<220> FEATURE:
<223> OTHER INFORMATION: MS502 VH FR3 Re
<220> FEATURE:
<221> NAME/KEY: misc_feature
<222> LOCATION: (46)..(46)
<223> OTHER INFORMATION: n is a, c, g, or t

<400> SEQUENCE: 106
tgagctcacc gtgaccagtg taccctggcc ccagtagtcr tgrtgntgca tattttttcgc      60

```
acagtaatac acggccgt                                               78
```

<210> SEQ ID NO 107
<211> LENGTH: 27
<212> TYPE: DNA
<213> ORGANISM: Artificial Sequence
<220> FEATURE:
<223> OTHER INFORMATION: MS502 VH Re

<400> SEQUENCE: 107

```
tgagctcacc gtgaccagtg taccctg                                     27
```

<210> SEQ ID NO 108
<211> LENGTH: 46
<212> TYPE: DNA
<213> ORGANISM: Artificial Sequence
<220> FEATURE:
<223> OTHER INFORMATION: MS502 VH Re ApaI

<400> SEQUENCE: 108

```
gcgggccctt ggtggaggct gagctcaccg tgaccagtgt accctg                46
```

<210> SEQ ID NO 109
<211> LENGTH: 111
<212> TYPE: PRT
<213> ORGANISM: Artificial Sequence
<220> FEATURE:
<223> OTHER INFORMATION: clone C2G1_Variable light chain

<400> SEQUENCE: 109

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Pro Asn
            20                  25                  30

Ala Val Ser Trp Tyr Gln Gln Leu Pro Gly Thr Ala Pro Lys Leu Leu
        35                  40                  45

Ile Tyr Tyr Asn Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ser Ser Leu
                85                  90                  95

Ser Gly Tyr Val Phe Gly Gly Gly Thr Lys Val Thr Val Leu Gly
            100                 105                 110

<210> SEQ ID NO 110
<211> LENGTH: 111
<212> TYPE: PRT
<213> ORGANISM: Artificial Sequence
<220> FEATURE:
<223> OTHER INFORMATION: clone C2G4_Variable light chain

<400> SEQUENCE: 110

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Tyr Tyr Asn Ser Lys Arg Pro Ser Gly Val Pro Asp Arg Phe Ser
    50                  55                  60

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Pro Ser Leu
                 85                  90                  95

Asn Gly Tyr Val Phe Gly Gly Gly Thr Lys Val Thr Val Leu Gly
            100                 105                 110

<210> SEQ ID NO 111
<211> LENGTH: 111
<212> TYPE: PRT
<213> ORGANISM: Artificial Sequence
<220> FEATURE:
<223> OTHER INFORMATION: clone C3C8_Variable light chain

<400> SEQUENCE: 111

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Pro Asn
            20                  25                  30

Ala Val Ser Trp Tyr Gln Gln Leu Pro Gly Thr Ala Pro Lys Leu Leu
        35                  40                  45

Ile Tyr Tyr Asn Ser Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ser Asp Leu
                 85                  90                  95

Arg Gly Tyr Val Phe Gly Gly Gly Thr Lys Val Thr Val Leu Gly
            100                 105                 110

<210> SEQ ID NO 112
<211> LENGTH: 116
<212> TYPE: PRT
<213> ORGANISM: Artificial Sequence
<220> FEATURE:
<223> OTHER INFORMATION: clone 54_Variable heavy chain

<400> SEQUENCE: 112

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Tyr Pro Asp Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Ile Tyr Thr Phe Asp Tyr Trp Gly Gln Gly Thr Leu Val
            100                 105                 110

Thr Val Ser Ser
        115

<210> SEQ ID NO 113
<211> LENGTH: 116
<212> TYPE: PRT
<213> ORGANISM: Artificial Sequence
```

```
<220> FEATURE:
<223> OTHER INFORMATION: clone 56_Variable heavy chain

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Pro Pro Asp Ser Ala Ser Lys Tyr Tyr Ala Asp Ser Val
    50                  55                  60

Arg Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Met Leu Ser Phe Asp Tyr Trp Gly Gln Gly Thr Leu Val
            100                 105                 110

Thr Val Ser Ser
        115

<210> SEQ ID NO 114
<211> LENGTH: 116
<212> TYPE: PRT
<213> ORGANISM: Artificial Sequence
<220> FEATURE:
<223> OTHER INFORMATION: clone 2-30_Variable heavy chain

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Pro Pro Asp Ser Asn Ser Lys Tyr Tyr Ala Asp Ser Val
    50                  55                  60

Arg Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Met Arg Thr Phe Asp Tyr Trp Gly Gln Gly Thr Leu Val
            100                 105                 110

Thr Val Ser Ser
        115

<210> SEQ ID NO 115
<211> LENGTH: 116
<212> TYPE: PRT
<213> ORGANISM: Artificial Sequence
<220> FEATURE:
<223> OTHER INFORMATION: clone 2-73_Variable heavy chain

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Ala Met Ser Trp Val Arg Gln Ala Pro Gly Lys Gly Leu Glu Trp Val
            35                  40                  45

Ser Gly Ile Pro Pro Asn Ser Asp Ser Lys Tyr Tyr Ala Asp Ser Val
 50                  55                  60

Arg Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Met Leu Ser Phe Asp Tyr Trp Gly Gln Gly Thr Leu Val
             100                 105                 110

Thr Val Ser Ser
        115

<210> SEQ ID NO 116
<211> LENGTH: 116
<212> TYPE: PRT
<213> ORGANISM: Artificial Sequence
<220> FEATURE:
<223> OTHER INFORMATION: clone 2-78_Variable heavy chain

<400> SEQUENCE: 116

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Ala Met Ser Trp Val Arg Gln Ala Pro Gly Lys Gly Leu Glu Trp Val
            35                  40                  45

Ser Gly Ile Pro Pro Asp Ser Gly Ser Lys Tyr Tyr Ala Asp Ser Val
 50                  55                  60

Arg Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Met Phe Ser Phe Asp Tyr Trp Gly Gln Gly Thr Leu Val
             100                 105                 110

Thr Val Ser Ser
        115

<210> SEQ ID NO 117
<211> LENGTH: 13
<212> TYPE: PRT
<213> ORGANISM: Artificial Sequence
<220> FEATURE:
<223> OTHER INFORMATION: clone C2G1_Variable light chain CDR1

<400> SEQUENCE: 117

Thr Gly Ser Ser Ser Asn Ile Gly Pro Asn Ala Val Ser
 1               5                  10

<210> SEQ ID NO 118
<211> LENGTH: 11
<212> TYPE: PRT
<213> ORGANISM: Artificial Sequence
<220> FEATURE:
<223> OTHER INFORMATION: clone C2G1_Variable light chain CDR3

<400> SEQUENCE: 118

Gly Ser Trp Asp Ser Ser Leu Ser Gly Tyr Val
 1               5                  10
```

```
<210> SEQ ID NO 119
<211> LENGTH: 11
<212> TYPE: PRT
<213> ORGANISM: Artificial Sequence
<220> FEATURE:
<223> OTHER INFORMATION: clone C2G4_Variable light chain CDR3

<400> SEQUENCE: 119

Gly Ser Trp Asp Pro Ser Leu Asn Gly Tyr Val
1               5                   10

<210> SEQ ID NO 120
<211> LENGTH: 11
<212> TYPE: PRT
<213> ORGANISM: Artificial Sequence
<220> FEATURE:
<223> OTHER INFORMATION: clone C3C8_Variable light chain CDR3

<400> SEQUENCE: 120

Gly Ser Trp Asp Ser Asp Leu Arg Gly Tyr Val
1               5                   10

<210> SEQ ID NO 121
<211> LENGTH: 17
<212> TYPE: PRT
<213> ORGANISM: Artificial Sequence
<220> FEATURE:
<223> OTHER INFORMATION: clone 54_Variable heavy chain CDR2

<400> SEQUENCE: 121

Gly Ile Pro Pro Asp Ser Ser Ser Lys Tyr Tyr Ala Asp Ser Val Arg
1               5                   10                  15

Gly

<210> SEQ ID NO 122
<211> LENGTH: 17
<212> TYPE: PRT
<213> ORGANISM: Artificial Sequence
<220> FEATURE:
<223> OTHER INFORMATION: clone 56_Variable heavy chain CDR2

<400> SEQUENCE: 122

Gly Ile Pro Pro Asp Ser Ala Ser Lys Tyr Tyr Ala Asp Ser Val Arg
1               5                   10                  15

Gly

<210> SEQ ID NO 123
<211> LENGTH: 17
<212> TYPE: PRT
<213> ORGANISM: Artificial Sequence
<220> FEATURE:
<223> OTHER INFORMATION: clone 2-30_Variable heavy chain CDR2

<400> SEQUENCE: 123

Gly Ile Pro Pro Asp Ser Asn Ser Lys Tyr Tyr Ala Asp Ser Val Arg
1               5                   10                  15

Gly

<210> SEQ ID NO 124
<211> LENGTH: 7
<212> TYPE: PRT
<213> ORGANISM: Artificial Sequence
<220> FEATURE:
<223> OTHER INFORMATION: clone 2-30_Variable heavy chain CDR3

<400> SEQUENCE: 124
```

Asn Met Arg Thr Phe Asp Tyr
1               5

<210> SEQ ID NO 125
<211> LENGTH: 17
<212> TYPE: PRT
<213> ORGANISM: Artificial Sequence
<220> FEATURE:
<223> OTHER INFORMATION: clone 2-73_Variable heavy chain CDR2

<400> SEQUENCE: 125

Gly Ile Pro Pro Asn Ser Asp Ser Lys Tyr Tyr Ala Asp Ser Val Arg
1               5                   10                  15

Gly

<210> SEQ ID NO 126
<211> LENGTH: 7
<212> TYPE: PRT
<213> ORGANISM: Artificial Sequence
<220> FEATURE:
<223> OTHER INFORMATION: clone 2-78_Variable heavy chain CDR3

<400> SEQUENCE: 126

Asn Met Phe Ser Phe Asp Tyr
1               5

<210> SEQ ID NO 127
<211> LENGTH: 622
<212> TYPE: PRT
<213> ORGANISM: Artificial Sequence
<220> FEATURE:
<223> OTHER INFORMATION: Mesothelin

<400> SEQUENCE: 127

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
        50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

```
Pro Gly Arg Phe Val Ala Glu Ser Ala Glu Val Leu Leu Pro Arg Leu
            195                 200                 205

Val Ser Cys Pro Gly Pro Leu Asp Gln Asp Gln Gln Glu Ala Ala Arg
            210                 215                 220

Ala Ala Leu Gln Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
            245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
            275                 280                 285

Leu Arg Pro Arg Phe Arg Arg Glu Val Glu Lys Thr Ala Cys Pro Ser
            290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
            325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
            355                 360                 365

Ile Gln His Leu Gly Tyr Leu Phe Leu Lys Met Ser Pro Glu Asp Ile
            370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
            405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
            435                 440                 445

Leu Ser Ser Val Pro Pro Ser Ser Ile Trp Ala Val Arg Pro Gln Asp
450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
            485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
            515                 520                 525

Asp Ala Val Leu Pro Leu Thr Val Ala Glu Val Gln Lys Leu Leu Gly
            530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
            565                 570                 575

Gly Leu Gln Gly Gly Ile Pro Asn Gly Tyr Leu Val Leu Asp Leu Ser
            580                 585                 590
```

```
Met Gln Glu Ala Leu Ser Gly Thr Pro Cys Leu Leu Gly Pro Gly Pro
            595                 600                 605

Val Leu Thr Val Leu Ala Leu Leu Ala Ser Thr Leu Ala
            610                 615                 620
```